US010141518B2

(12) United States Patent
Stoessel et al.

(10) Patent No.: US 10,141,518 B2
(45) Date of Patent: *Nov. 27, 2018

(54) COMPOUNDS FOR ELECTRONIC DEVICES

(71) Applicant: Merck Patent GmbH, Darmstadt (DE)

(72) Inventors: Philipp Stoessel, Frankfurt am Main (DE); Arne Buesing, Frankfurt am Main (DE); Frank Voges, Bad Duerkheim (DE); Christof Pflumm, Darmstadt (DE); Amir Parham, Frankfurt am Main (DE); Thomas Eberle, Landau (DE); Teresa Mujica-Fernaud, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/447,882

(22) Filed: Mar. 2, 2017

(65) Prior Publication Data
US 2017/0179399 A1   Jun. 22, 2017

Related U.S. Application Data

(63) Continuation of application No. 14/112,344, filed as application No. PCT/EP2012/001285 on Mar. 23, 2012.

(30) Foreign Application Priority Data

Apr. 18, 2011   (EP) ..................... 11003230

(51) Int. Cl.
| H01L 51/50  | (2006.01) |
| H01L 51/00  | (2006.01) |
| C09K 11/06  | (2006.01) |
| H05B 33/14  | (2006.01) |
| C07C 209/60 | (2006.01) |
| C07C 211/54 | (2006.01) |
| C07C 211/56 | (2006.01) |
| C07C 211/58 | (2006.01) |
| C07C 213/00 | (2006.01) |
| C07C 217/92 | (2006.01) |
| C07C 253/30 | (2006.01) |
| C07C 255/58 | (2006.01) |
| C07D 209/86 | (2006.01) |
| C07D 235/18 | (2006.01) |
| C07D 249/18 | (2006.01) |
| C07D 265/38 | (2006.01) |
| C09K 11/02  | (2006.01) |

(52) U.S. Cl.
CPC ........ *H01L 51/0071* (2013.01); *C07C 209/60* (2013.01); *C07C 211/54* (2013.01); *C07C 211/56* (2013.01); *C07C 211/58* (2013.01); *C07C 213/00* (2013.01); *C07C 217/92* (2013.01); *C07C 253/30* (2013.01); *C07C 255/58* (2013.01); *C07D 209/86* (2013.01); *C07D 235/18* (2013.01); *C07D 249/18* (2013.01); *C07D 265/38* (2013.01); *C09K 11/025* (2013.01); *C09K 11/06* (2013.01); *H01L 51/006* (2013.01); *H01L 51/0059* (2013.01); *H01L 51/0069* (2013.01); *H01L 51/0072* (2013.01); *H01L 51/5016* (2013.01); *H01L 51/5056* (2013.01); *H05B 33/14* (2013.01); *C09K 2211/1003* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1074* (2013.01); *C09K 2211/185* (2013.01); *H01L 51/0058* (2013.01); *H01L 51/5072* (2013.01); *H01L 51/5096* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| 5,508,136 A    | 4/1996 | Shirota et al. |
| 6,699,556 B2   | 3/2004 | Saito |
| 2002/0045061 A1 | 4/2002 | Hosokawa |

(Continued)

FOREIGN PATENT DOCUMENTS

| JP | 2002-172865 A | 6/2002 |
| JP | 2004171808 A  | 6/2004 |

(Continued)

OTHER PUBLICATIONS

Stoeber et al., "Functional polymers 64. Potassium ionization of desorbed species (K+IDS) of 2-(2-hydroxyphenyl)-2H-benzotriazoles", Journal of Macromolecular Science, Pure and Applied Chemistry, vol. A37, No. 11, pp. 1269-1300 (2000).

Ghasemi et al., "Performance study of 1,3,5-tris(5-amino-3-nitro-1,2,4-triazolyl)-2,4,6-trinitrobenzene as a new thermally stable explosive", New Trends in Research of Energetic Materials, Proceedings of the Seminar, 13th, Pardubice, Czech Republic, vol. Pt. 2, pp. 489-491(2010).

(Continued)

*Primary Examiner* — Gregory D Clark

(57) ABSTRACT

The present invention relates to a compound of the formula (I), to the use of this compound in an electronic device, and to an electronic device comprising one or more compounds of the formula (I). The invention furthermore relates to the preparation of the compound of the formula (I) and to a formulation comprising one or more compounds of the formula (I).

20 Claims, No Drawings

(56) References Cited

U.S. PATENT DOCUMENTS

| | | | |
|---|---|---|---|
| 2004/0170863 A1* | 9/2004 | Kim | C07C 13/72 |
| | | | 428/690 |
| 2009/0302752 A1 | 12/2009 | Parham et al. | |
| 2010/0308714 A1* | 12/2010 | Gessner | C07D 279/26 |
| | | | 313/504 |

FOREIGN PATENT DOCUMENTS

| | | | |
|---|---|---|---|
| JP | 2006080271 A | | 3/2006 |
| WO | 07-097355 A | | 4/1995 |
| WO | WO-2007046486 A1 | | 4/2007 |
| WO | WO-2008/086851 A1 | | 7/2008 |

OTHER PUBLICATIONS

Zhang et al., "1,3,5-Trichloro-2,4,6-tripyrrol-1-ylbenzene", Acta Crystallographica, Section E; Structure Reports Online, vol. 63, No. 2, pp. o604-o605 (2007).

Zeng et al., "Energetic polyazole polynitrobenzenes and their coordination complexes", Chemical Communications (Cambridge, United Kingdom), No. 40, pp. 6014-6016 (2009).

International Search Report for PCT/EP2012/001285 dated Aug. 1, 2012.

Jiang et al., "Functional Polymers. LV. Photochemical Behavior of 2(2-hydroxyphenyl)2H-benzotriazole Derivatives", Polymer Bulletin, vol. 20, pp. 161-168 (1988).

Korean Office Action dated Nov. 10, 2017 for Korean Patent Application No. 10-2013-7030336.

\* cited by examiner

COMPOUNDS FOR ELECTRONIC DEVICES

CROSS-REFERENCE TO RELATED APPLICATIONS

This application is a continuation application, and claims benefit under 35 U.S.C. § 120, of U.S. patent application Ser. No. 14/112,344 filed Oct. 17, 2013, which is a national stage application (under 35 U.S.C. § 371) of PCT/EP2012/001285, filed Mar. 23, 2012, and which claims benefit of European Application No. 11003230.7, filed Apr. 18, 2011, and each application is incorporated herein by reference in their entirety.

The present invention relates to a compound of a formula (I), to the use of this compound in an electronic device, and to an electronic device comprising one or more compounds of the formula (I). The invention furthermore relates to the preparation of the compound of the formula (I) and to a formulation comprising one or more compounds of the formula (I).

BACKGROUND OF THE INVENTION

The development of novel functional compounds for use in electronic devices is currently the subject of intensive research. The aim here is the development and investigation of compounds which have hitherto not been employed in electronic devices, and the development of compounds which enable an improved property profile of the devices.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

The structure of organic electroluminescent devices (OLEDs) in which the compounds of the formula (I) can preferably be employed as functional materials is known to the person skilled in the art and is described, inter alia, in U.S. Pat. No. 4,539,507, U.S. Pat. No. 5,151,629, EP 0676461 and WO 1998/27136.

Further improvements are still necessary concerning the performance data of the organic electroluminescent devices, in particular in view of broad commercial use. Of particular importance in this connection are the lifetime, the efficiency and the operating voltage of the organic electroluminescent devices and the colour values achieved. In particular in the case of blue-emitting electroluminescent devices, there is potential for improvement with respect to the lifetime of the devices. In addition, it is desirable for the compounds, for use as functional materials in electronic devices, to have high thermal stability and a high glass-transition temperature and to be sublimable without decomposition.

In this connection, there is a need for alternative hole-transport materials for use in electronic devices. In the case of hole-transport materials in accordance with the prior art, the voltage generally increases with the layer thickness of the hole-transport layer. In practice, a greater layer thickness of the hole-transport layer would frequently be desirable, but this often has the consequence of a higher operating voltage and worse performance data. In this connection, there is a need for novel hole-transport materials which have high charge-carrier mobility, making it possible to achieve thicker hole-transport layers with only a slight increase in the operating voltage.

In accordance with the prior art, the hole-transport materials used in the hole-transport layer or in the hole-injection layer are, in particular, triarylamine derivatives which contain two triarylamino groups. These compounds are frequently derived from diarylamino-substituted triphenylamines (TPA-type), from diarylamino-substituted biphenyl derivatives (TAD-type) or combinations of these basic compounds. Furthermore, use is made, for example, of spirobifluorene derivatives which are substituted by two or four diarylamino groups (for example in accordance with EP 676461). In the case of these compounds, there continues to be a need for improvement, in particular with respect to efficiency, lifetime and operating voltage, both in the case of fluorescent and phosphorescent OLEDs, on use in an organic electroluminescent device and with respect to the thermal stability during sublimation.

Furthermore, so-called starburst amines are known from the prior art for use in OLEDs, Starburst amines, which contain three diarylamino groups which are bonded to a common central benzene ring, where the central benzene ring is unsubstituted at the remaining positions, are disclosed, inter glia, in EP 0611148 for the preferred use in a hole-transport layer. However, these compounds are only suitable to a slight extent for use as hole-transporting material in an emitting layer comprising blue- or green-phosphorescent emitter compounds.

There continues to be a need for alternative matrix materials for use in electronic devices. In particular, there is a need for matrix materials for phosphorescent emitters which simultaneously result in good efficiency, a long lifetime and a low operating voltage. Specifically the properties of the matrix materials are frequently limiting for the lifetime and the efficiency of the organic electroluminescent device. In particular, it is desirable for matrix materials for phosphorescent emitters for these to have a high $T_1$ level (triplet level).

In accordance with the prior art, carbazole derivatives, for example bis(carbazolyl)biphenyl, are frequently used as matrix materials. Furthermore, ketones (WO 2004/093207), phosphine oxides, sulfones (WO 2005/003253), triazine compounds, such as triazinylspirobifluorene (cf. WO 2005/053055 and WO 2010/015306), and metal complexes, for example BAlq or zinc(II) bis[2-(2-benzothiazole)phenolate], are used as matrix materials for phosphorescent emitters. However, there continues to be a need for alternative compounds for use as matrix materials for phosphorescent emitters. In particular, there is a need for compounds with which an improvement in the performance data of the electronic devices can be achieved.

DETAILED DESCRIPTION OF THE INVENTION

The present invention is thus based on the technical object of providing compounds which are suitable for use in electronic devices, such as, for example, OLEDs, and which can be employed, in particular, as hole-transport materials and as matrix materials for phosphorescent emitters.

As part of the present invention, it has now been found that compounds of the formula (I) indicated below are eminently suitable for use in electronic devices, in particular as hole-transport materials and as matrix materials for phosphorescent emitters. These compounds have the characterising feature of three arylamino groups or N-heterocyclic groups which are bonded to a common central benzene ring. Furthermore, the compounds are characterised in that they are substituted at the remaining three positions of the central benzene ring.

The invention thus relates to a compound of a formula (I)

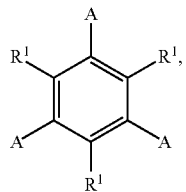

where A represents on each occurrence, identically or differently, a group of the following formula (II) or (III)

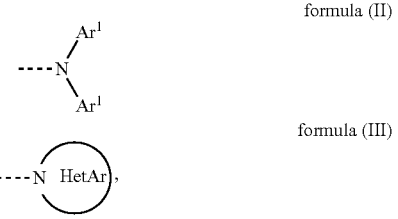

where the dashed line emanating from the nitrogen atom represents the bond from the group A to the central benzene ring;
where the group HetAr including the nitrogen atom shown represents on each occurrence, identically or differently, a heteroaryl group having 5 to 30 aromatic ring atoms, which may be substituted by one or more radicals $R^2$;
where the group $Ar^1$ represents on each occurrence, identically or differently, an aromatic or heteroaromatic ring system having 5 to 30 aromatic ring atoms, which may be substituted by one or more radicals $R^2$, and where the two groups $Ar^1$ may be connected via a group Y so that a ring is formed with the nitrogen atom of the group A, where
Y is selected from a single bond, $BR^2$, $C(R^2)_2$, $Si(R^2)_2$, $NR^2$, $PR^2$, $P(=O)R^2$, $P(=S)R^2$, O, S, S=O and $S(=O)_2$;
and where furthermore:
$R^1$ is on each occurrence, identically or differently, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $NO_2$, $P(=O)(R^3)_2$, $OSO_2R^3$, $OR^3$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by $—R^3C=CR^3—$, $—C≡C—$, $Si(R^3)_2$, C=O, C=S, C=NR^3$, $—C(=O)O—$, $—C(=O)NR^3—$, $NR^3$, $P(=O)(R^3)$, $—O—$, $—S—$, SO or $SO_2$ and where one or more H atoms in the above-mentioned groups may be replaced by D, F, Cl, Br, I, CN or $NO_2$, or an aromatic ring system having 6 to 60 aromatic ring atoms, which may in each case be substituted by one or more radicals $R^3$, or a heteroaromatic ring system having 5 to 60 aromatic ring atoms, which is not bonded via a ring nitrogen atom, and which may be substituted by one or more radicals $R^3$, or an aryloxy or heteroaryloxy group having 5 to 60 aromatic ring atoms, which may be substituted by one or more radicals $R^3$, or an aralkyl or heteroaralkyl group having 5 to 60 aromatic ring atoms, which may be substituted by one or more radicals $R^3$;
$R^2$ is on each occurrence, identically or differently, H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by $—R^3C=CR^3—$, $—C≡C—$, $Si(R^3)_2$, C=O, C=S, C=NR^3$, $—C(=O)O—$, $—C(=O)NR^3—$, $NR^3$, $P(=O)(R^3)$, $—O—$, $—S—$, SO or $SO_2$ and where one or more H atoms in the above-mentioned groups may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, or an aralkyl or heteroaralkyl group having 5 to 60 aromatic ring atoms, which may be substituted by one or more radicals $R^3$, where two or more radicals $R^2$ may be linked to one another and may form a ring;
$R^3$ is on each occurrence, identically or differently, H, D, F, Cl, Br, I, $B(OR^4)_2$, CHO, $C(=O)R^4$, $CR^4=C(R^4)_2$, CN, $C(=O)OR^4$, $C(=O)N(R^4)_2$, $Si(R^4)_3$, $N(R^4)_2$, $NO_2$, $P(=O)(R^4)_2$, $OSO_2R^4$, $OR^4$, $S(=O)R^4$, $S(=O)_2R^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups may be replaced by $—R^4C=CR^4—$, $—C≡C—$, $Si(R^4)_2$, C=O, C=S, C=NR^4$, $—C(=O)O—$, $—C(=O)NR^4—$, $NR^4$, $P(=O)(R^4)$, $—O—$, $—S—$, SO or $SO_2$ and where one or more H atoms in the above-mentioned groups may be replaced by D, F, Cl, Br, I, CN or $NO_2$, or an aromatic or heteroaromatic ring system having 5 to 60 aromatic ring atoms, which may in each case be substituted by one or more radicals $R^4$, or an aryloxy or heteroaryloxy group having 5 to 60 aromatic ring atoms, which may be substituted by one or more radicals $R^4$, or an aralkyl or heteroaralkyl group having 5 to 60 aromatic ring atoms, which may be substituted by one or more radicals $R^4$, where two or more radicals $R^3$ may be linked to one another and may form a ring;
$R^4$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^4$ here may be linked to one another and may form a ring.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

For the purposes of the present invention, an aryl group or heteroaryl group is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aralkyl group in the sense of this invention is an alkyl group which is substituted by an aryl group, where the term aryl group is to be understood as defined above and the alkyl group has 1 to 20 C atoms, where individual H atoms and/or $CH_2$ groups in the alkyl group may also be replaced by the groups mentioned under the definition of the alkyl groups and where the alkyl group represents the group which is bonded to the remainder of the compound. Correspondingly, a heteroaralkyl group represents an alkyl group which is substituted by a heteroaryl group, where the term heteroaryl group is to be understood as defined above and the alkyl group has 1 to 20 C atoms, where individual H atoms and/or $CH_2$ groups in the alkyl group may also be replaced by the groups mentioned under the definition of the alkyl groups and where the alkyl group represents the group which is bonded to the remainder of the compound.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclo-pentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, the purposes of the present description, intended to be taken to mean, inter alia, that the two radicals are linked to one another by a chemical bond. This is illustrated by the following scheme:

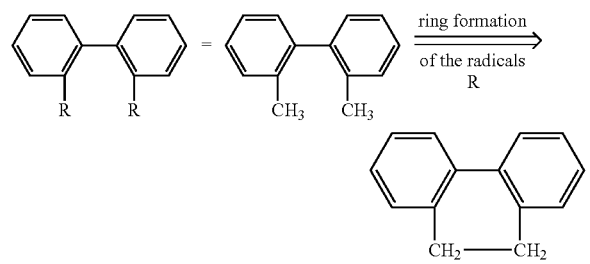

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

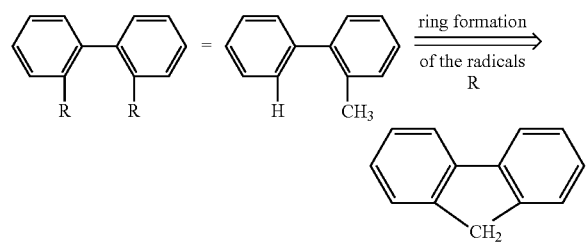

In accordance with the present invention, the compound of the formula (I) can conform to the following formulae (I-1) or (I-2):

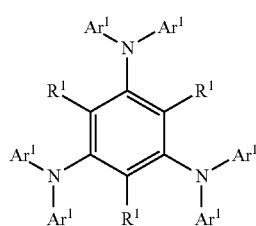

formula (I-1)

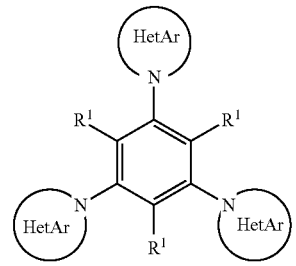

formula (I-2)

where the symbols are defined as above in connection with the definition of the formula (I).

According to a preferred embodiment, the group Ar$^1$ as constituent of the group A of the formula (II) represents an aryl group having 6 to 20 aromatic ring atoms, which may be substituted by one or more radicals R$^2$. According to another preferred embodiment, the group Ar$^1$ as constituent of the group A of the formula (II) represents a heteroaryl group having 5 to 20 aromatic ring atoms, which may be substituted by one or more radicals R$^2$. The heteroatoms of the heteroaryl group are preferably selected from N, O and S.

Ar$^1$ as constituent of the group A of the formula (II) very particularly preferably represents an aryl group having 6 to 10 aromatic ring atoms, even more preferably an aryl group having 6 aromatic ring atoms, where Ar$^1$ may be substituted by one or more radicals R$^2$.

According to a particularly preferred embodiment, the group Ar$^1$ is selected from phenyl, p-biphenyl, m-biphenyl, o-biphenyl, terphenyl, quaterphenyl, naphthyl, anthracenyl, phenanthrenyl, pyrenyl, chrysenyl, perylenyl, fluoranthenyl, benzanthracenyl, benzophenanthrenyl, tetracenyl, benzopyrenyl, fluorenyl, spirobifluorenyl, cis- or trans-indenofluorenyl, furanyl, benzofuranyl, isobenzofuranyl, dibenzofuranyl, thiophenyl, benzothiophenyl, isobenzothiophenyl, dibenzothiophenyl, pyrrolyl, indolyl, isoindolyl, carbazolyl, pyridinyl, quinolinyl, isoquinolinyl, acridinyl, phenanthridinyl, pheno-thiazinyl, phenoxazinyl, pyrazolyl, imidazolyl, benzimidazolyl, oxazolyl, benzoxazolyl, isoxazolyl, thiazolyl, benzothiazolyl, pyridazinyl, benzo-pyridazinyl, pyrimidinyl, quinoxalinyl, pyrazinyl, phenazinyl, azacarbazolyl, phenanthrolinyl, triazolyl, benzotriazolyl, oxadiazolyl, thiadiazolyl and triazinyl, each of which may be substituted by one or more radicals R$^2$.

It is furthermore preferred for the two groups Ar$^1$ which are bonded to a common N atom in a group of the formula (II) to be selected identically.

In accordance with the invention, the group A may represent a group of the formula (II). In this case, it is preferred for the group A to represent a group of the following formulae (II-1) to (II-11):

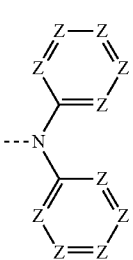

formula (II-1)

formula (II-2)
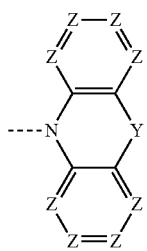
formula (II-3)
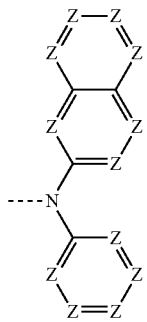
formula (II-4)
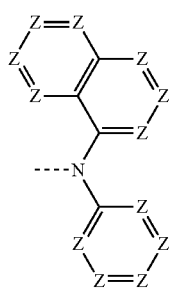
formula (II-5)
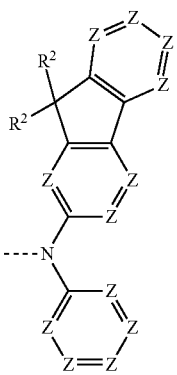
formula (II-6)
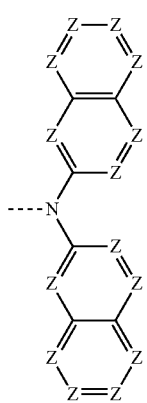
formula (II-7)
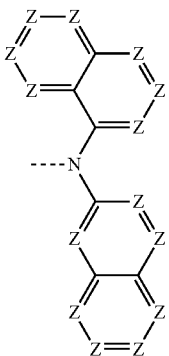
formula (II-8)
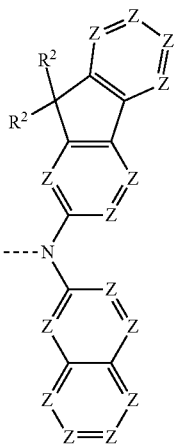
formula (II-9)
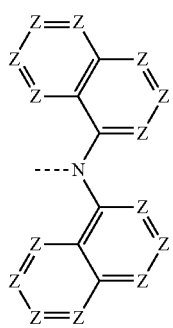
formula (II-10)
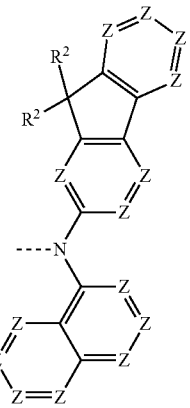

formula (II-11)

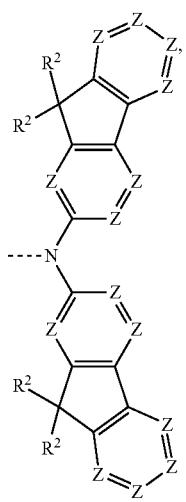

where R² is as defined above,

Z represents on each occurrence, identically or differently, CR² or N; and

Y is selected from a single bond, BR², C(R²)₂, Si(R²)₂, NR², PR², P(=O)R², O, S, S=O and S(=O)₂.

In the formulae shown above, it is preferred for a maximum of 2 adjacent groups Z to be equal to N. It is furthermore preferred for 0, 1, 2 or 3 groups Z per aromatic ring to be equal to N, particularly preferably 0, 1 or 2 and very particularly preferably 0 or 1.

According to a preferred embodiment, Y is selected from a single bond, C(R²)₂, NR², O and S.

According to a preferred embodiment, the radicals R² of a group C(R²)₂ which stands for Y form a ring with one another, so that a spiro system is formed. A group of the formulae (Y-1) to (Y-8) is particularly preferably formed here

formula (Y-1)

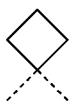

formula (Y-2)

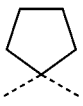

formula (Y-3)

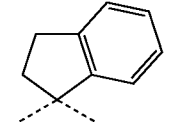

formula (Y-4)

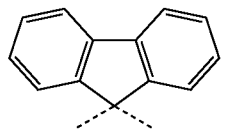

formula (Y-5)

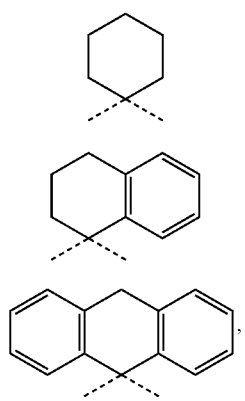

formula (Y-6)

formula (Y-7)

formula (Y-8)

where the groups depicted may optionally be substituted by one or more radicals R² in the positions shown as unsubstituted.

In accordance with the invention, the group A may alternatively represent a group of the formula (III). In this case, it is preferred for the group A to represent a group of the following formulae (III-1) to (III-3):

formula (III-1)

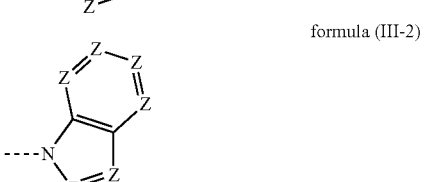

formula (III-2)

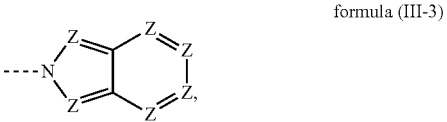

formula (III-3)

where

Z represents on each occurrence, identically or differently, CR² or N.

The above-mentioned preferred embodiments relating to the group Z also apply in this connection.

It is particularly preferred for A to be selected from pyrrole, indole, imidazole, benzimidazole, pyrazole, benzopyrazole, 1,2,3-triazole, benzotriazole, 1,2,4-triazole and tetrazole, each of which may be substituted by one or more radicals R².

It should be noted that the groups A in the compound of the formula (I) according to the invention need not necessarily be selected identically, but may instead also be different. In accordance with a preferred embodiment, however, the groups A in a compound of the formula (I) according to the invention are selected identically.

For the group R¹, it is preferred in accordance with the invention for it to be selected on each occurrence, identically or differently, from F, CN, Si(R³)₃, or a straight-chain alkyl or alkoxy group having 1 to 10 C atoms or a branched or cyclic alkyl or alkoxy group having 3 to 10 C atoms, or an alkenyl or alkynyl group having 2 to 10 C atoms, where the above-mentioned groups may each be substituted by one or more radicals $R^3$ and where one or more $CH_2$ groups in the above-mentioned groups may be replaced by —C≡C—, —$R^3$C=C$R^3$—, Si($R^3$)$_2$, C=O, C=N$R^3$, —N$R^3$—, —O—, —S—, —C(=O)O— or —C(=O)N$R^3$—, or an aromatic ring system having 5 to 20 aromatic ring atoms, which may in each case be substituted by one or more radicals $R^3$, or a heteroaromatic ring system, which is not bonded via a ring nitrogen atom, and which is in each case substituted by one or more radicals $R^3$.

$R^1$ is particularly preferably selected from F, CN, Si($R^3$)$_3$, straight-chain $C_1$, $C_2$, $C_3$, $C_4$, $C_5$, $C_6$, $C_7$ or $C_8$-alkyl, which may be substituted by one or more radicals $R^3$, branched $C_3$, $C_4$, $C_5$, $C_6$, $C_7$ or $C_8$-alkyl, which may be substituted by one or more radicals $R^3$, cyclic $C_4$, $C_5$ or $C_6$-alkyl, which may be substituted by one or more radicals $R^3$, or $C_2$, $C_3$, $C_4$, $C_5$, $C_6$, $C_7$ or $C_8$-alkynyl, which may contain one or more C—C triple bonds and which may be substituted by one or more radicals $R^3$, or an aryl group having 6 to 10 aromatic ring atoms, very particularly preferably phenyl, which may be substituted by one or more radicals $R^3$, or a heteroaryl group having 5 to 10 aromatic ring atoms, which is not bonded via a ring nitrogen atom, very particularly preferably pyridyl, pyrazinyl, pyridazinyl, pyrimidyl and triazinyl, each of which may be substituted by one or more radicals $R^3$.

According to a further preferred embodiment, the radicals $R^1$ in the compound of the formula (I) according to the invention are selected identically. However, they may also be selected differently.

The radical $R^2$ is preferably selected on each occurrence, identically or differently, from H, D, F, ON, Si($R^3$)$_3$, N($R^3$)$_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more $CH_2$ groups in the above-mentioned groups may be replaced by —C≡C—, —$R^3$C=C$R^3$—, Si($R^3$)$_2$, C=O, C=N$R^3$, —N$R^3$—, —O—, —S—, —C(=O)O— or —C(=O)N$R^3$—, or an aromatic or heteroaromatic ring system having 5 to 20 aromatic ring atoms, which may in each case be substituted by one or more radicals $R^3$, where two or more radicals $R^2$ may be linked to one another and may form a ring.

The radical $R^3$ is preferably selected on each occurrence, identically or differently, from H, D, F, ON, Si($R^4$)$_3$, N($R^4$)$_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more $CH_2$ groups in the above-mentioned groups may be replaced by —C≡C—, —$R^4$C=C$R^4$—, Si($R^4$)$_2$, C=O, C=N$R^4$, —N$R^4$—, —O—, —S—, —C(=O)O— or —C(=O)N$R^4$—, or an aromatic or heteroaromatic ring system having 5 to 20 aromatic ring atoms, which may in each case be substituted by one or more radicals $R^4$, where two or more radicals $R^3$ may be linked to one another and may form a ring.

Particularly preferred groups A in the compounds of the formula (I) according to the invention are the following groups A-1 to A-48:

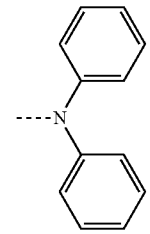

A-1

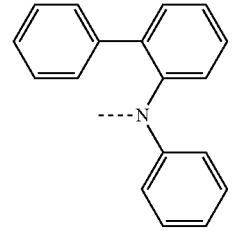

A-2

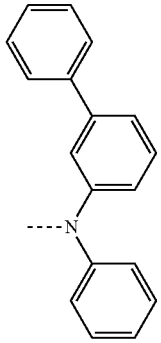

A-3

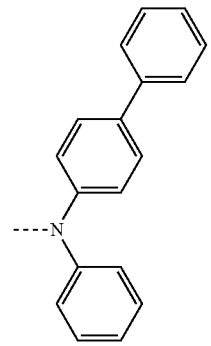

A-4

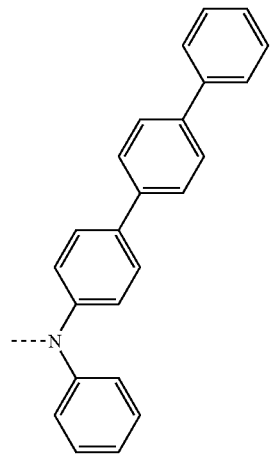

A-5

-continued
A-6
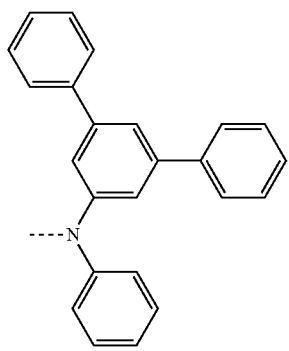
A-7
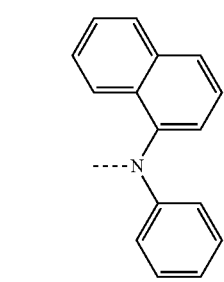
A-8
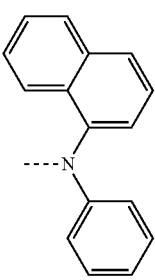
A-9
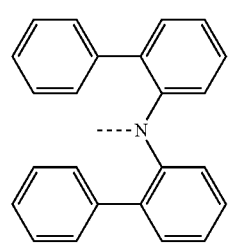
A-10
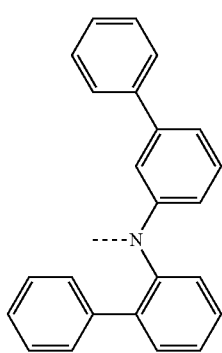
-continued
A-11
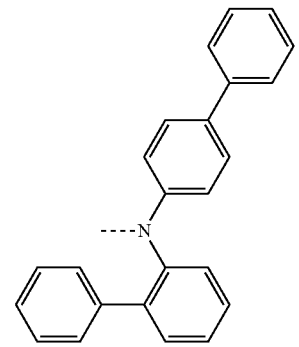
A-12
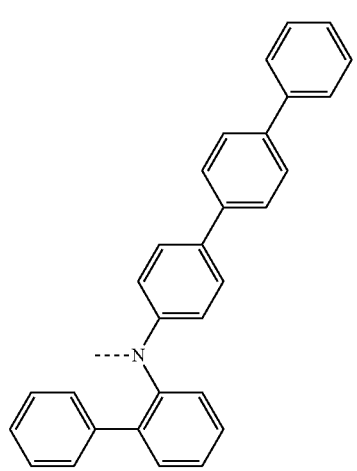
A-13
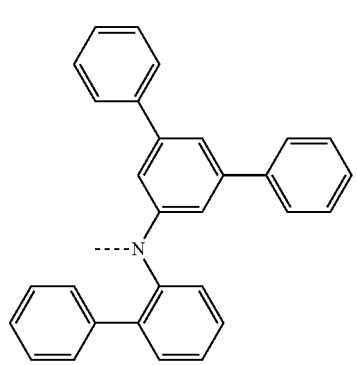
A-14
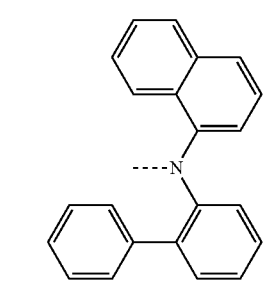

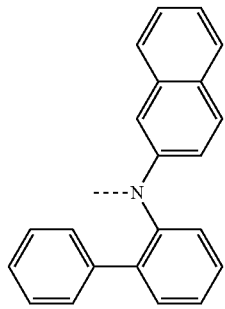 A-15
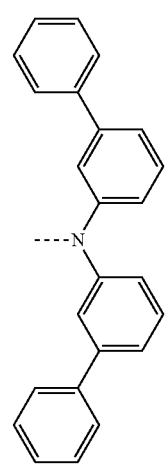 A-16
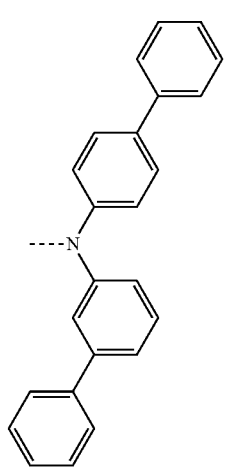 A-17
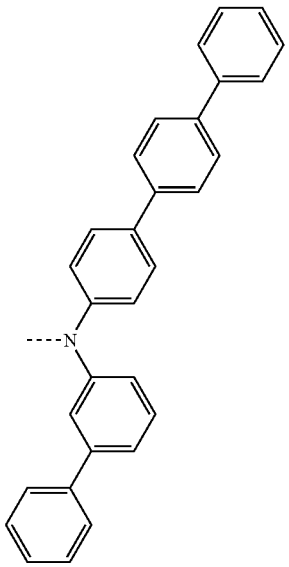 A-18
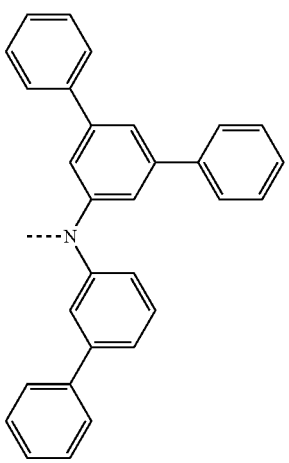 A-19
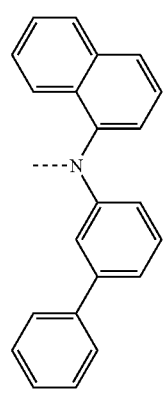 A-20

-continued
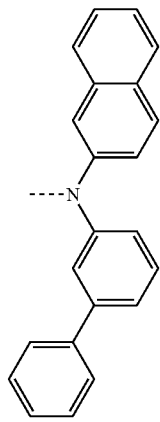
A-21
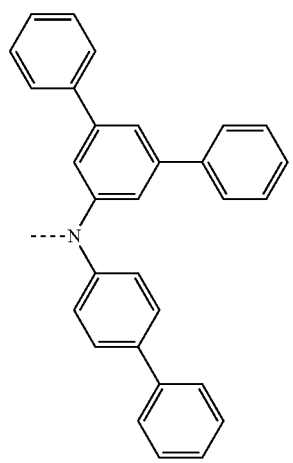
A-24
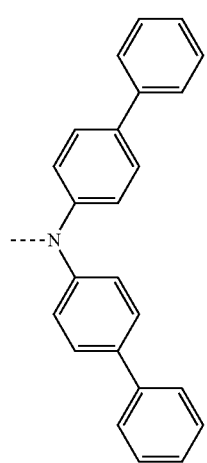
A-22
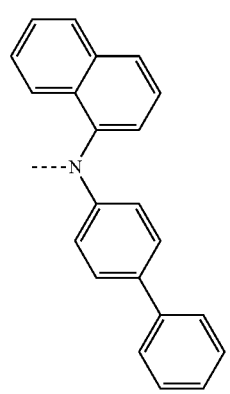
A-25
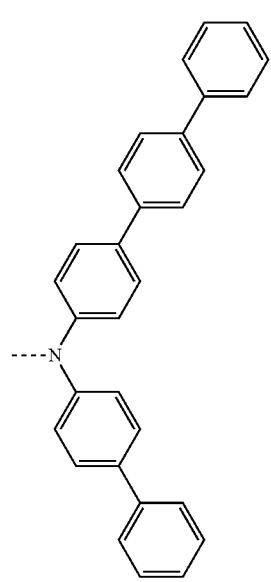
A-23
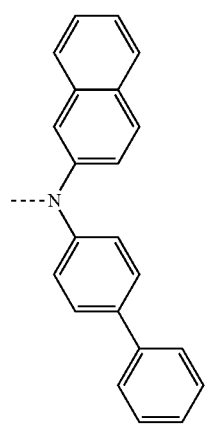
A-26

A-27
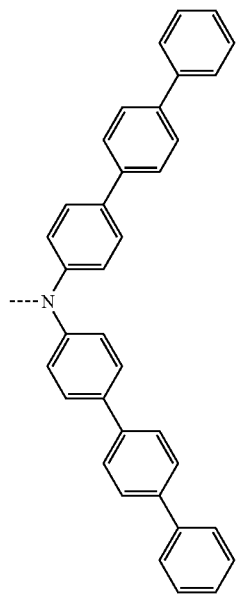
A-28
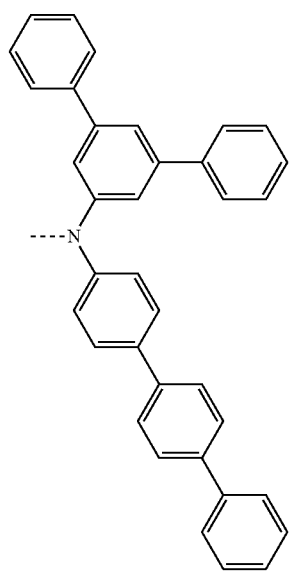
A-29
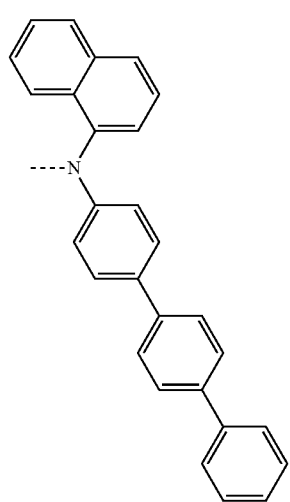
A-30
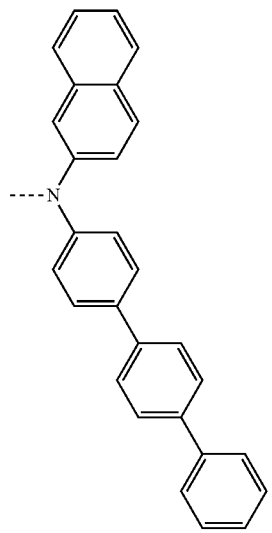
A-31
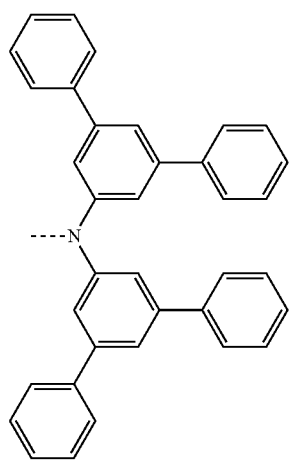
A-32
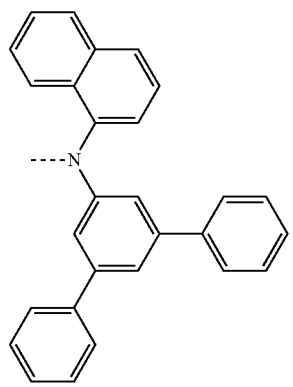

A-33
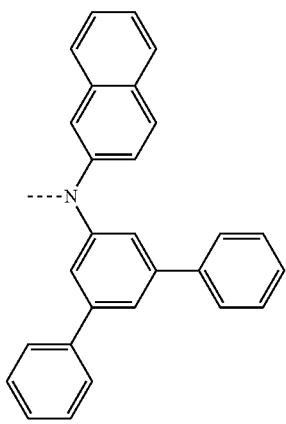
A-34
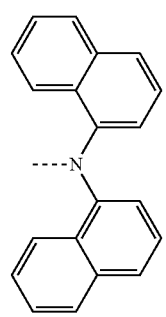
A-35
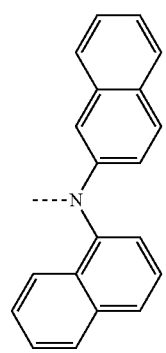
A-36
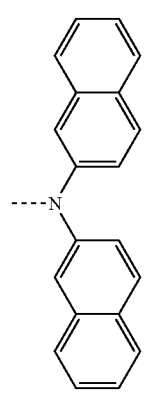
A-37
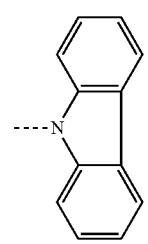
A-38
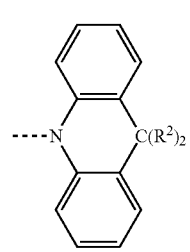
A-39
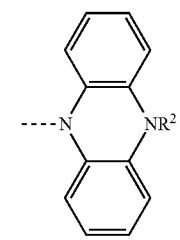
A-40
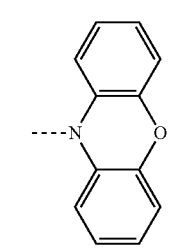
A-41
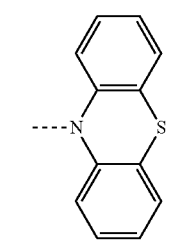
A-42
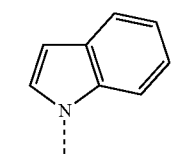
A-43
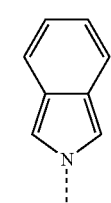

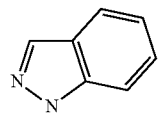

A-44

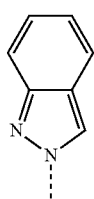

A-45

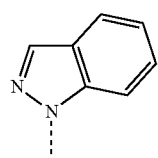

A-46

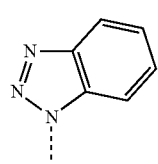

A-47

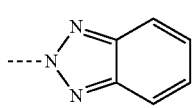

A-48 each of which may be substituted by one or more radicals $R^2$.

Particularly preferred groups $R^1$ in the compounds of the formula (I) according to the invention are the following groups R-1 to R-8:

| R-1 | —$CH_3$ |
| R-2 | —F |
| R-3 | —CN |
| R-4 | —$CH(CH_3)_2$ |
| R-5 | —$C(CH_3)_3$ |
| R-6 | —Ph |
| R-7 | —$CD_3$ |
| R-8 | $Si(CH_3)_3$ |

Preference is given to compounds of the following formula (I-3)

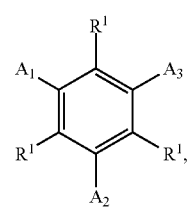

formula (I-3)

where $A_1$, $A_2$ and $A_3$ are selected from the radicals A-1 to A-48 indicated above, and $R^1$ is selected on each occurrence, identically or differently, from the radicals R-1 to R-8 indicated above. Preferably, all groups $R^1$ here are selected identically. Furthermore preferably, the groups $A_1$, $A_2$ and $A_3$ here are selected identically. According to an alternative preferred embodiment, precisely two groups selected from the groups $A_1$, $A_2$ and $A_3$ are selected identically, and the remaining group selected from the groups $A_1$, $A_2$ and $A_3$ is selected differently.

Particular preference is given to compounds of the formula (I-3), where the radicals $R^1$, $A_1$, $A_2$ and $A_3$ are selected as indicated in the following table.

|    | $R^1$ | $A_1$ | $A_2$ | $A_3$ |
|----|-------|-------|-------|-------|
| 1  | R-1 | A-1 | A-1 | A-1 |
| 2  | R-1 | A-1 | A-1 | A-9 |
| 3  | R-1 | A-1 | A-1 | A-16 |
| 4  | R-1 | A-1 | A-1 | A-22 |
| 5  | R-1 | A-1 | A-9 | A-1 |
| 6  | R-1 | A-1 | A-9 | A-9 |
| 7  | R-1 | A-1 | A-9 | A-16 |
| 8  | R-1 | A-1 | A-9 | A-22 |
| 9  | R-1 | A-1 | A-16 | A-1 |
| 10 | R-1 | A-1 | A-16 | A-9 |
| 11 | R-1 | A-1 | A-16 | A-16 |
| 12 | R-1 | A-1 | A-16 | A-22 |
| 13 | R-1 | A-1 | A-22 | A-1 |
| 14 | R-1 | A-1 | A-22 | A-9 |
| 15 | R-1 | A-1 | A-22 | A-16 |
| 16 | R-1 | A-1 | A-22 | A-22 |
| 17 | R-1 | A-9 | A-1 | A-1 |
| 18 | R-1 | A-9 | A-1 | A-9 |
| 19 | R-1 | A-9 | A-1 | A-16 |
| 20 | R-1 | A-9 | A-1 | A-22 |
| 21 | R-1 | A-9 | A-9 | A-1 |
| 22 | R-1 | A-9 | A-9 | A-9 |
| 23 | R-1 | A-9 | A-9 | A-16 |
| 24 | R-1 | A-9 | A-9 | A-22 |
| 25 | R-1 | A-9 | A-16 | A-1 |
| 26 | R-1 | A-9 | A-16 | A-9 |
| 27 | R-1 | A-9 | A-16 | A-16 |
| 28 | R-1 | A-9 | A-16 | A-22 |
| 29 | R-1 | A-9 | A-22 | A-1 |
| 30 | R-1 | A-9 | A-22 | A-9 |
| 31 | R-1 | A-9 | A-22 | A-16 |
| 32 | R-1 | A-9 | A-22 | A-22 |
| 33 | R-1 | A-16 | A-1 | A-1 |
| 34 | R-1 | A-16 | A-1 | A-9 |
| 35 | R-1 | A-16 | A-1 | A-16 |
| 36 | R-1 | A-16 | A-1 | A-22 |
| 37 | R-1 | A-16 | A-9 | A-1 |
| 38 | R-1 | A-16 | A-9 | A-9 |
| 39 | R-1 | A-16 | A-9 | A-16 |
| 40 | R-1 | A-16 | A-9 | A-22 |
| 41 | R-1 | A-16 | A-16 | A-1 |
| 42 | R-1 | A-16 | A-16 | A-9 |
| 43 | R-1 | A-16 | A-16 | A-16 |
| 44 | R-1 | A-16 | A-16 | A-22 |
| 45 | R-1 | A-16 | A-22 | A-1 |
| 46 | R-1 | A-16 | A-22 | A-9 |
| 47 | R-1 | A-16 | A-22 | A-16 |
| 48 | R-1 | A-16 | A-22 | A-22 |
| 49 | R-1 | A-22 | A-1 | A-1 |
| 50 | R-1 | A-22 | A-1 | A-9 |
| 51 | R-1 | A-22 | A-1 | A-16 |
| 52 | R-1 | A-22 | A-1 | A-22 |
| 53 | R-1 | A-22 | A-9 | A-1 |
| 54 | R-1 | A-22 | A-9 | A-9 |
| 55 | R-1 | A-22 | A-9 | A-16 |
| 56 | R-1 | A-22 | A-9 | A-22 |
| 57 | R-1 | A-22 | A-16 | A-1 |
| 58 | R-1 | A-22 | A-16 | A-9 |
| 59 | R-1 | A-22 | A-16 | A-16 |
| 60 | R-1 | A-22 | A-16 | A-22 |
| 61 | R-1 | A-22 | A-22 | A-1 |
| 62 | R-1 | A-22 | A-22 | A-9 |
| 63 | R-1 | A-22 | A-22 | A-16 |
| 64 | R-1 | A-22 | A-22 | A-22 |
| 65 | R-2 | A-1 | A-1 | A-1 |
| 66 | R-2 | A-1 | A-1 | A-9 |
| 67 | R-2 | A-1 | A-1 | A-16 |

-continued

| | R¹ | A₁ | A₂ | A₃ |
|---|---|---|---|---|
| 68 | R-2 | A-1 | A-1 | A-22 |
| 69 | R-2 | A-1 | A-9 | A-1 |
| 70 | R-2 | A-1 | A-9 | A-9 |
| 71 | R-2 | A-1 | A-9 | A-16 |
| 72 | R-2 | A-1 | A-9 | A-22 |
| 73 | R-2 | A-1 | A-16 | A-1 |
| 74 | R-2 | A-1 | A-16 | A-9 |
| 75 | R-2 | A-1 | A-16 | A-16 |
| 76 | R-2 | A-1 | A-16 | A-22 |
| 77 | R-2 | A-1 | A-22 | A-1 |
| 78 | R-2 | A-1 | A-22 | A-9 |
| 79 | R-2 | A-1 | A-22 | A-16 |
| 80 | R-2 | A-1 | A-22 | A-22 |
| 81 | R-2 | A-9 | A-1 | A-1 |
| 82 | R-2 | A-9 | A-1 | A-9 |
| 83 | R-2 | A-9 | A-1 | A-16 |
| 84 | R-2 | A-9 | A-1 | A-22 |
| 85 | R-2 | A-9 | A-9 | A-1 |
| 86 | R-2 | A-9 | A-9 | A-9 |
| 87 | R-2 | A-9 | A-9 | A-16 |
| 88 | R-2 | A-9 | A-9 | A-22 |
| 89 | R-2 | A-9 | A-16 | A-1 |
| 90 | R-2 | A-9 | A-16 | A-9 |
| 91 | R-2 | A-9 | A-16 | A-16 |
| 92 | R-2 | A-9 | A-16 | A-22 |
| 93 | R-2 | A-9 | A-22 | A-1 |
| 94 | R-2 | A-9 | A-22 | A-9 |
| 95 | R-2 | A-9 | A-22 | A-16 |
| 96 | R-2 | A-9 | A-22 | A-22 |
| 97 | R-2 | A-16 | A-1 | A-1 |
| 98 | R-2 | A-16 | A-1 | A-9 |
| 99 | R-2 | A-16 | A-1 | A-16 |
| 100 | R-2 | A-16 | A-1 | A-22 |
| 101 | R-2 | A-16 | A-9 | A-1 |
| 102 | R-2 | A-16 | A-9 | A-9 |
| 103 | R-2 | A-16 | A-9 | A-16 |
| 104 | R-2 | A-16 | A-9 | A-22 |
| 105 | R-2 | A-16 | A-16 | A-1 |
| 106 | R-2 | A-16 | A-16 | A-9 |
| 107 | R-2 | A-16 | A-16 | A-16 |
| 108 | R-2 | A-16 | A-16 | A-22 |
| 109 | R-2 | A-16 | A-22 | A-1 |
| 110 | R-2 | A-16 | A-22 | A-9 |
| 111 | R-2 | A-16 | A-22 | A-16 |
| 112 | R-2 | A-16 | A-22 | A-22 |
| 113 | R-2 | A-22 | A-1 | A-1 |
| 114 | R-2 | A-22 | A-1 | A-9 |
| 115 | R-2 | A-22 | A-1 | A-16 |
| 116 | R-2 | A-22 | A-1 | A-22 |
| 117 | R-2 | A-22 | A-9 | A-1 |
| 118 | R-2 | A-22 | A-9 | A-9 |
| 119 | R-2 | A-22 | A-9 | A-16 |
| 120 | R-2 | A-22 | A-9 | A-22 |
| 121 | R-2 | A-22 | A-16 | A-1 |
| 122 | R-2 | A-22 | A-16 | A-9 |
| 123 | R-2 | A-22 | A-16 | A-16 |
| 124 | R-2 | A-22 | A-16 | A-22 |
| 125 | R-2 | A-22 | A-22 | A-1 |
| 126 | R-2 | A-22 | A-22 | A-9 |
| 127 | R-2 | A-22 | A-22 | A-16 |
| 128 | R-2 | A-22 | A-22 | A-22 |
| 129 | R-3 | A-1 | A-1 | A-1 |
| 130 | R-3 | A-1 | A-1 | A-9 |
| 131 | R-3 | A-1 | A-1 | A-16 |
| 132 | R-3 | A-1 | A-1 | A-22 |
| 133 | R-3 | A-1 | A-9 | A-1 |
| 134 | R-3 | A-1 | A-9 | A-9 |
| 135 | R-3 | A-1 | A-9 | A-16 |
| 136 | R-3 | A-1 | A-9 | A-22 |
| 137 | R-3 | A-1 | A-16 | A-1 |
| 138 | R-3 | A-1 | A-16 | A-9 |
| 139 | R-3 | A-1 | A-16 | A-16 |
| 140 | R-3 | A-1 | A-16 | A-22 |
| 141 | R-3 | A-1 | A-22 | A-1 |
| 142 | R-3 | A-1 | A-22 | A-9 |
| 143 | R-3 | A-1 | A-22 | A-16 |
| 144 | R-3 | A-1 | A-22 | A-22 |
| 145 | R-3 | A-9 | A-1 | A-1 |
| 146 | R-3 | A-9 | A-1 | A-9 |
| 147 | R-3 | A-9 | A-1 | A-16 |
| 148 | R-3 | A-9 | A-1 | A-22 |
| 149 | R-3 | A-9 | A-9 | A-1 |
| 150 | R-3 | A-9 | A-9 | A-9 |
| 151 | R-3 | A-9 | A-9 | A-16 |
| 152 | R-3 | A-9 | A-9 | A-22 |
| 153 | R-3 | A-9 | A-16 | A-1 |
| 154 | R-3 | A-9 | A-16 | A-9 |
| 155 | R-3 | A-9 | A-16 | A-16 |
| 156 | R-3 | A-9 | A-16 | A-22 |
| 157 | R-3 | A-9 | A-22 | A-1 |
| 158 | R-3 | A-9 | A-22 | A-9 |
| 159 | R-3 | A-9 | A-22 | A-16 |
| 160 | R-3 | A-9 | A-22 | A-22 |
| 161 | R-3 | A-16 | A-1 | A-1 |
| 162 | R-3 | A-16 | A-1 | A-9 |
| 163 | R-3 | A-16 | A-1 | A-16 |
| 164 | R-3 | A-16 | A-1 | A-22 |
| 165 | R-3 | A-16 | A-9 | A-1 |
| 166 | R-3 | A-16 | A-9 | A-9 |
| 167 | R-3 | A-16 | A-9 | A-16 |
| 168 | R-3 | A-16 | A-9 | A-22 |
| 169 | R-3 | A-16 | A-16 | A-1 |
| 170 | R-3 | A-16 | A-16 | A-9 |
| 171 | R-3 | A-16 | A-16 | A-16 |
| 172 | R-3 | A-16 | A-16 | A-22 |
| 173 | R-3 | A-16 | A-22 | A-1 |
| 174 | R-3 | A-16 | A-22 | A-9 |
| 175 | R-3 | A-16 | A-22 | A-16 |
| 176 | R-3 | A-16 | A-22 | A-22 |
| 177 | R-3 | A-22 | A-1 | A-1 |
| 178 | R-3 | A-22 | A-1 | A-9 |
| 179 | R-3 | A-22 | A-1 | A-16 |
| 180 | R-3 | A-22 | A-1 | A-22 |
| 181 | R-3 | A-22 | A-9 | A-1 |
| 182 | R-3 | A-22 | A-9 | A-9 |
| 183 | R-3 | A-22 | A-9 | A-16 |
| 184 | R-3 | A-22 | A-9 | A-22 |
| 185 | R-3 | A-22 | A-16 | A-1 |
| 186 | R-3 | A-22 | A-16 | A-9 |
| 187 | R-3 | A-22 | A-16 | A-16 |
| 188 | R-3 | A-22 | A-16 | A-22 |
| 189 | R-3 | A-22 | A-22 | A-1 |
| 190 | R-3 | A-22 | A-22 | A-9 |
| 191 | R-3 | A-22 | A-22 | A-16 |
| 192 | R-3 | A-22 | A-22 | A-22 |
| 193 | R-4 | A-1 | A-1 | A-1 |
| 194 | R-4 | A-1 | A-1 | A-9 |
| 195 | R-4 | A-1 | A-1 | A-16 |
| 196 | R-4 | A-1 | A-1 | A-22 |
| 197 | R-4 | A-1 | A-9 | A-1 |
| 198 | R-4 | A-1 | A-9 | A-9 |
| 199 | R-4 | A-1 | A-9 | A-16 |
| 200 | R-4 | A-1 | A-9 | A-22 |
| 201 | R-4 | A-1 | A-16 | A-1 |
| 202 | R-4 | A-1 | A-16 | A-9 |
| 203 | R-4 | A-1 | A-16 | A-16 |
| 204 | R-4 | A-1 | A-16 | A-22 |
| 205 | R-4 | A-1 | A-22 | A-1 |
| 206 | R-4 | A-1 | A-22 | A-9 |
| 207 | R-4 | A-1 | A-22 | A-16 |
| 208 | R-4 | A-1 | A-22 | A-22 |
| 209 | R-4 | A-9 | A-1 | A-1 |
| 210 | R-4 | A-9 | A-1 | A-9 |
| 211 | R-4 | A-9 | A-1 | A-16 |
| 212 | R-4 | A-9 | A-1 | A-22 |
| 213 | R-4 | A-9 | A-9 | A-1 |
| 214 | R-4 | A-9 | A-9 | A-9 |
| 215 | R-4 | A-9 | A-9 | A-16 |
| 216 | R-4 | A-9 | A-9 | A-22 |
| 217 | R-4 | A-9 | A-16 | A-1 |
| 218 | R-4 | A-9 | A-16 | A-9 |
| 219 | R-4 | A-9 | A-16 | A-16 |
| 220 | R-4 | A-9 | A-16 | A-22 |
| 221 | R-4 | A-9 | A-22 | A-1 |

| | R¹ | A₁ | A₂ | A₃ |
|---|---|---|---|---|
| 222 | R-4 | A-9 | A-22 | A-9 |
| 223 | R-4 | A-9 | A-22 | A-16 |
| 224 | R-4 | A-9 | A-22 | A-22 |
| 225 | R-4 | A-16 | A-1 | A-1 |
| 226 | R-4 | A-16 | A-1 | A-9 |
| 227 | R-4 | A-16 | A-1 | A-16 |
| 228 | R-4 | A-16 | A-1 | A-22 |
| 229 | R-4 | A-16 | A-9 | A-1 |
| 230 | R-4 | A-16 | A-9 | A-9 |
| 231 | R-4 | A-16 | A-9 | A-16 |
| 232 | R-4 | A-16 | A-9 | A-22 |
| 233 | R-4 | A-16 | A-16 | A-1 |
| 234 | R-4 | A-16 | A-16 | A-9 |
| 235 | R-4 | A-16 | A-16 | A-16 |
| 236 | R-4 | A-16 | A-16 | A-22 |
| 237 | R-4 | A-16 | A-22 | A-1 |
| 238 | R-4 | A-16 | A-22 | A-9 |
| 239 | R-4 | A-16 | A-22 | A-16 |
| 240 | R-4 | A-16 | A-22 | A-22 |
| 241 | R-4 | A-22 | A-1 | A-1 |
| 242 | R-4 | A-22 | A-1 | A-9 |
| 243 | R-4 | A-22 | A-1 | A-16 |
| 244 | R-4 | A-22 | A-1 | A-22 |
| 245 | R-4 | A-22 | A-9 | A-1 |
| 246 | R-4 | A-22 | A-9 | A-9 |
| 247 | R-4 | A-22 | A-9 | A-16 |
| 248 | R-4 | A-22 | A-9 | A-22 |
| 249 | R-4 | A-22 | A-16 | A-1 |
| 250 | R-4 | A-22 | A-16 | A-9 |
| 251 | R-4 | A-22 | A-16 | A-16 |
| 252 | R-4 | A-22 | A-16 | A-22 |
| 253 | R-4 | A-22 | A-22 | A-1 |
| 254 | R-4 | A-22 | A-22 | A-9 |
| 255 | R-4 | A-22 | A-22 | A-16 |
| 256 | R-4 | A-22 | A-22 | A-22 |
| 257 | R-5 | A-1 | A-1 | A-1 |
| 258 | R-5 | A-1 | A-1 | A-9 |
| 259 | R-5 | A-1 | A-1 | A-16 |
| 260 | R-5 | A-1 | A-1 | A-22 |
| 261 | R-5 | A-1 | A-9 | A-1 |
| 262 | R-5 | A-1 | A-9 | A-9 |
| 263 | R-5 | A-1 | A-9 | A-16 |
| 264 | R-5 | A-1 | A-9 | A-22 |
| 265 | R-5 | A-1 | A-16 | A-1 |
| 266 | R-5 | A-1 | A-16 | A-9 |
| 267 | R-5 | A-1 | A-16 | A-16 |
| 268 | R-5 | A-1 | A-16 | A-22 |
| 269 | R-5 | A-1 | A-22 | A-1 |
| 270 | R-5 | A-1 | A-22 | A-9 |
| 271 | R-5 | A-1 | A-22 | A-16 |
| 272 | R-5 | A-1 | A-22 | A-22 |
| 273 | R-5 | A-9 | A-1 | A-1 |
| 274 | R-5 | A-9 | A-1 | A-9 |
| 275 | R-5 | A-9 | A-1 | A-16 |
| 276 | R-5 | A-9 | A-1 | A-22 |
| 277 | R-5 | A-9 | A-9 | A-1 |
| 278 | R-5 | A-9 | A-9 | A-9 |
| 279 | R-5 | A-9 | A-9 | A-16 |
| 280 | R-5 | A-9 | A-9 | A-22 |
| 281 | R-5 | A-9 | A-16 | A-1 |
| 282 | R-5 | A-9 | A-16 | A-9 |
| 283 | R-5 | A-9 | A-16 | A-16 |
| 284 | R-5 | A-9 | A-16 | A-22 |
| 285 | R-5 | A-9 | A-22 | A-1 |
| 286 | R-5 | A-9 | A-22 | A-9 |
| 287 | R-5 | A-9 | A-22 | A-16 |
| 288 | R-5 | A-9 | A-22 | A-22 |
| 289 | R-5 | A-16 | A-1 | A-1 |
| 290 | R-5 | A-16 | A-1 | A-9 |
| 291 | R-5 | A-16 | A-1 | A-16 |
| 292 | R-5 | A-16 | A-1 | A-22 |
| 293 | R-5 | A-16 | A-9 | A-1 |
| 294 | R-5 | A-16 | A-9 | A-9 |
| 295 | R-5 | A-16 | A-9 | A-16 |
| 296 | R-5 | A-16 | A-9 | A-22 |
| 297 | R-5 | A-16 | A-16 | A-1 |
| 298 | R-5 | A-16 | A-16 | A-9 |
| 299 | R-5 | A-16 | A-16 | A-16 |
| 300 | R-5 | A-16 | A-16 | A-22 |
| 301 | R-5 | A-16 | A-22 | A-1 |
| 302 | R-5 | A-16 | A-22 | A-9 |
| 303 | R-5 | A-16 | A-22 | A-16 |
| 304 | R-5 | A-16 | A-22 | A-22 |
| 305 | R-5 | A-22 | A-1 | A-1 |
| 306 | R-5 | A-22 | A-1 | A-9 |
| 307 | R-5 | A-22 | A-1 | A-16 |
| 308 | R-5 | A-22 | A-1 | A-22 |
| 309 | R-5 | A-22 | A-9 | A-1 |
| 310 | R-5 | A-22 | A-9 | A-9 |
| 311 | R-5 | A-22 | A-9 | A-16 |
| 312 | R-5 | A-22 | A-9 | A-22 |
| 313 | R-5 | A-22 | A-16 | A-1 |
| 314 | R-5 | A-22 | A-16 | A-9 |
| 315 | R-5 | A-22 | A-16 | A-16 |
| 316 | R-5 | A-22 | A-16 | A-22 |
| 317 | R-5 | A-22 | A-22 | A-1 |
| 318 | R-5 | A-22 | A-22 | A-9 |
| 319 | R-5 | A-22 | A-22 | A-16 |
| 320 | R-5 | A-22 | A-22 | A-22 |
| 321 | R-6 | A-1 | A-1 | A-1 |
| 322 | R-6 | A-1 | A-1 | A-9 |
| 323 | R-6 | A-1 | A-1 | A-16 |
| 324 | R-6 | A-1 | A-1 | A-22 |
| 325 | R-6 | A-1 | A-9 | A-1 |
| 326 | R-6 | A-1 | A-9 | A-9 |
| 327 | R-6 | A-1 | A-9 | A-16 |
| 328 | R-6 | A-1 | A-9 | A-22 |
| 329 | R-6 | A-1 | A-16 | A-1 |
| 330 | R-6 | A-1 | A-16 | A-9 |
| 331 | R-6 | A-1 | A-16 | A-16 |
| 332 | R-6 | A-1 | A-16 | A-22 |
| 333 | R-6 | A-1 | A-22 | A-1 |
| 334 | R-6 | A-1 | A-22 | A-9 |
| 335 | R-6 | A-1 | A-22 | A-16 |
| 336 | R-6 | A-1 | A-22 | A-22 |
| 337 | R-6 | A-9 | A-1 | A-1 |
| 338 | R-6 | A-9 | A-1 | A-9 |
| 339 | R-6 | A-9 | A-1 | A-16 |
| 340 | R-6 | A-9 | A-1 | A-22 |
| 341 | R-6 | A-9 | A-9 | A-1 |
| 342 | R-6 | A-9 | A-9 | A-9 |
| 343 | R-6 | A-9 | A-9 | A-16 |
| 344 | R-6 | A-9 | A-9 | A-22 |
| 345 | R-6 | A-9 | A-16 | A-1 |
| 346 | R-6 | A-9 | A-16 | A-9 |
| 347 | R-6 | A-9 | A-16 | A-16 |
| 348 | R-6 | A-9 | A-16 | A-22 |
| 349 | R-6 | A-9 | A-22 | A-1 |
| 350 | R-6 | A-9 | A-22 | A-9 |
| 351 | R-6 | A-9 | A-22 | A-16 |
| 352 | R-6 | A-9 | A-22 | A-22 |
| 353 | R-6 | A-16 | A-1 | A-1 |
| 354 | R-6 | A-16 | A-1 | A-9 |
| 355 | R-6 | A-16 | A-1 | A-16 |
| 356 | R-6 | A-16 | A-1 | A-22 |
| 357 | R-6 | A-16 | A-9 | A-1 |
| 358 | R-6 | A-16 | A-9 | A-9 |
| 359 | R-6 | A-16 | A-9 | A-16 |
| 360 | R-6 | A-16 | A-9 | A-22 |
| 361 | R-6 | A-16 | A-16 | A-1 |
| 362 | R-6 | A-16 | A-16 | A-9 |
| 363 | R-6 | A-16 | A-16 | A-16 |
| 364 | R-6 | A-16 | A-16 | A-22 |
| 365 | R-6 | A-16 | A-22 | A-1 |
| 366 | R-6 | A-16 | A-22 | A-9 |
| 367 | R-6 | A-16 | A-22 | A-16 |
| 368 | R-6 | A-16 | A-22 | A-22 |
| 369 | R-6 | A-22 | A-1 | A-1 |
| 370 | R-6 | A-22 | A-1 | A-9 |
| 371 | R-6 | A-22 | A-1 | A-16 |
| 372 | R-6 | A-22 | A-1 | A-22 |
| 373 | R-6 | A-22 | A-9 | A-1 |
| 374 | R-6 | A-22 | A-9 | A-9 |
| 375 | R-6 | A-22 | A-9 | A-16 |

| | R¹ | A₁ | A₂ | A₃ |
|---|---|---|---|---|
| 376 | R-6 | A-22 | A-9 | A-22 |
| 377 | R-6 | A-22 | A-16 | A-1 |
| 378 | R-6 | A-22 | A-16 | A-9 |
| 379 | R-6 | A-22 | A-16 | A-16 |
| 380 | R-6 | A-22 | A-16 | A-22 |
| 381 | R-6 | A-22 | A-22 | A-1 |
| 382 | R-6 | A-22 | A-22 | A-9 |
| 383 | R-6 | A-22 | A-22 | A-16 |
| 384 | R-6 | A-22 | A-22 | A-22 |
| 385 | R-7 | A-1 | A-1 | A-1 |
| 386 | R-7 | A-1 | A-1 | A-9 |
| 387 | R-7 | A-1 | A-1 | A-16 |
| 388 | R-7 | A-1 | A-1 | A-22 |
| 389 | R-7 | A-1 | A-9 | A-1 |
| 390 | R-7 | A-1 | A-9 | A-9 |
| 391 | R-7 | A-1 | A-9 | A-16 |
| 392 | R-7 | A-1 | A-9 | A-22 |
| 393 | R-7 | A-1 | A-16 | A-1 |
| 394 | R-7 | A-1 | A-16 | A-9 |
| 395 | R-7 | A-1 | A-16 | A-16 |
| 396 | R-7 | A-1 | A-16 | A-22 |
| 397 | R-7 | A-1 | A-22 | A-1 |
| 398 | R-7 | A-1 | A-22 | A-9 |
| 399 | R-7 | A-1 | A-22 | A-16 |
| 400 | R-7 | A-1 | A-22 | A-22 |
| 401 | R-7 | A-9 | A-1 | A-1 |
| 402 | R-7 | A-9 | A-1 | A-9 |
| 403 | R-7 | A-9 | A-1 | A-16 |
| 404 | R-7 | A-9 | A-1 | A-22 |
| 405 | R-7 | A-9 | A-9 | A-1 |
| 406 | R-7 | A-9 | A-9 | A-9 |
| 407 | R-7 | A-9 | A-9 | A-16 |
| 408 | R-7 | A-9 | A-9 | A-22 |
| 409 | R-7 | A-9 | A-16 | A-1 |
| 410 | R-7 | A-9 | A-16 | A-9 |
| 411 | R-7 | A-9 | A-16 | A-16 |
| 412 | R-7 | A-9 | A-16 | A-22 |
| 413 | R-7 | A-9 | A-22 | A-1 |
| 414 | R-7 | A-9 | A-22 | A-9 |
| 415 | R-7 | A-9 | A-22 | A-16 |
| 416 | R-7 | A-9 | A-22 | A-22 |
| 417 | R-7 | A-16 | A-1 | A-1 |
| 418 | R-7 | A-16 | A-1 | A-9 |
| 419 | R-7 | A-16 | A-1 | A-16 |
| 420 | R-7 | A-16 | A-1 | A-22 |
| 421 | R-7 | A-16 | A-9 | A-1 |
| 422 | R-7 | A-16 | A-9 | A-9 |
| 423 | R-7 | A-16 | A-9 | A-16 |
| 424 | R-7 | A-16 | A-9 | A-22 |
| 425 | R-7 | A-16 | A-16 | A-1 |
| 426 | R-7 | A-16 | A-16 | A-9 |
| 427 | R-7 | A-16 | A-16 | A-16 |
| 428 | R-7 | A-16 | A-16 | A-22 |
| 429 | R-7 | A-16 | A-22 | A-1 |
| 430 | R-7 | A-16 | A-22 | A-9 |
| 431 | R-7 | A-16 | A-22 | A-16 |
| 432 | R-7 | A-16 | A-22 | A-22 |
| 433 | R-7 | A-22 | A-1 | A-1 |
| 434 | R-7 | A-22 | A-1 | A-9 |
| 435 | R-7 | A-22 | A-1 | A-16 |
| 436 | R-7 | A-22 | A-1 | A-22 |
| 437 | R-7 | A-22 | A-9 | A-1 |
| 438 | R-7 | A-22 | A-9 | A-9 |
| 439 | R-7 | A-22 | A-9 | A-16 |
| 440 | R-7 | A-22 | A-9 | A-22 |
| 441 | R-7 | A-22 | A-16 | A-1 |
| 442 | R-7 | A-22 | A-16 | A-9 |
| 443 | R-7 | A-22 | A-16 | A-16 |
| 444 | R-7 | A-22 | A-16 | A-22 |
| 445 | R-7 | A-22 | A-22 | A-1 |
| 446 | R-7 | A-22 | A-22 | A-9 |
| 447 | R-7 | A-22 | A-22 | A-16 |
| 448 | R-7 | A-22 | A-22 | A-22 |
| 449 | R-8 | A-1 | A-1 | A-1 |
| 450 | R-8 | A-1 | A-1 | A-9 |
| 451 | R-8 | A-1 | A-1 | A-16 |
| 452 | R-8 | A-1 | A-1 | A-22 |
| 453 | R-8 | A-1 | A-9 | A-1 |
| 454 | R-8 | A-1 | A-9 | A-9 |
| 455 | R-8 | A-1 | A-9 | A-16 |
| 456 | R-8 | A-1 | A-9 | A-22 |
| 457 | R-8 | A-1 | A-16 | A-1 |
| 458 | R-8 | A-1 | A-16 | A-9 |
| 459 | R-8 | A-1 | A-16 | A-16 |
| 460 | R-8 | A-1 | A-16 | A-22 |
| 461 | R-8 | A-1 | A-22 | A-1 |
| 462 | R-8 | A-1 | A-22 | A-9 |
| 463 | R-8 | A-1 | A-22 | A-16 |
| 464 | R-8 | A-1 | A-22 | A-22 |
| 465 | R-8 | A-9 | A-1 | A-1 |
| 466 | R-8 | A-9 | A-1 | A-9 |
| 467 | R-8 | A-9 | A-1 | A-16 |
| 468 | R-8 | A-9 | A-1 | A-22 |
| 469 | R-8 | A-9 | A-9 | A-1 |
| 470 | R-8 | A-9 | A-9 | A-9 |
| 471 | R-8 | A-9 | A-9 | A-16 |
| 472 | R-8 | A-9 | A-9 | A-22 |
| 473 | R-8 | A-9 | A-16 | A-1 |
| 474 | R-8 | A-9 | A-16 | A-9 |
| 475 | R-8 | A-9 | A-16 | A-16 |
| 476 | R-8 | A-9 | A-16 | A-22 |
| 477 | R-8 | A-9 | A-22 | A-1 |
| 478 | R-8 | A-9 | A-22 | A-9 |
| 479 | R-8 | A-9 | A-22 | A-16 |
| 480 | R-8 | A-9 | A-22 | A-22 |
| 481 | R-8 | A-16 | A-1 | A-1 |
| 482 | R-8 | A-16 | A-1 | A-9 |
| 483 | R-8 | A-16 | A-1 | A-16 |
| 484 | R-8 | A-16 | A-1 | A-22 |
| 485 | R-8 | A-16 | A-9 | A-1 |
| 486 | R-8 | A-16 | A-9 | A-9 |
| 487 | R-8 | A-16 | A-9 | A-16 |
| 488 | R-8 | A-16 | A-9 | A-22 |
| 489 | R-8 | A-16 | A-16 | A-1 |
| 490 | R-8 | A-16 | A-16 | A-9 |
| 491 | R-8 | A-16 | A-16 | A-16 |
| 492 | R-8 | A-16 | A-16 | A-22 |
| 493 | R-8 | A-16 | A-22 | A-1 |
| 494 | R-8 | A-16 | A-22 | A-9 |
| 495 | R-8 | A-16 | A-22 | A-16 |
| 496 | R-8 | A-16 | A-22 | A-22 |
| 497 | R-8 | A-22 | A-1 | A-1 |
| 498 | R-8 | A-22 | A-1 | A-9 |
| 499 | R-8 | A-22 | A-1 | A-16 |
| 500 | R-8 | A-22 | A-1 | A-22 |
| 501 | R-8 | A-22 | A-9 | A-1 |
| 502 | R-8 | A-22 | A-9 | A-9 |
| 503 | R-8 | A-22 | A-9 | A-16 |
| 504 | R-8 | A-22 | A-9 | A-22 |
| 505 | R-8 | A-22 | A-16 | A-1 |
| 506 | R-8 | A-22 | A-16 | A-9 |
| 507 | R-8 | A-22 | A-16 | A-16 |
| 508 | R-8 | A-22 | A-16 | A-22 |
| 509 | R-8 | A-22 | A-22 | A-1 |
| 510 | R-8 | A-22 | A-22 | A-9 |
| 511 | R-8 | A-22 | A-22 | A-16 |
| 512 | R-8 | A-22 | A-22 | A-22 | where the groups $A_1$, $A_2$ and $A_3$ may each be substituted by one or more radicals $R^3$.

Explicit examples of compounds of the formula (I) are shown in the following table:

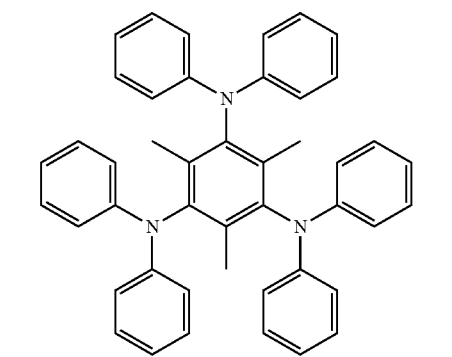 [SMILES: Cc1c(N(c2ccccc2)c2ccccc2)c(C)c(N(c2ccccc2)c2ccccc2)c(C)c1N(c1ccccc1)c1ccccc1]
1
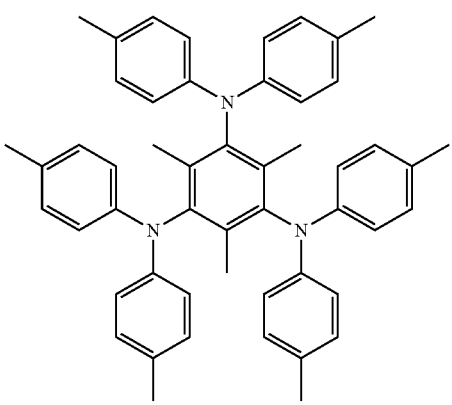
2
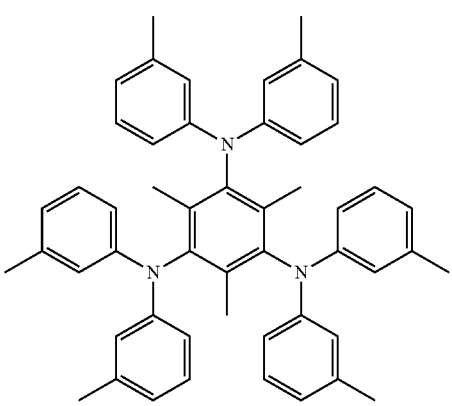
3
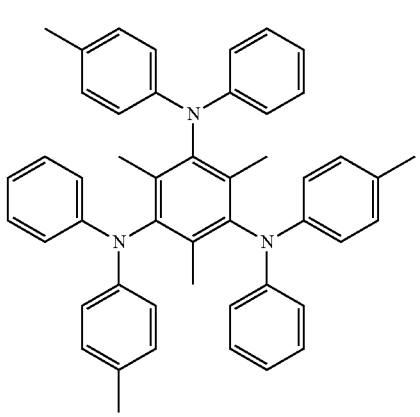 [SMILES: Cc1ccc(N(c2ccccc2)c2c(C)c(N(c3ccccc3)c3ccc(C)cc3)c(C)c(N(c3ccccc3)c3ccc(C)cc3)c2C)cc1]
4

-continued
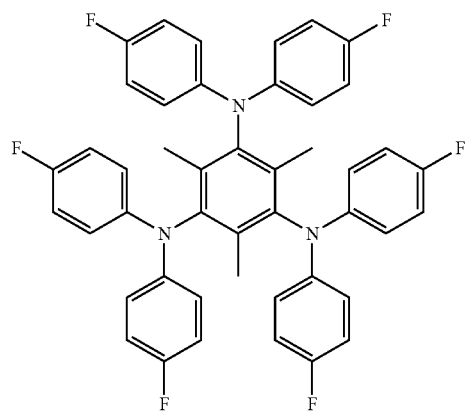 [SMILES: Cc1c(N(c2ccc(F)cc2)c2ccc(F)cc2)c(C)c(N(c2ccc(F)cc2)c2ccc(F)cc2)c(C)c1N(c1ccc(F)cc1)c1ccc(F)cc1]
5
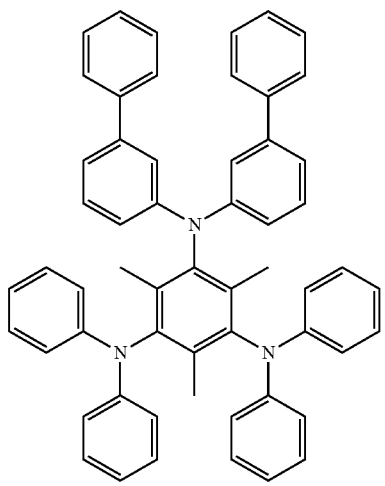 [SMILES: Cc1c(N(c2ccccc2)c2ccccc2)c(C)c(N(c2cccc(-c3ccccc3)c2)c2cccc(-c3ccccc3)c2)c(C)c1N(c1ccccc1)c1ccccc1]
6
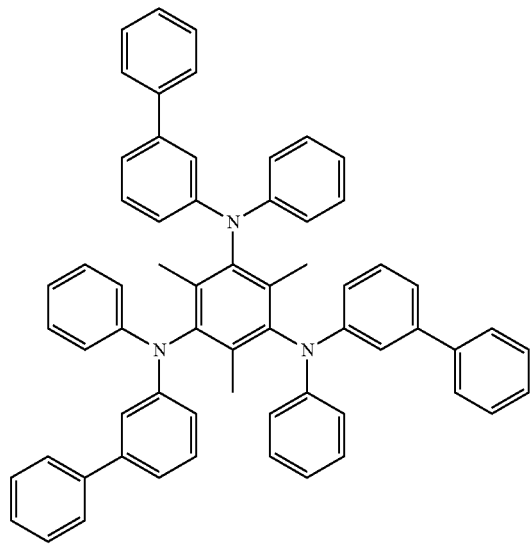 [SMILES: Cc1c(N(c2ccccc2)c2cccc(-c3ccccc3)c2)c(C)c(N(c2ccccc2)c2cccc(-c3ccccc3)c2)c(C)c1N(c1ccccc1)c1cccc(-c2ccccc2)c1]
7

8
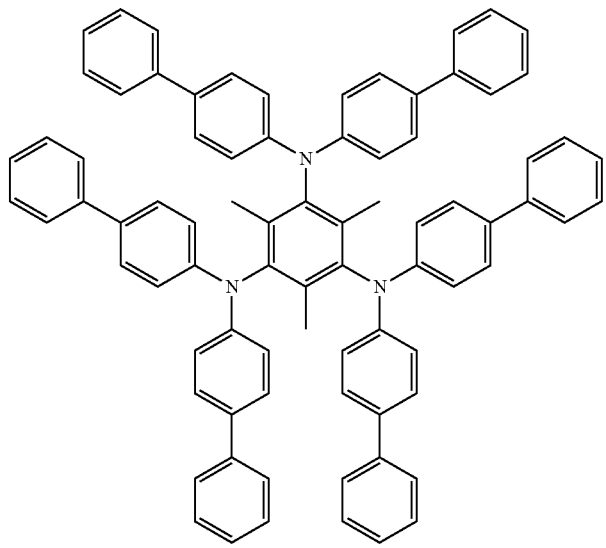 [SMILES: Cc1c(N(c2ccc(-c3ccccc3)cc2)c2ccc(-c3ccccc3)cc2)c(C)c(N(c2ccc(-c3ccccc3)cc2)c2ccc(-c3ccccc3)cc2)c(C)c1N(c1ccc(-c2ccccc2)cc1)c1ccc(-c2ccccc2)cc1]
9
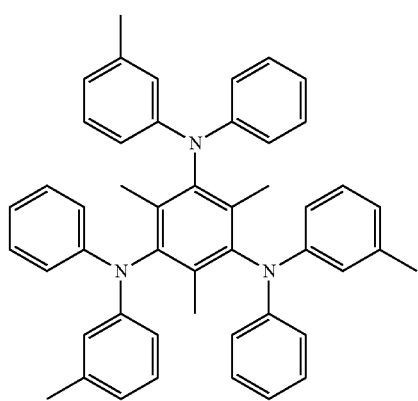 [SMILES: Cc1cccc(N(c2ccccc2)c2c(C)c(N(c3ccccc3)c3cccc(C)c3)c(C)c(N(c3ccccc3)c3cccc(C)c3)c2C)c1]
10
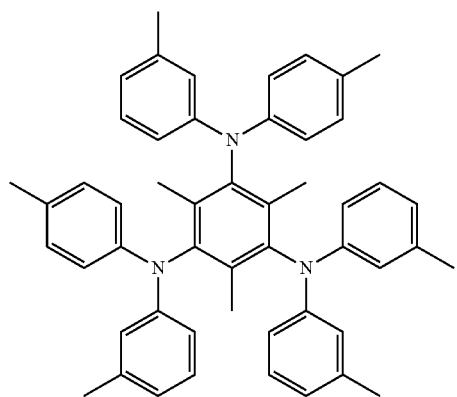

-continued
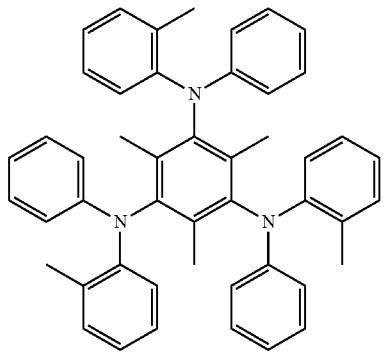 [SMILES: Cc1ccccc1N(c1ccccc1)c1c(C)c(N(c2ccccc2)c2ccccc2C)c(C)c(N(c2ccccc2)c2ccccc2C)c1C]
11
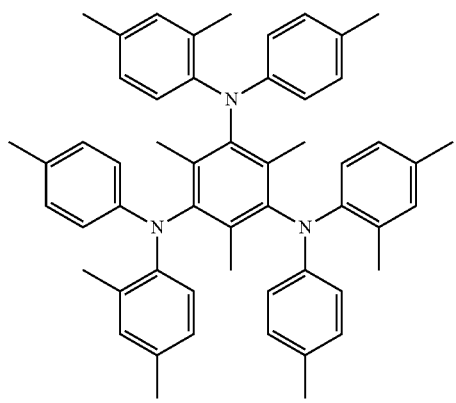
12
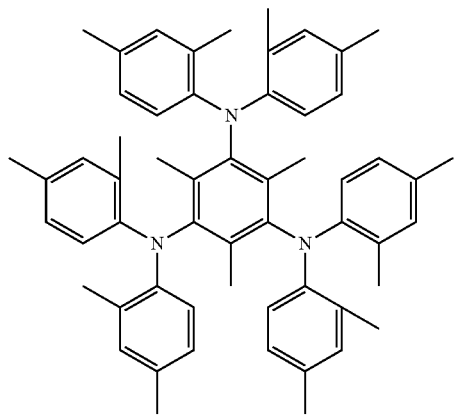
13
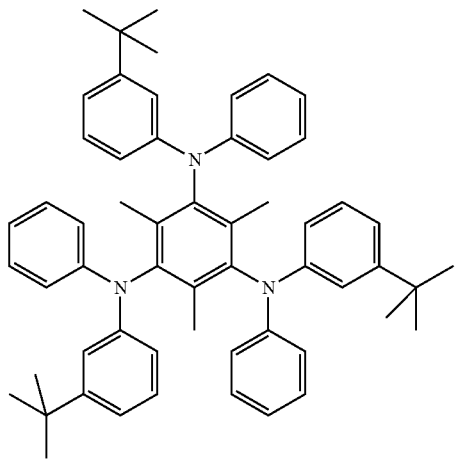 [SMILES: Cc1c(N(c2ccccc2)c2cccc(C(C)(C)C)c2)c(C)c(N(c2ccccc2)c2cccc(C(C)(C)C)c2)c(C)c1N(c1ccccc1)c1cccc(C(C)(C)C)c1]
14

-continued
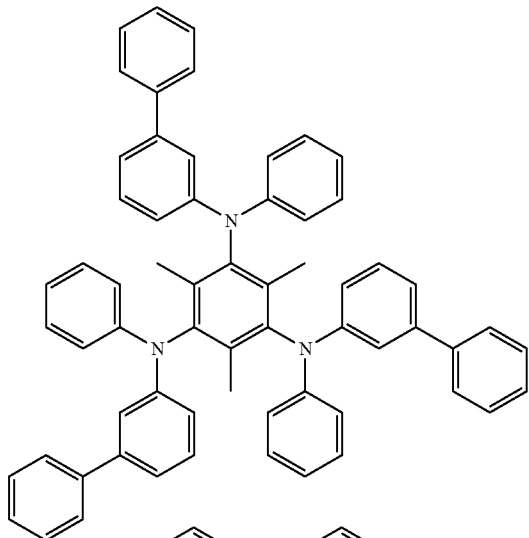
15
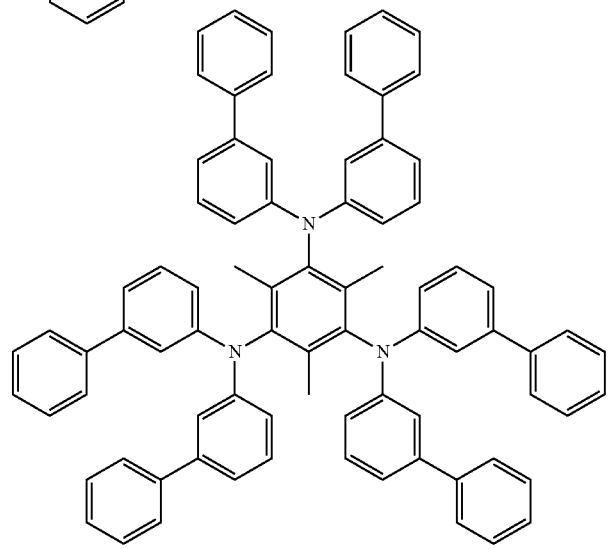
16
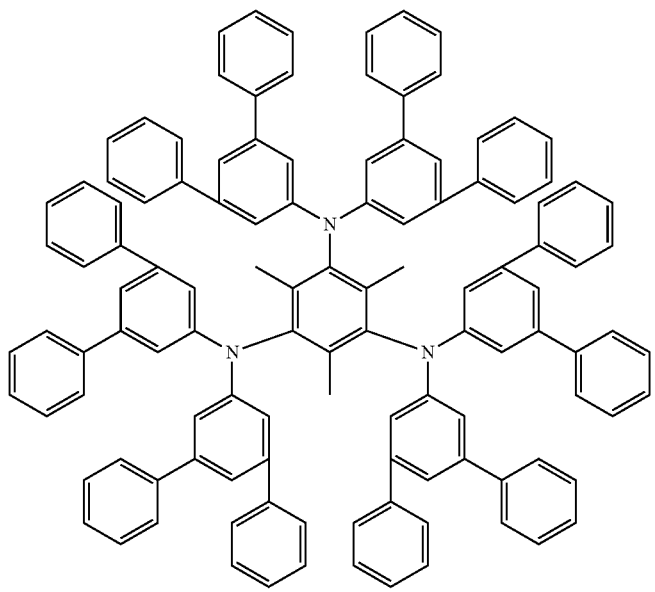 [SMILES: Cc1c(N(c2cc(-c3ccccc3)cc(-c3ccccc3)c2)c2cc(-c3ccccc3)cc(-c3ccccc3)c2)c(C)c(N(c2cc(-c3ccccc3)cc(-c3ccccc3)c2)c2cc(-c3ccccc3)cc(-c3ccccc3)c2)c(C)c1N(c1cc(-c2ccccc2)cc(-c2ccccc2)c1)c1cc(-c2ccccc2)cc(-c2ccccc2)c1]
17

-continued
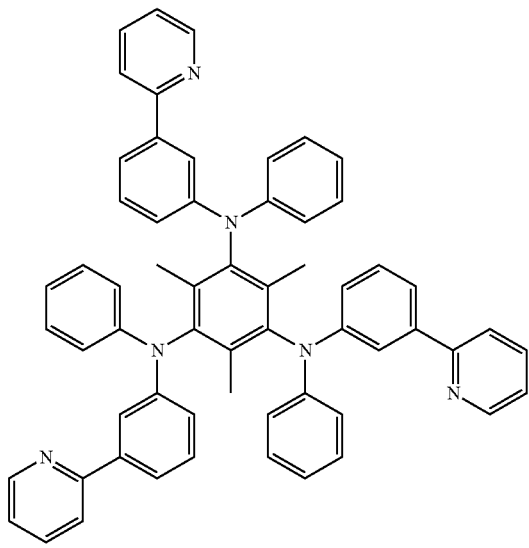 [SMILES: Cc1c(N(c2ccccc2)c2cccc(-c3ccccn3)c2)c(C)c(N(c2ccccc2)c2cccc(-c3ccccn3)c2)c(C)c1N(c1ccccc1)c1cccc(-c2ccccn2)c1]
18
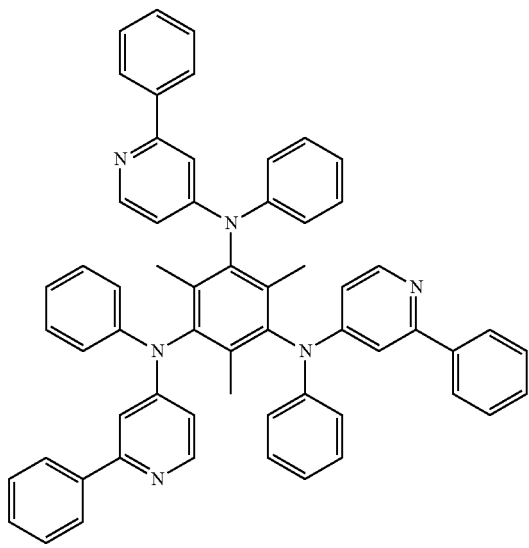 [SMILES: Cc1c(N(c2ccccc2)c2ccnc(-c3ccccc3)c2)c(C)c(N(c2ccccc2)c2ccnc(-c3ccccc3)c2)c(C)c1N(c1ccccc1)c1ccnc(-c2ccccc2)c1]
19
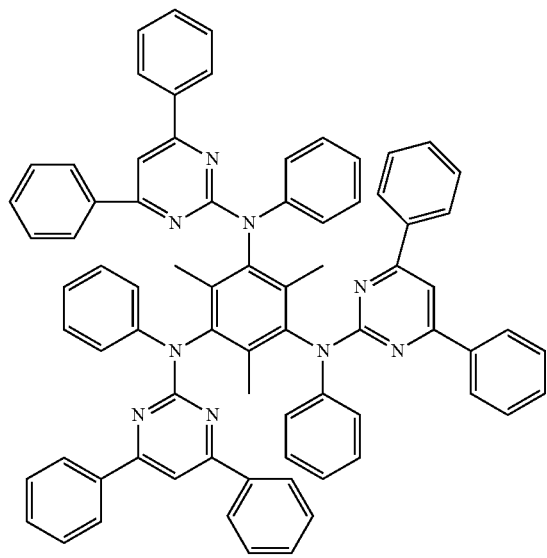 [SMILES: Cc1c(N(c2ccccc2)c2nc(-c3ccccc3)cc(-c3ccccc3)n2)c(C)c(N(c2ccccc2)c2nc(-c3ccccc3)cc(-c3ccccc3)n2)c(C)c1N(c1ccccc1)c1nc(-c2ccccc2)cc(-c2ccccc2)n1]
20

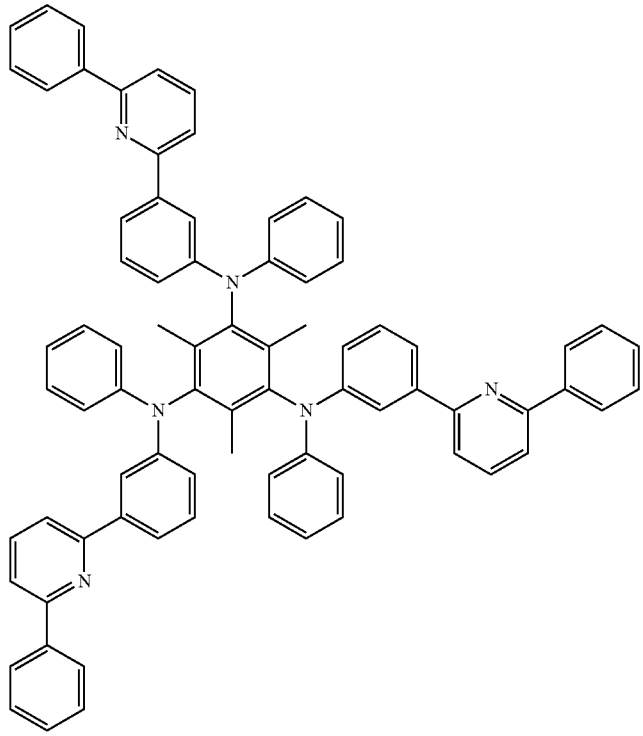 [SMILES: Cc1c(N(c2ccccc2)c2cccc(-c3cccc(-c4ccccc4)n3)c2)c(C)c(N(c2ccccc2)c2cccc(-c3cccc(-c4ccccc4)n3)c2)c(C)c1N(c1ccccc1)c1cccc(-c2cccc(-c3ccccc3)n2)c1]
21
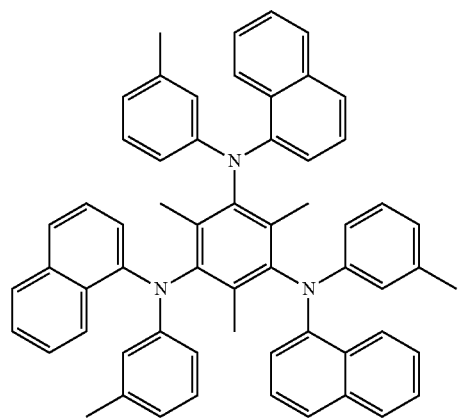 [SMILES: Cc1cccc(N(c2c(C)c(N(c3cccc(C)c3)c3cccc4ccccc34)c(C)c(N(c3cccc(C)c3)c3cccc4ccccc34)c2C)c2cccc3ccccc23)c1]
22
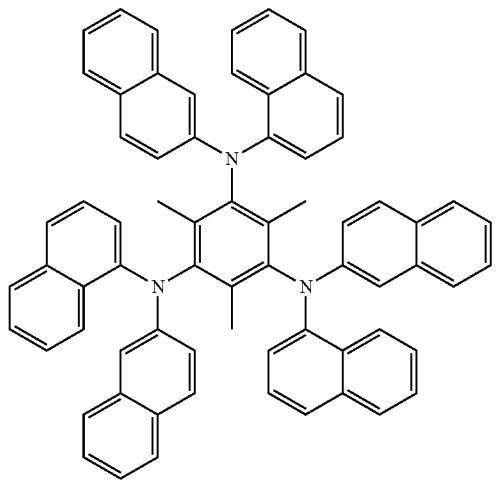 [SMILES: Cc1c(N(c2ccc3ccccc3c2)c2cccc3ccccc23)c(C)c(N(c2ccc3ccccc3c2)c2cccc3ccccc23)c(C)c1N(c1ccc2ccccc2c1)c1cccc2ccccc12]
23

24
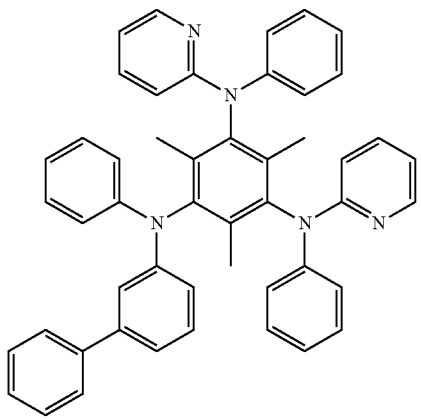 [SMILES: Cc1c(N(c2ccccc2)c2cccc(-c3ccccc3)c2)c(C)c(N(c2ccccc2)c2ccccn2)c(C)c1N(c1ccccc1)c1ccccn1]
25
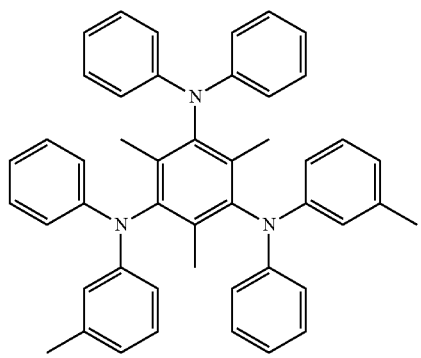 [SMILES: Cc1cccc(N(c2ccccc2)c2c(C)c(N(c3ccccc3)c3ccccc3)c(C)c(N(c3ccccc3)c3cccc(C)c3)c2C)c1]
26
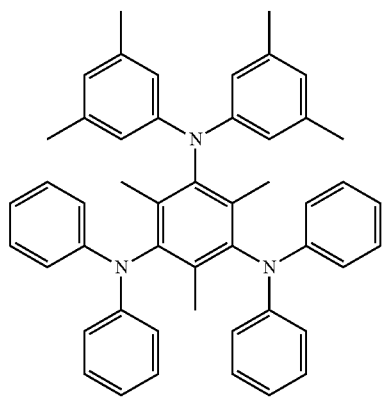 [SMILES: Cc1cc(C)cc(N(c2cc(C)cc(C)c2)c2c(C)c(N(c3ccccc3)c3ccccc3)c(C)c(N(c3ccccc3)c3ccccc3)c2C)c1]
27
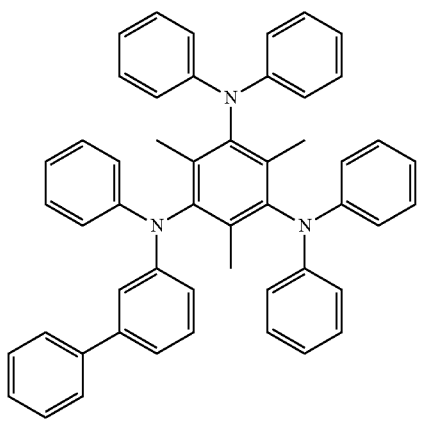 [SMILES: Cc1c(N(c2ccccc2)c2ccccc2)c(C)c(N(c2ccccc2)c2cccc(-c3ccccc3)c2)c(C)c1N(c1ccccc1)c1ccccc1]

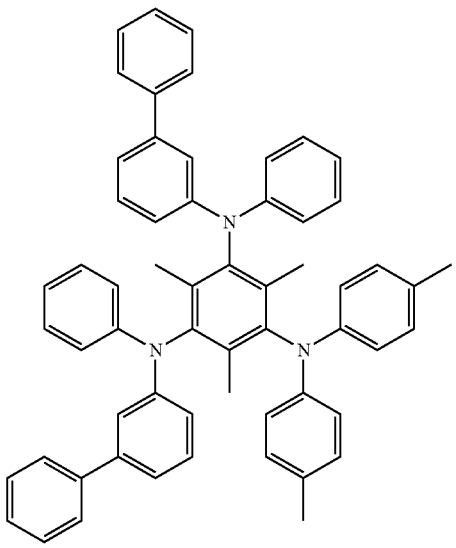 [SMILES: Cc1ccc(N(c2ccc(C)cc2)c2c(C)c(N(c3ccccc3)c3cccc(-c4ccccc4)c3)c(C)c(N(c3ccccc3)c3cccc(-c4ccccc4)c3)c2C)cc1]
28
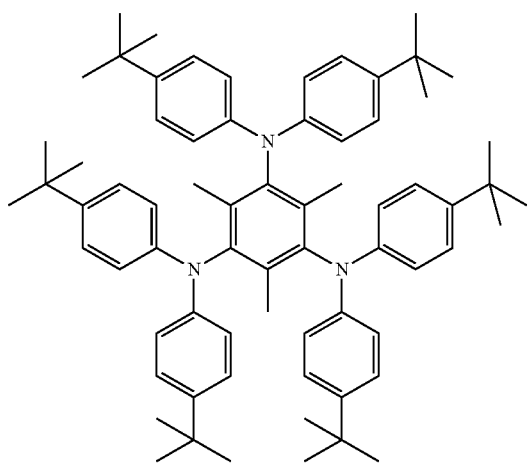 [SMILES: Cc1c(N(c2ccc(C(C)(C)C)cc2)c2ccc(C(C)(C)C)cc2)c(C)c(N(c2ccc(C(C)(C)C)cc2)c2ccc(C(C)(C)C)cc2)c(C)c1N(c1ccc(C(C)(C)C)cc1)c1ccc(C(C)(C)C)cc1]
29
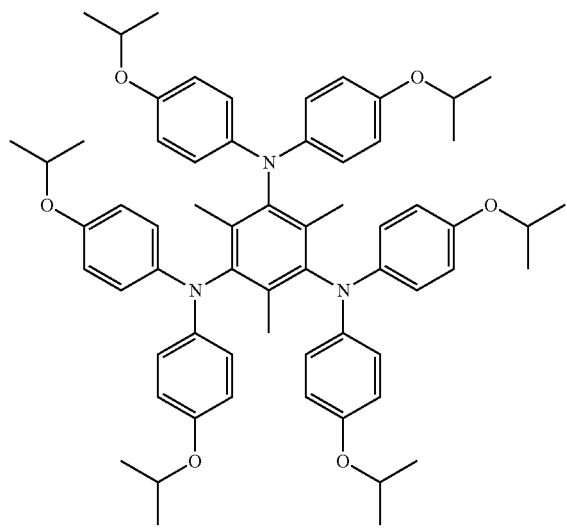 [SMILES: Cc1c(N(c2ccc(OC(C)C)cc2)c2ccc(OC(C)C)cc2)c(C)c(N(c2ccc(OC(C)C)cc2)c2ccc(OC(C)C)cc2)c(C)c1N(c1ccc(OC(C)C)cc1)c1ccc(OC(C)C)cc1]
30

-continued
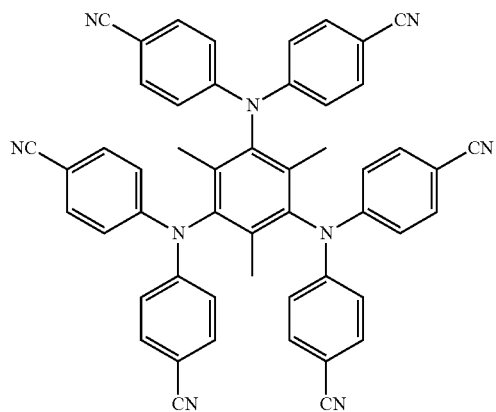 [SMILES: Cc1c(N(c2ccc(C#N)cc2)c2ccc(C#N)cc2)c(C)c(N(c2ccc(C#N)cc2)c2ccc(C#N)cc2)c(C)c1N(c1ccc(C#N)cc1)c1ccc(C#N)cc1]
31
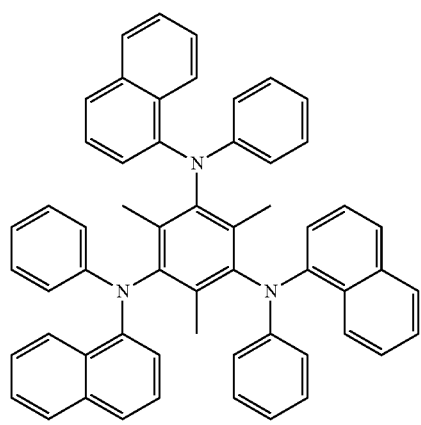 [SMILES: Cc1c(N(c2ccccc2)c2cccc3ccccc23)c(C)c(N(c2ccccc2)c2cccc3ccccc23)c(C)c1N(c1ccccc1)c1cccc2ccccc12]
32
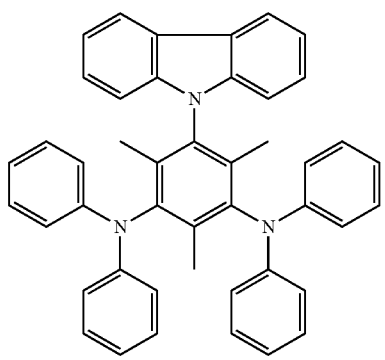 [SMILES: Cc1c(N(c2ccccc2)c2ccccc2)c(C)c(-n2c3ccccc3c3ccccc32)c(C)c1N(c1ccccc1)c1ccccc1]
33
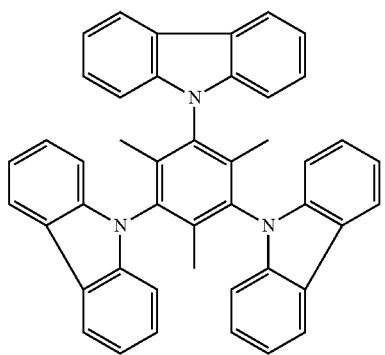 [SMILES: Cc1c(-n2c3ccccc3c3ccccc32)c(C)c(-n2c3ccccc3c3ccccc32)c(C)c1-n1c2ccccc2c2ccccc21]
34

-continued
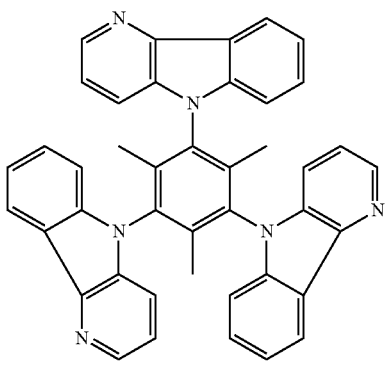 [SMILES: Cc1c(-n2c3ccccc3c3ncccc32)c(C)c(-n2c3ccccc3c3ncccc32)c(C)c1-n1c2ccccc2c2ncccc21]
35
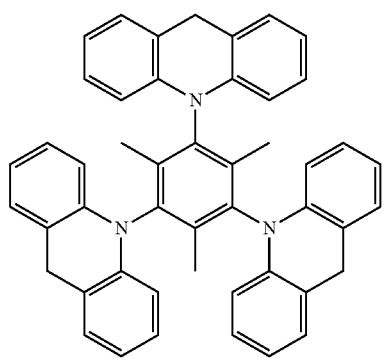 [SMILES: Cc1c(N2c3ccccc3Cc3ccccc32)c(C)c(N2c3ccccc3Cc3ccccc32)c(C)c1N1c2ccccc2Cc2ccccc21]
36
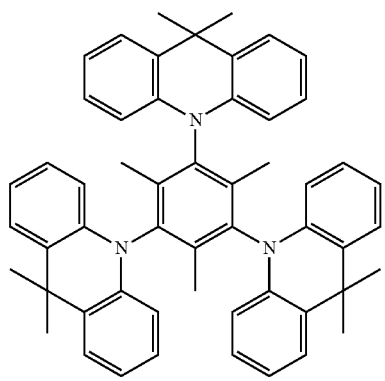 [SMILES: Cc1c(N2c3ccccc3C(C)(C)c3ccccc32)c(C)c(N2c3ccccc3C(C)(C)c3ccccc32)c(C)c1N1c2ccccc2C(C)(C)c2ccccc21]
37
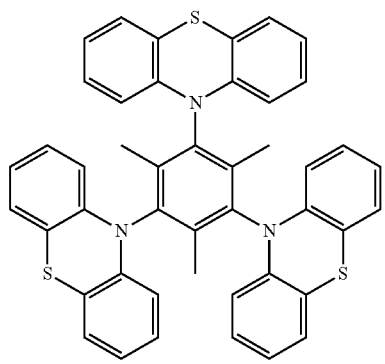
38

39
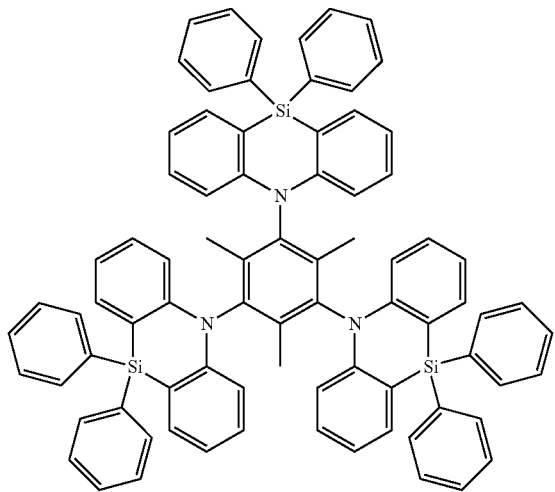 [SMILES: Cc1c(N2c3ccccc3[Si](c3ccccc3)(c3ccccc3)c3ccccc32)c(C)c(N2c3ccccc3[Si](c3ccccc3)(c3ccccc3)c3ccccc32)c(C)c1N1c2ccccc2[Si](c2ccccc2)(c2ccccc2)c2ccccc21]
40
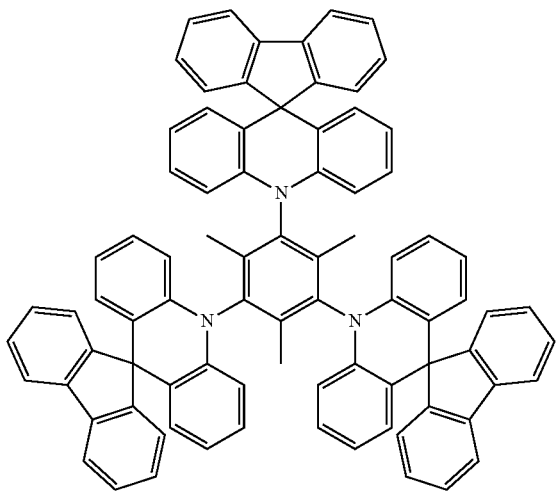 [SMILES: Cc1c(N2c3ccccc3C3(c4ccccc4-c4ccccc43)c3ccccc32)c(C)c(N2c3ccccc3C3(c4ccccc4-c4ccccc43)c3ccccc32)c(C)c1N1c2ccccc2C2(c3ccccc3-c3ccccc32)c2ccccc21]
41
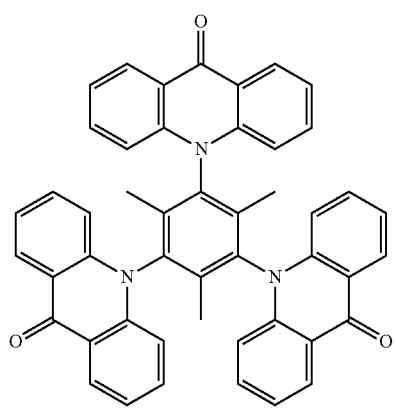 [SMILES: Cc1c(-n2c3ccccc3c(=O)c3ccccc32)c(C)c(-n2c3ccccc3c(=O)c3ccccc32)c(C)c1-n1c2ccccc2c(=O)c2ccccc21]

-continued
42
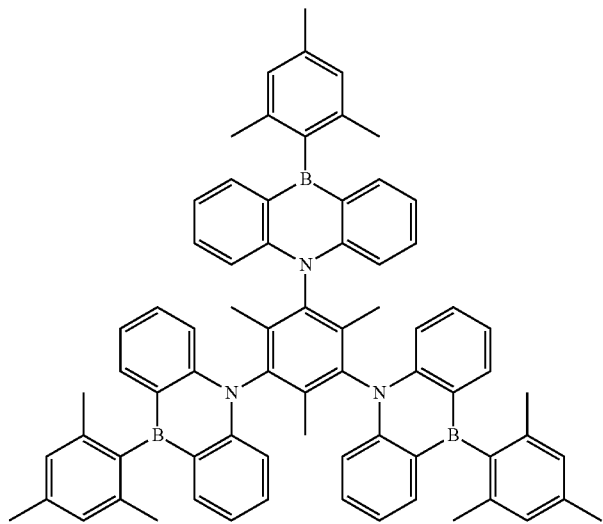
43
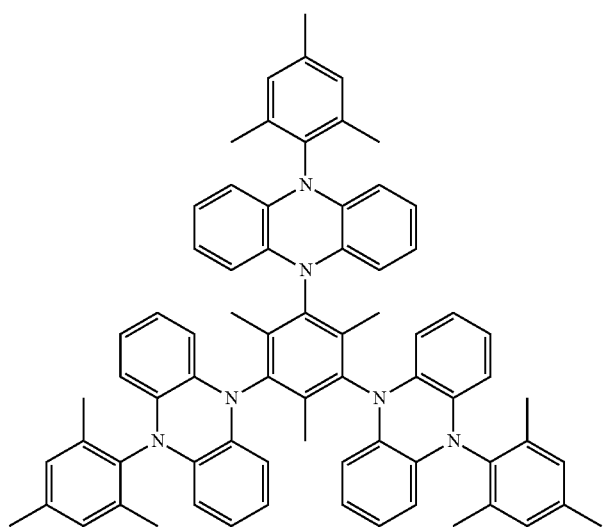
44
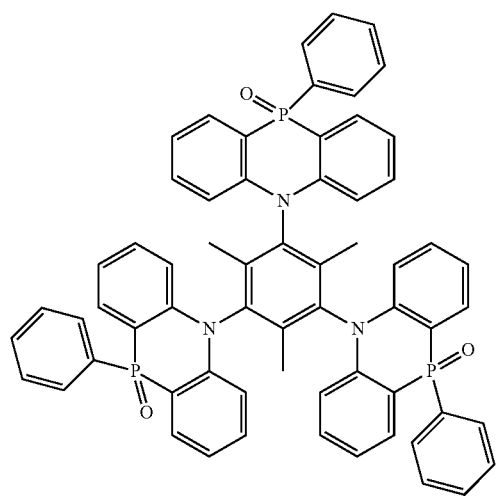 [SMILES: Cc1c(N2c3ccccc3P(=O)(c3ccccc3)c3ccccc32)c(C)c(N2c3ccccc3P(=O)(c3ccccc3)c3ccccc32)c(C)c1N1c2ccccc2P(=O)(c2ccccc2)c2ccccc21]

45
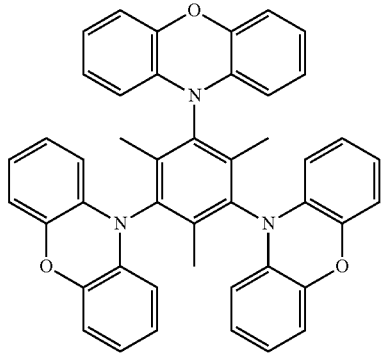
46
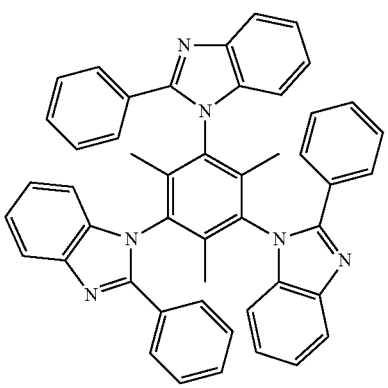 [SMILES: Cc1c(-n2c(-c3ccccc3)nc3ccccc32)c(C)c(-n2c(-c3ccccc3)nc3ccccc32)c(C)c1-n1c(-c2ccccc2)nc2ccccc21]
47
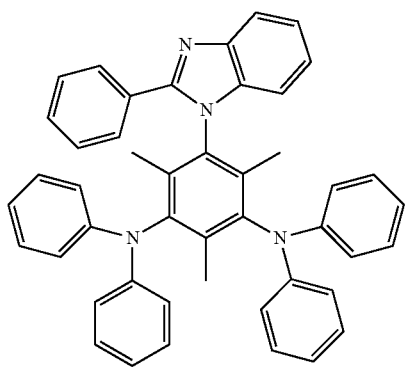 [SMILES: Cc1c(N(c2ccccc2)c2ccccc2)c(C)c(-n2c(-c3ccccc3)nc3ccccc32)c(C)c1N(c1ccccc1)c1ccccc1]
48
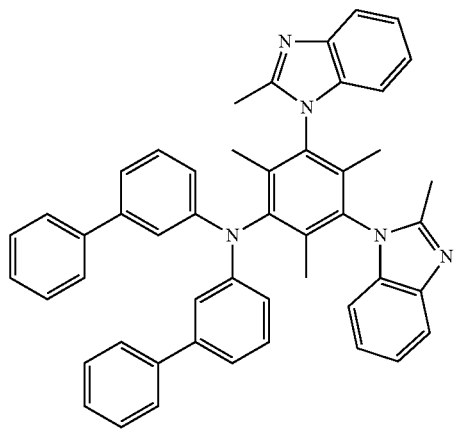 [SMILES: Cc1c(N(c2cccc(-c3ccccc3)c2)c2cccc(-c3ccccc3)c2)c(C)c(-n2c(C)nc3ccccc32)c(C)c1-n1c(C)nc2ccccc21]

-continued
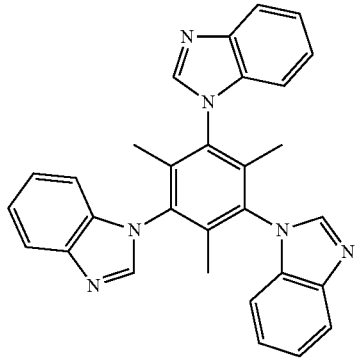 [SMILES: Cc1c(-n2cnc3ccccc32)c(C)c(-n2cnc3ccccc32)c(C)c1-n1cnc2ccccc21]
49
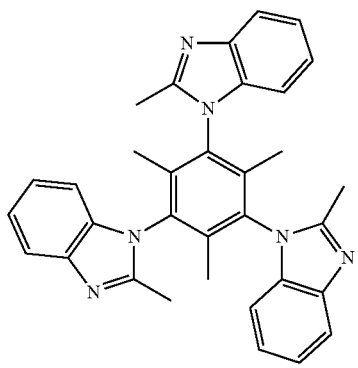 [SMILES: Cc1c(-n2c(C)nc3ccccc32)c(C)c(-n2c(C)nc3ccccc32)c(C)c1-n1c(C)nc2ccccc21]
50
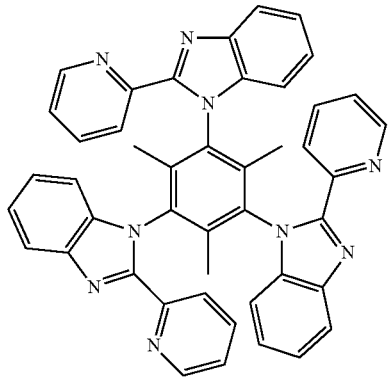 [SMILES: Cc1c(-n2c(-c3ccccn3)nc3ccccc32)c(C)c(-n2c(-c3ccccn3)nc3ccccc32)c(C)c1-n1c(-c2ccccn2)nc2ccccc21]
51
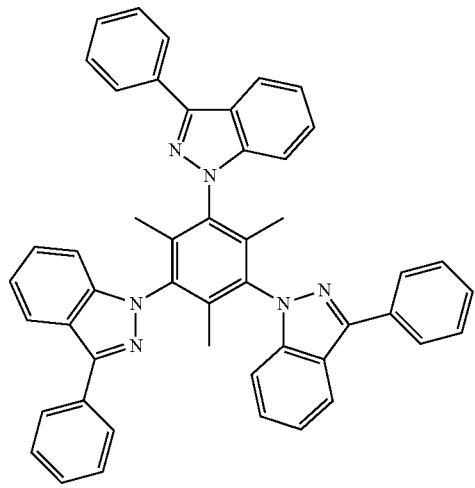 [SMILES: Cc1c(-n2nc(-c3ccccc3)c3ccccc32)c(C)c(-n2nc(-c3ccccc3)c3ccccc32)c(C)c1-n1nc(-c2ccccc2)c2ccccc21]
52

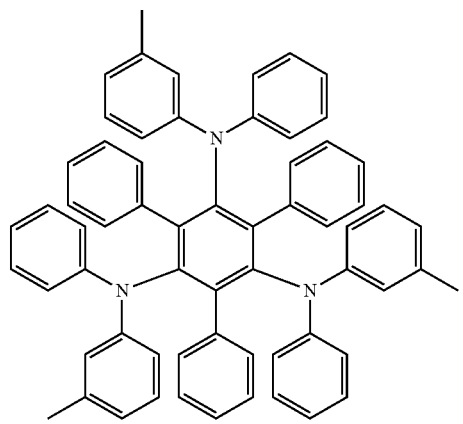 [SMILES: Cc1cccc(N(c2ccccc2)c2c(-c3ccccc3)c(N(c3ccccc3)c3cccc(C)c3)c(-c3ccccc3)c(N(c3ccccc3)c3cccc(C)c3)c2-c2ccccc2)c1]
53
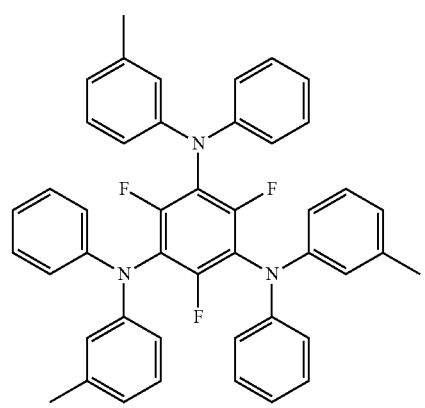 [SMILES: Cc1cccc(N(c2ccccc2)c2c(F)c(N(c3ccccc3)c3cccc(C)c3)c(F)c(N(c3ccccc3)c3cccc(C)c3)c2F)c1]
54
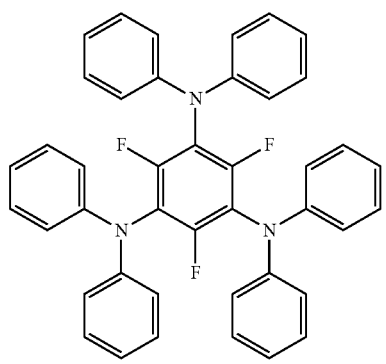 [SMILES: Fc1c(N(c2ccccc2)c2ccccc2)c(F)c(N(c2ccccc2)c2ccccc2)c(F)c1N(c1ccccc1)c1ccccc1]
55
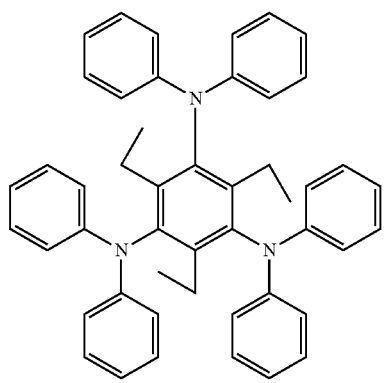 [SMILES: CCc1c(N(c2ccccc2)c2ccccc2)c(CC)c(N(c2ccccc2)c2ccccc2)c(CC)c1N(c1ccccc1)c1ccccc1]
56

-continued
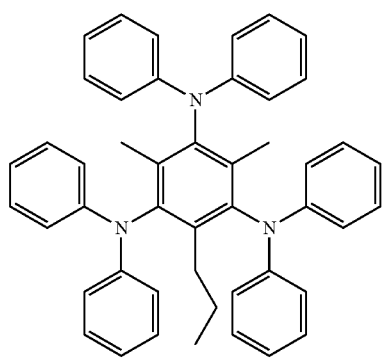 [SMILES: CCCc1c(N(c2ccccc2)c2ccccc2)c(C)c(N(c2ccccc2)c2ccccc2)c(C)c1N(c1ccccc1)c1ccccc1]
57
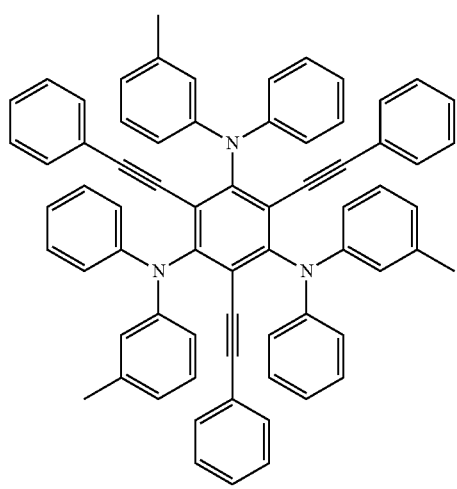 [SMILES: Cc1cccc(N(c2ccccc2)c2c(C#Cc3ccccc3)c(N(c3ccccc3)c3cccc(C)c3)c(C#Cc3ccccc3)c(N(c3ccccc3)c3cccc(C)c3)c2C#Cc2ccccc2)c1]
58
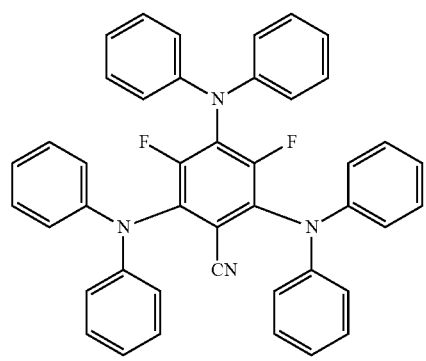 [SMILES: N#Cc1c(N(c2ccccc2)c2ccccc2)c(F)c(N(c2ccccc2)c2ccccc2)c(F)c1N(c1ccccc1)c1ccccc1]
59
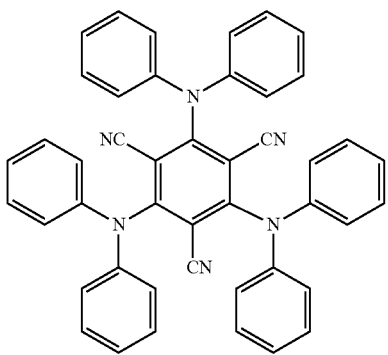 [SMILES: N#Cc1c(N(c2ccccc2)c2ccccc2)c(C#N)c(N(c2ccccc2)c2ccccc2)c(C#N)c1N(c1ccccc1)c1ccccc1]
60

The compounds according to the invention can be prepared by known organochemical synthetic methods. These include, for example, Ullmann coupling, Hartwig-Buchwald coupling, Suzuki coupling and halogenation reactions.

In accordance with Scheme 1 below, the compounds according to the invention can be obtained by Pd-catalysed coupling (Buchwald coupling) or copper-catalysed coupling (Ullmann coupling) of 1,3,5-tribromo-substituted benzenes which are substituted by radicals R in positions 2, 4 and 6 to aromatic or heteroaromatic secondary amines or heterocycles having an NH function. The multiplicity of aromatic or heteroaromatic secondary amines or heterocycles having an NH function which are known from the literature, such as, for example, pyrroles, indoles, pyrazoles, imidazoles, benzimidazoles, carbazoles, azacarbazoles, phenoxazines, phenothiazines, and others can be employed here.

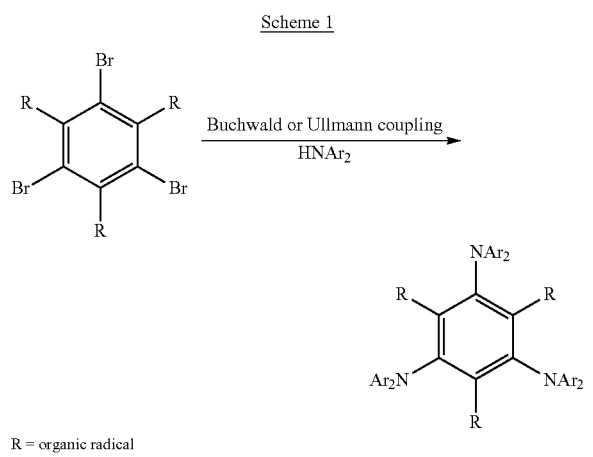

The amination reaction can also be carried out in two steps, as shown in Scheme 2.

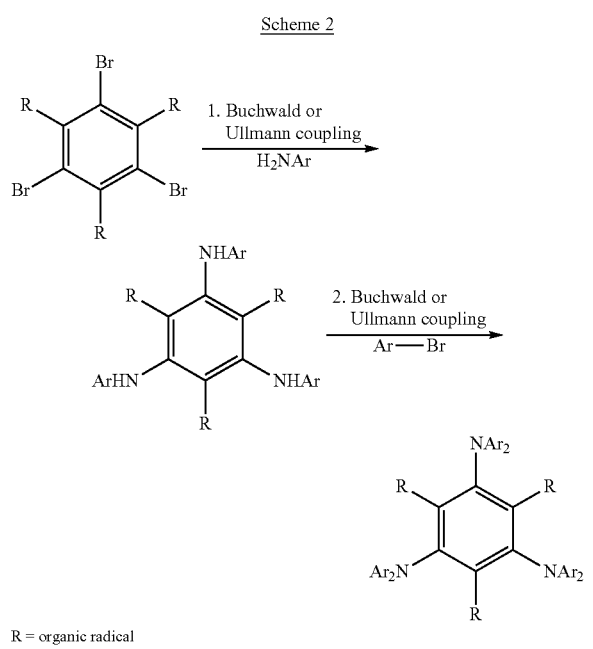

Through the use of 1,3,5-trihalogen-substituted benzenes which carry different halogens, compounds according to the invention which are asymmetrical with respect to the amine functionality can be obtained by carrying out two amination reactions sequentially with in each case different amines (see Scheme 3).

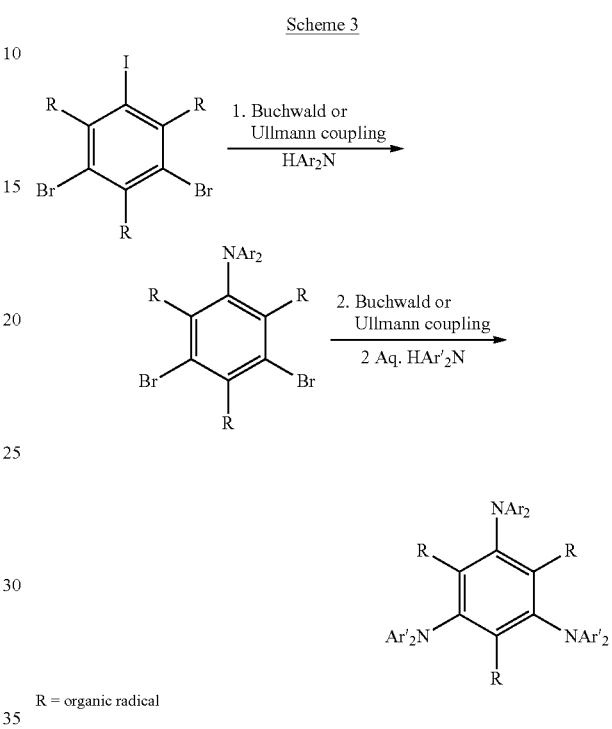

Suitable starting materials for this purpose are, for example:

1,3-dibromo-5-iodo-2,4,6-trimethylbenzene [1208325-27-2]

1,3-dichloro-5-iodo-2,4,6-trimethylbenzene [182119-63-7]

1-bromo-3,5-diiodo-1,3,5-trimethylbenzene [124312-45-4]

1-chloro-3,5-diiodo-1,3,5-trimethylbenzene [41571-69-1]

Substituents other than methyl may also be present analogously in positions 2, 4 and 6.

It is furthermore possible to functionalise further the compounds obtained from the reactions shown above. Scheme 4 shows an illustrative example of this. Thus, the arylamino compound according to the invention can be brominated using NBS, preferably in the para-position to the nitrogen. As many equivalents of NBS as free para-positions are present are preferably used here. The bromine functions introduced can then be reacted further in a second step by conventional methods, for example in amination reactions, Suzuki, Negishi, Yamamoto, Sonogashira, Grignard cross-couplings, Pd-catalysed boranylations, etherifications, cyanations, silylations, etc., to mention but a few. A reaction to give oligomers, polymers or dendrimers may also take place here. Scheme 3 shows by way of example a Buchwald amination and a Suzuki aryl coupling.

Scheme 4

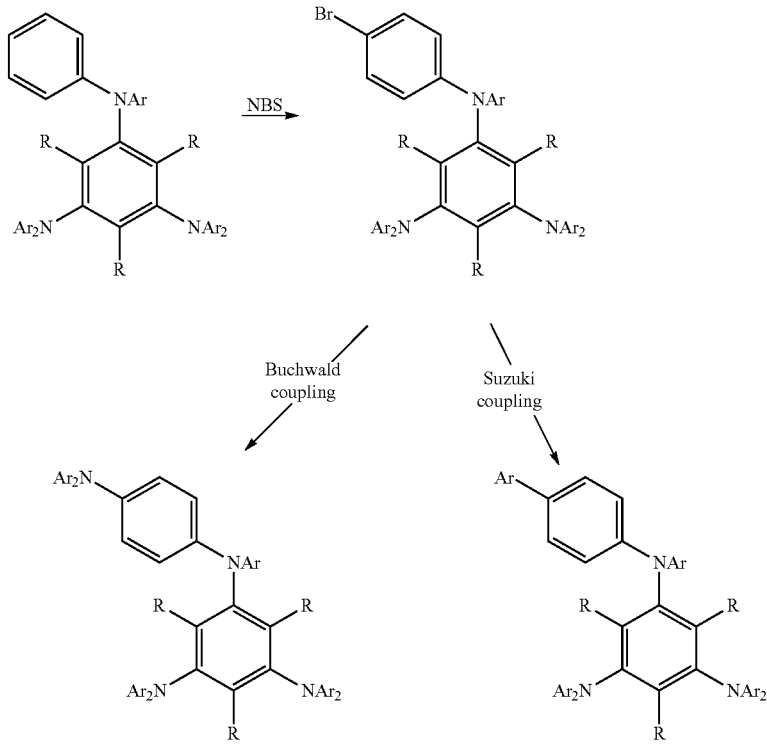

The invention thus furthermore relates to a process for the preparation of a compound of the formula (I), characterised in that at least one intermediate of a formula (Z)

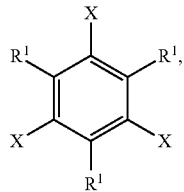

formula (Z)

where $R^1$ is defined as in connection with formula (I), and where
X represents, identically or differently, any desired reactive group, for example Cl, Br, I, boronic acid, boronic acid ester or sulfonic acid ester groups,
is reacted with at least one arylamino compound or at least one heterocyclic compound containing at least one NH function.

The compounds according to the invention described above, in particular compounds which are substituted by reactive leaving groups, can be used as monomers for the preparation of corresponding oligomers, dendrimers or polymers. Suitable reactive leaving groups are, for example, bromine; iodine; chlorine; boronic acids; boronic acid esters; amines; alkenyl or alkynyl groups having a terminal C=C double bond or C—C triple bond; oxiranes; oxetanes; groups which undergo a cycloaddition, for example a 1,3-dipolar cycloaddition, such as, for example, dienes or azides; carboxylic acid derivatives; alcohols and silanes.

The invention therefore furthermore relates to oligomers, polymers or dendrimers containing one or more compounds of the formula (I), where the bond(s) to the polymer, oligomer or dendrimer can be localised at any desired positions in formula (I) which are substituted by $R^1$, $R^2$ or $R^3$. Depending on the linking of the compound of the formula (I), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) may be linked via a trivalent or polyvalent group, for example via a trivalent or polyvalent aromatic or heteroaromatic group, to form a branched or dendritic oligomer or polymer. The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/

22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, of which at least one monomer results in recurring units of the formula (I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds of the formula (I) from liquid phase, for example by spin coating or by printing processes, formulations of the compounds are necessary. These formulations can be, for example, solutions, dispersions or mini-emulsions.

The invention therefore furthermore relates to a formulation, in particular a solution, dispersion or mini-emulsion, comprising at least one compound of the formula (I) or at least one polymer, oligomer or dendrimer containing at least one unit of the formula (I) and at least one solvent, preferably an organic solvent. The way in which solutions of this type can be prepared is known to the person skilled in the art and is described, for example, in the applications WO 2002/072714 and WO 2003/019694 and the literature cited therein.

The compounds of the formula (I) are suitable for use in electronic devices, in particular in organic electroluminescent devices (OLEDs). The compounds can be employed in different functions and/or layers, inter alia depending on the substitution. The compounds are preferably employed as hole-transport materials in a hole-transporting layer, as matrix materials in an emitting layer, as electron-blocking materials and as exciton-blocking materials.

The invention furthermore relates to the use of the compounds of the formula (I) in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably selected from organic electroluminescent devices (OLEDs).

The invention furthermore relates to an electronic device comprising anode, cathode and at least one organic layer, where the organic layer comprises at least one compound of the formula (I). The electronic device here is preferably selected from the above-mentioned devices and is particularly preferably an organic electroluminescent device (OLED).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), coupling-out layers and/or organic or inorganic p/n junctions. However, it should be pointed out that each of these layers does not necessarily have to be present and the choice of layers is always dependent on the compounds used and in particular also on whether the electroluminescent device is fluorescent or phosphorescent. The compounds preferably employed in the respective layers and functions are explicitly disclosed in later sections.

It is preferred in accordance with the invention for the compound of the formula (I) to be employed in an electronic device comprising one or more phosphorescent dopants. The compound can be used in various layers here, preferably in an electron-transport layer, a hole-transport layer, a hole-injection layer or in the emitting layer. However, the compound of the formula (I) can also be employed in accordance with the invention in an electronic device comprising one or more fluorescent dopants and no phosphorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs. Further examples of suitable phosphorescent dopants are revealed by the table following in a later section.

In a preferred embodiment of the present invention, the compounds of the formula (I) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (I) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. The two different matrix materials here may be present in a ratio of 1:50 to 1:1, preferably 1:20 to 1:1, particularly preferably 1:10 to 1:1 and very particularly preferably 1:4 to 1:1.

Mixed-matrix systems are preferably employed in phosphorescent organic electroluminescent devices. More detailed information of mixed-matrix systems is given, inter alia, in the application WO 2010/108579.

The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Particularly suitable matrix materials, which can be employed in combination with the compounds according to the invention as matrix components of a mixed-matrix system, are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazoie derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or indenocarbazole derivatives, for example in accordance with WO 10/136109 and WO 2011/000455, or bridged carbazoles, for example in accordance with WO 2011/088877 and WO 2011/128017.

If the compound of the formula (I) is employed as component of a mixed-matrix system, it is preferably employed in combination with an aromatic ketone or an aromatic phosphine oxide, for example in accordance with WO 2004/013080, WO 2004/093207, WO 2006/005627 or WO 2010/006680, or in combination with a triazine derivative, for example in accordance with WO 2010/015306, WO 2007/063754 or WO 2008/056746, or in combination with a carbazole derivative, indolocarbazole derivative or indenocarbazole derivative, for example in accordance with WO 2007/063754, WO 2008/056746, WO 2010/136109 or WO 2011/000455.

Preferred phosphorescent dopants for use in mixed-matrix systems comprising the compounds according to the invention are the phosphorescent dopants shown in a following table.

In a further preferred embodiment of the invention, the compounds of the formula (I) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer.

If the compound of the formula (I) is employed as hole-transport material in a hole-transport layer, the compound can be employed as pure material, i.e. in a proportion of 100%, in the hole-transport layer or it can be employed in combination with further compounds in the hole-transport layer.

In a further embodiment of the invention, the compounds of the formula (I) are employed as fluorescent dopants in an emitting layer. In particular, the compounds are suitable as fluorescent dopants if they are substituted by one or more aromatic systems, preferably aromatic systems containing 12 to 20 aromatic ring atoms. The compounds according to the invention are preferably used as green or blue emitters.

The proportion of the compound of the formula (I) as dopant in the mixture of the emitting layer is in this case between 0.1 and 50.0% by vol., preferably between 0.5 and 20.0% by vol., particularly preferably between 0.5 and 8.0% by vol. Correspondingly, the proportion of the matrix material is between 50.0 and 99.9% by vol., preferably between 80.0 and 99.5% by vol., particularly preferably between 92.0 and 99.5% by vol.

Preferred matrix materials for use in combination with the compounds according to the invention as fluorescent dopants are mentioned in one of the following sections. They correspond to the matrix materials for fluorescent dopants that are indicated as preferred.

In a further preferred embodiment of the invention, the compounds of the formula (I) are employed as electron-blocking material. In this case, the compounds are preferably employed in an electron-blocking layer which is located between anode and emitting layer, preferably between hole-transport layer and emitting layer.

In a further preferred embodiment of the invention, the compounds of the formula (I) are employed as exciton-blocking material. In this case, the compounds are preferably employed in an exciton-blocking layer which is located between anode and emitting layer, preferably between hole-transport layer and emitting layer. If the compounds of the formula (I) are employed as exciton-blocking material, these preferably contain as groups A groups of the formula (II), where $Ar^1$ represents a phenyl group or an ortho- or meta-biphenyl group, which may in each case be substituted by one or more radicals $R^2$.

The organic electroluminescent device according to the invention may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers, where the various colours in this embodiment of the invention together give white light. Particular preference is given to three-layer systems, i.e. systems having three emitting layers, where one pr more of these layers comprises a compound of the formula (I) and where the three layers exhibit blue, green and orange or red emission (for the basic structure see, for example, WO 2005/011013). Likewise, emitters which have broad-band emission bands and thus exhibit white emission are suitable for white emission in such systems. Alternatively and/or additionally, the compounds according to the invention may also be present in a hole-transport layer or electron-transport layer or in another layer in such systems.

The further functional materials preferably employed in the electronic devices according to the invention are shown below.

The compounds shown in the following table are particularly suitable phosphorescent dopants.

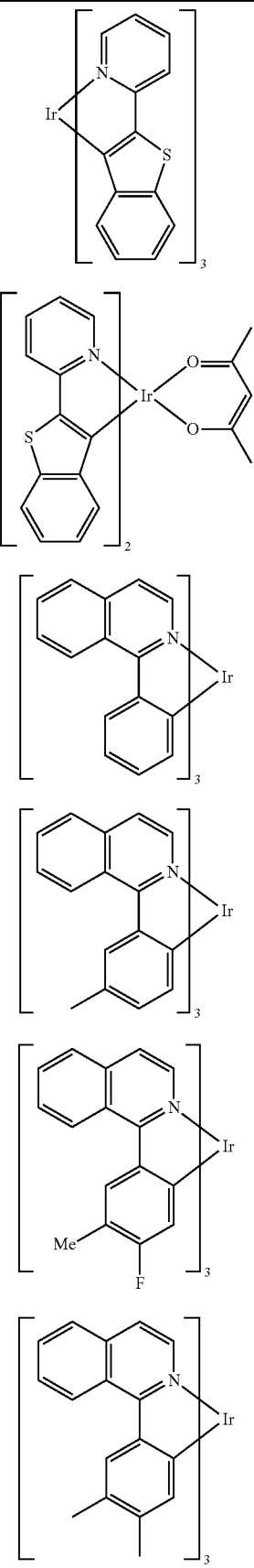

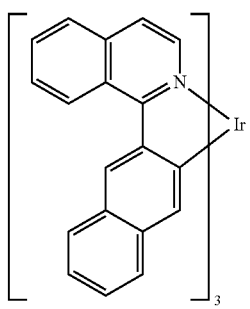
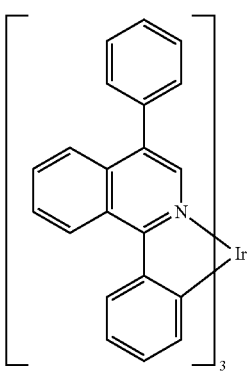
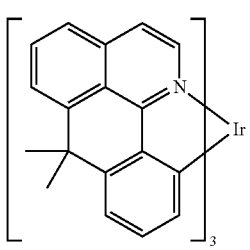
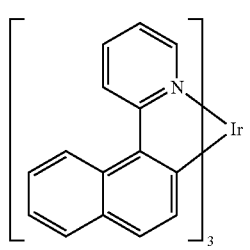
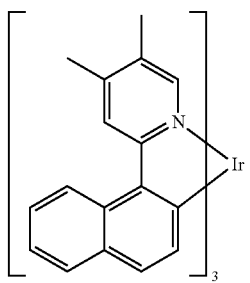
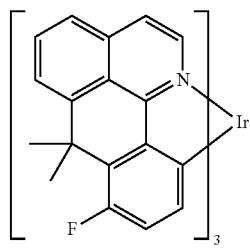
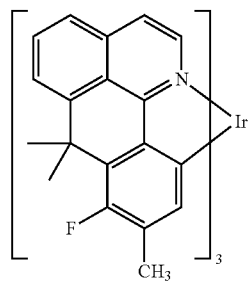
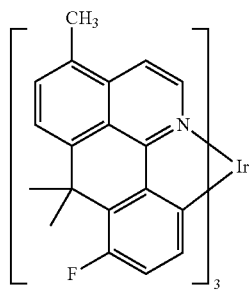
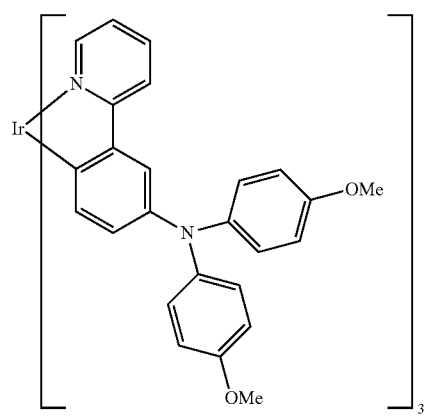
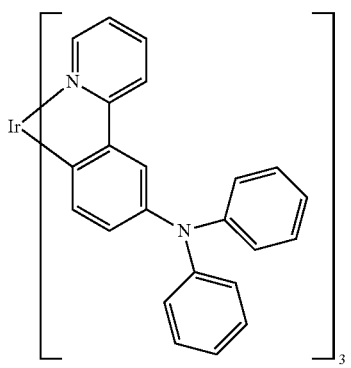

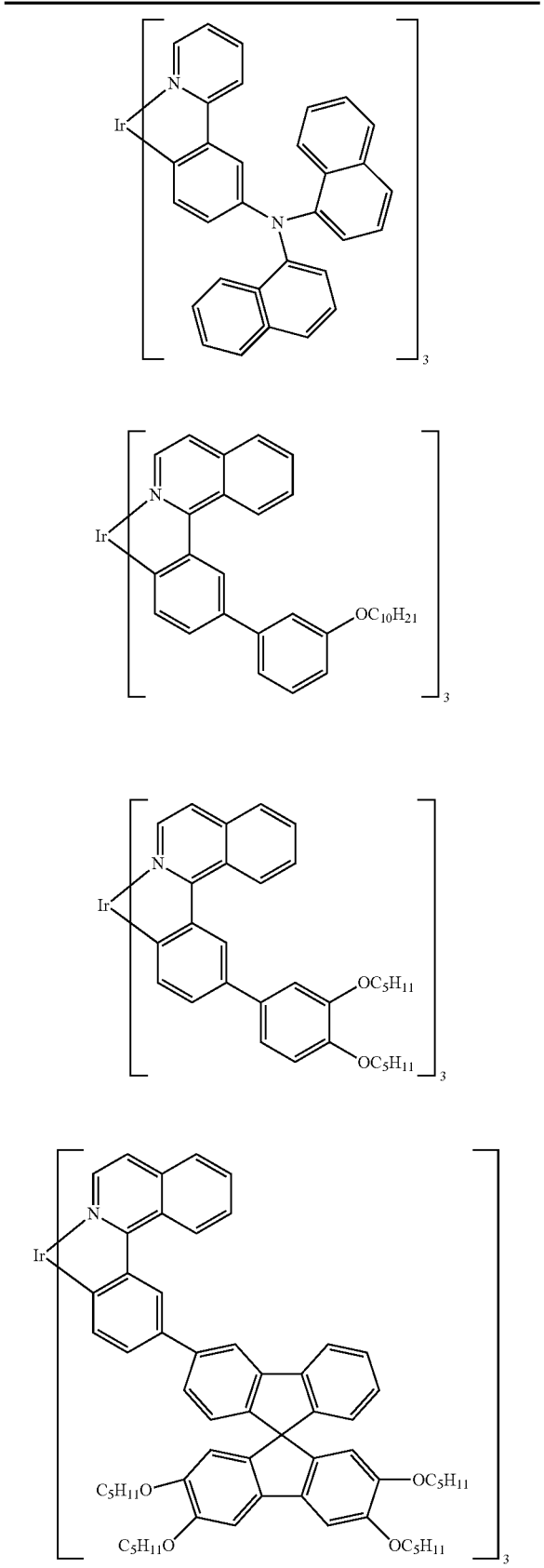
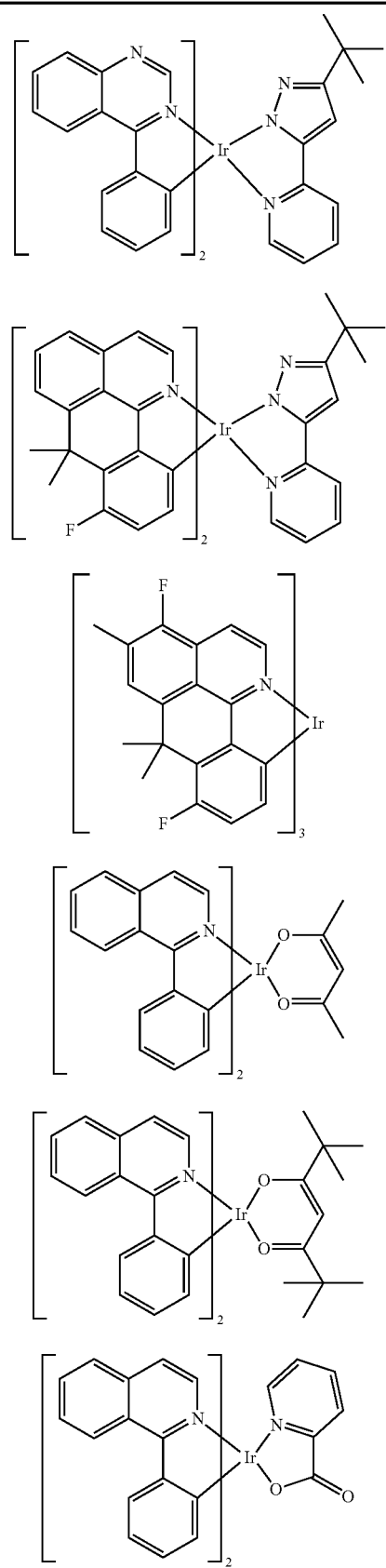

81
-continued
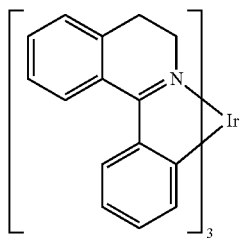
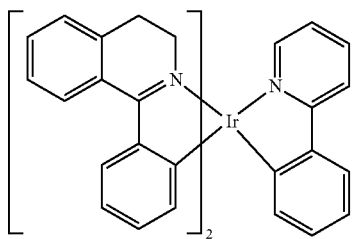
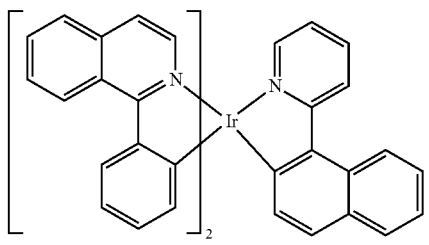
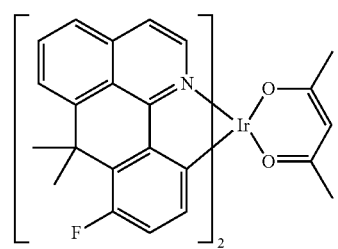
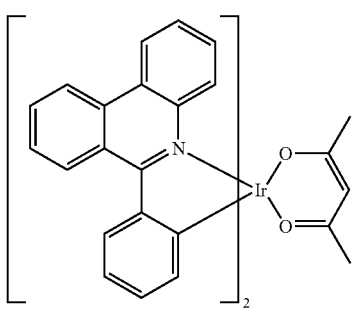
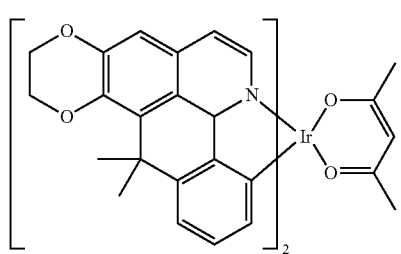
82
-continued
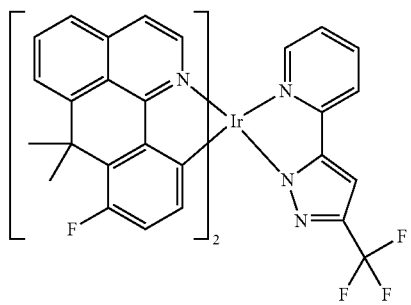
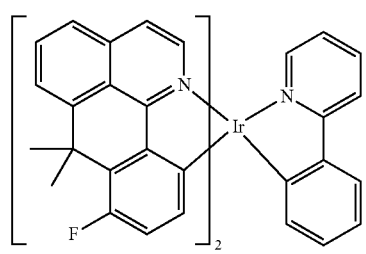
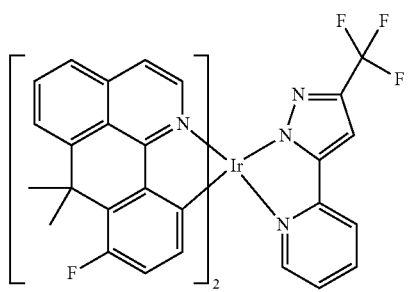
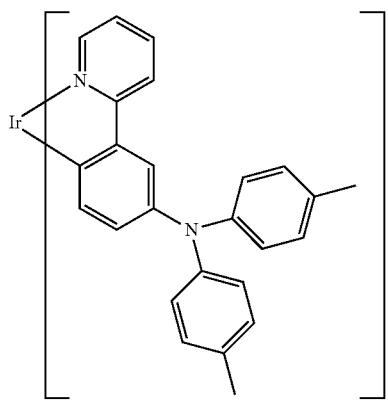
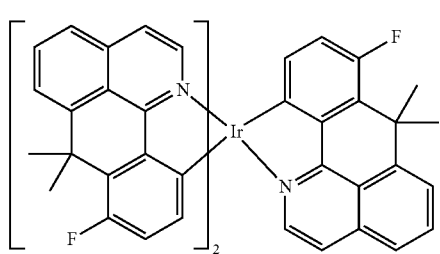

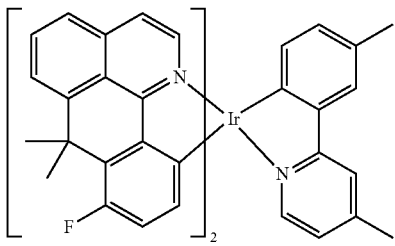
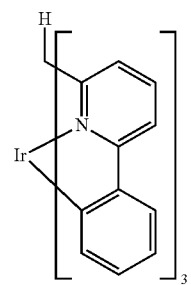
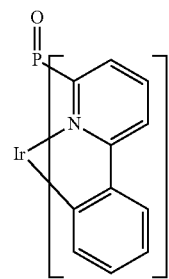
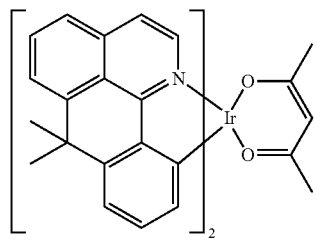
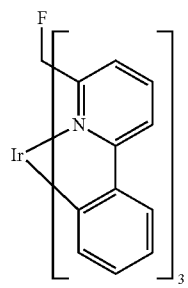
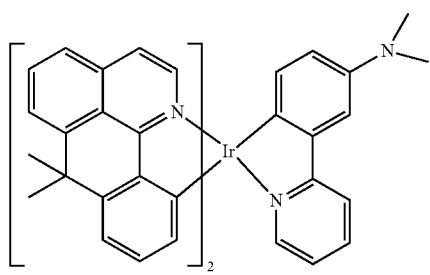
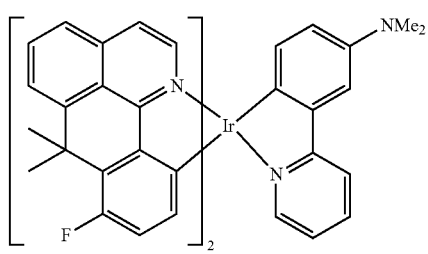
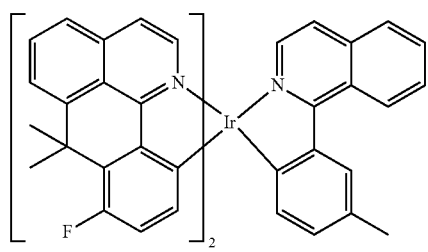
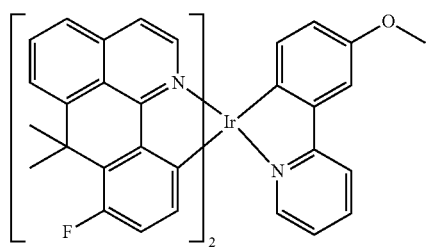
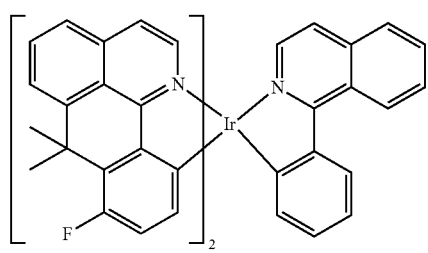
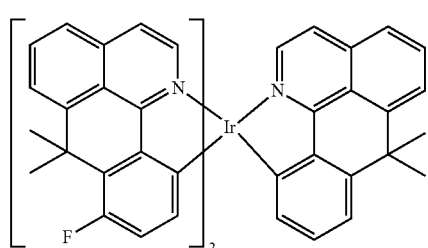

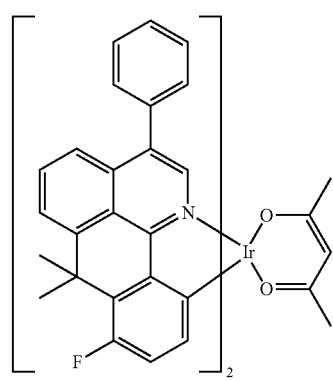
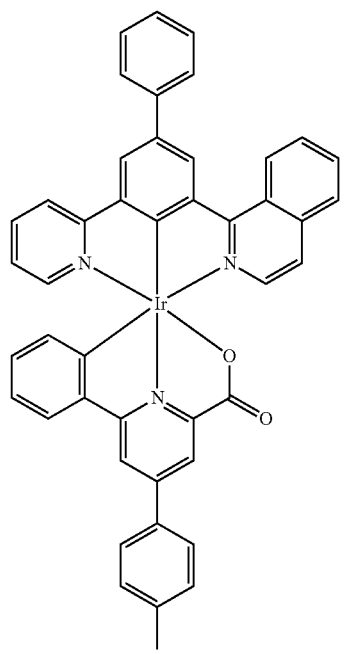
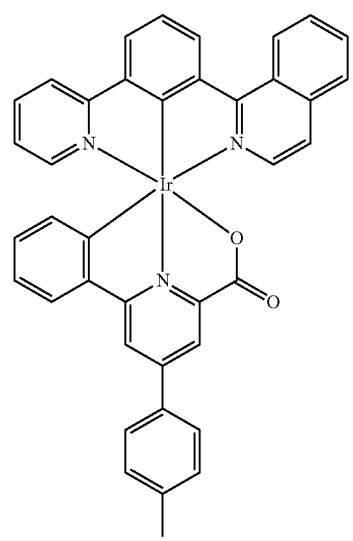
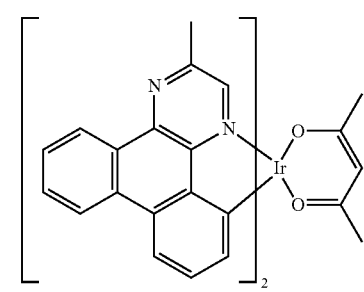
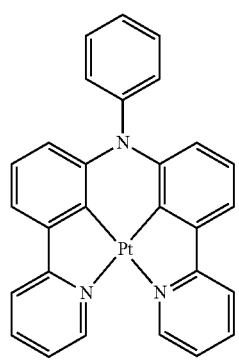
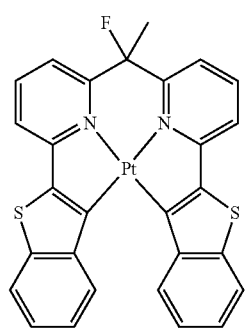
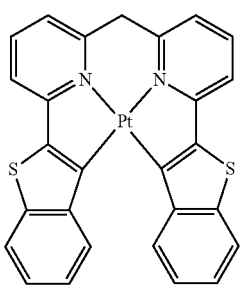

87
-continued
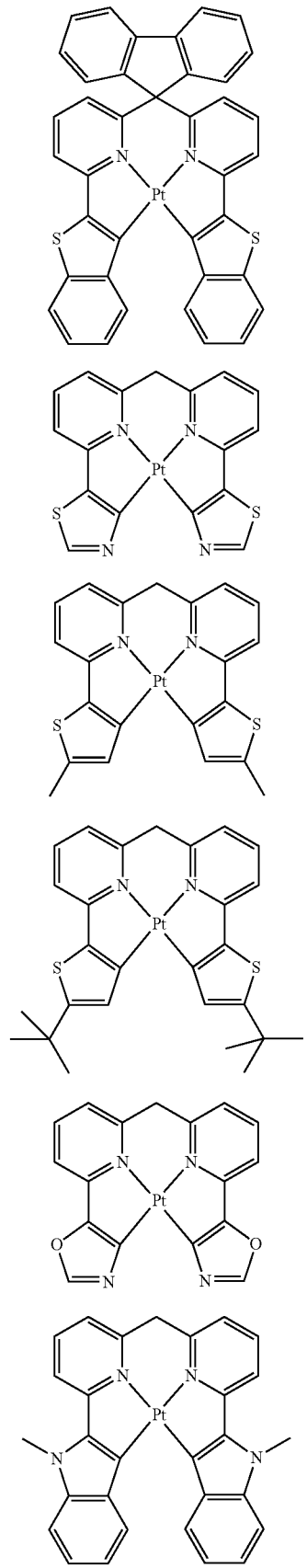
88
-continued
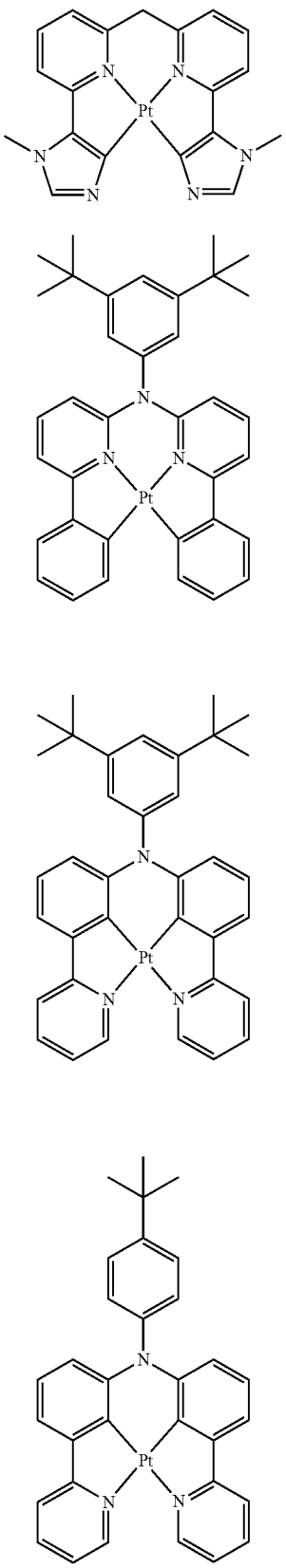

89
-continued
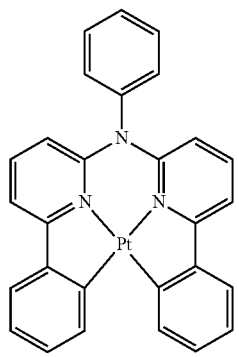
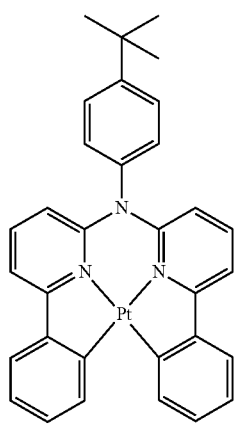
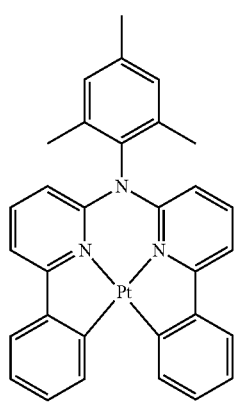
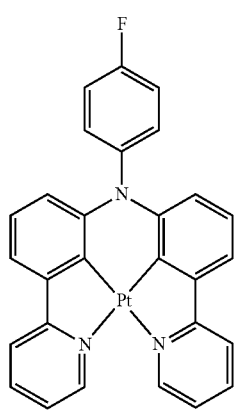
90
-continued
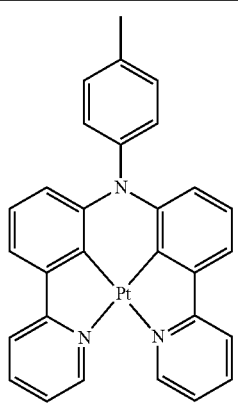
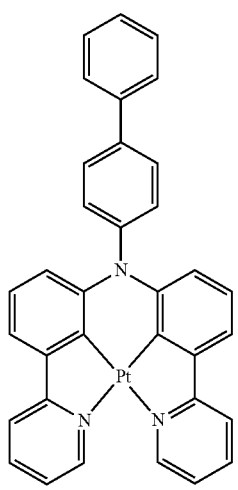
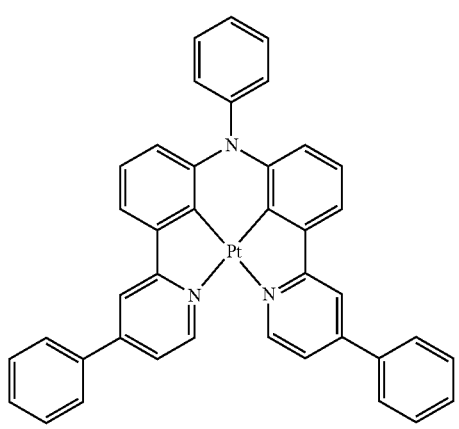

91
-continued
92
-continued
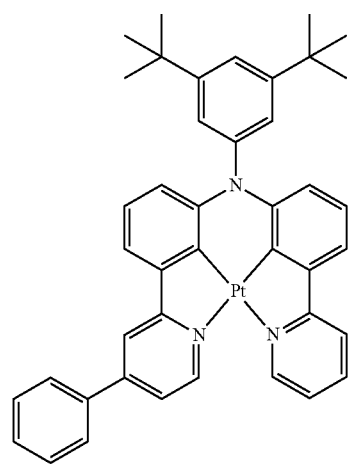
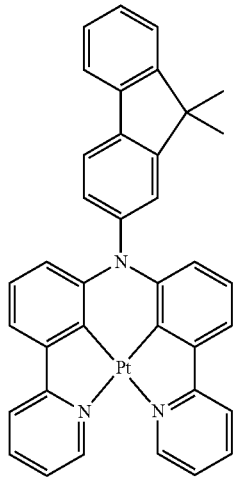
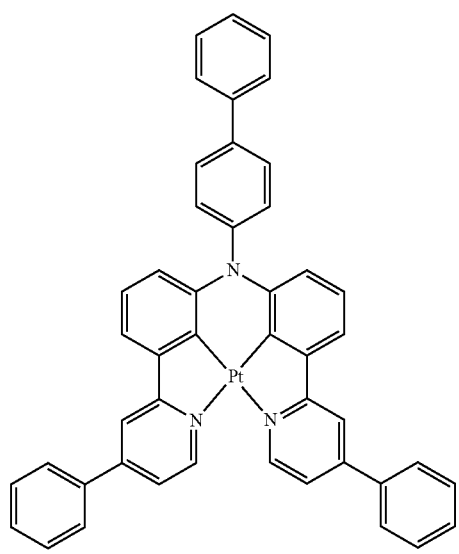
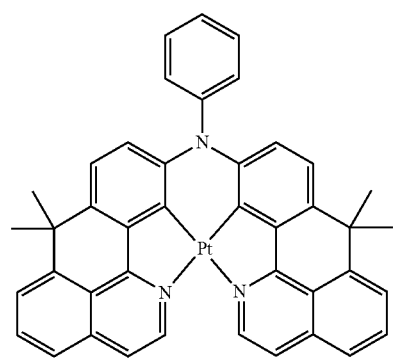

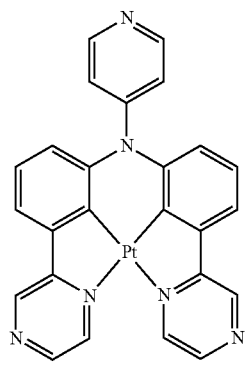
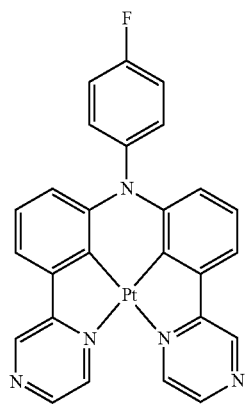
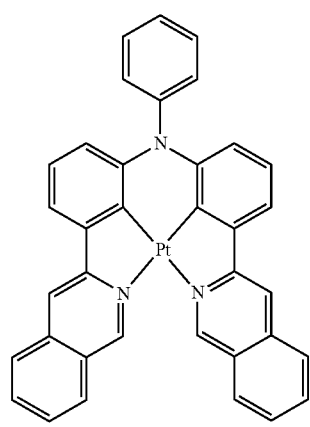
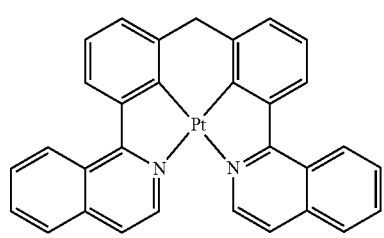
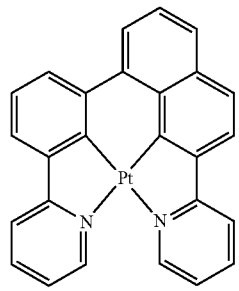
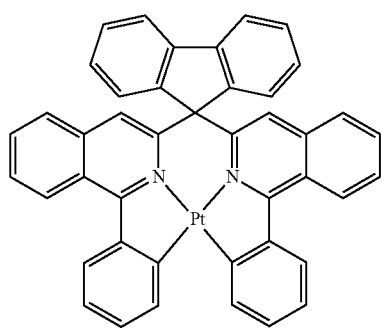
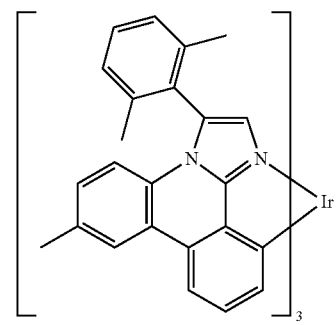
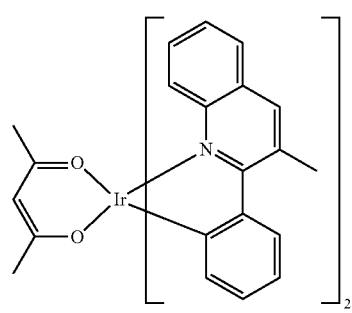
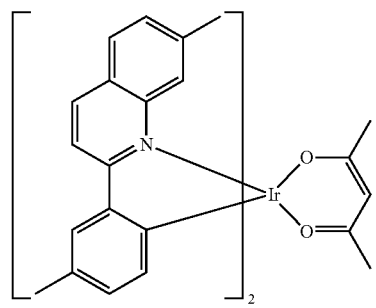

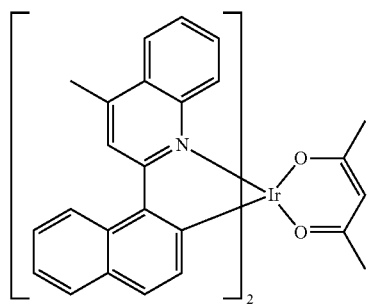
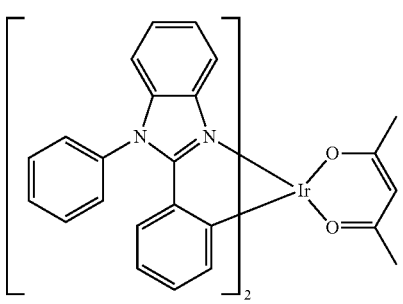
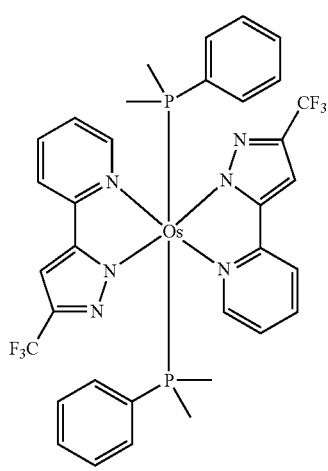
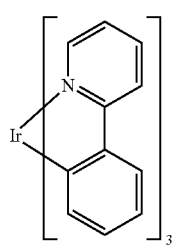
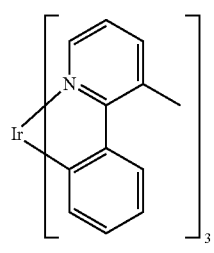
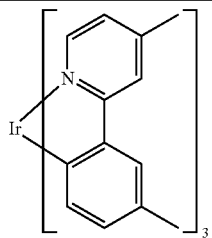
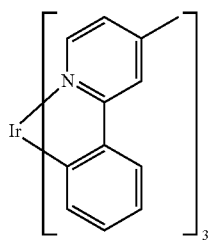
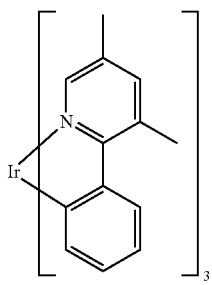
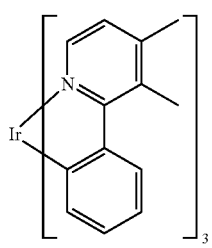
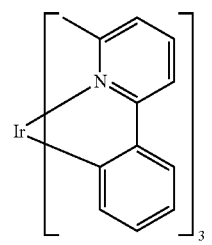
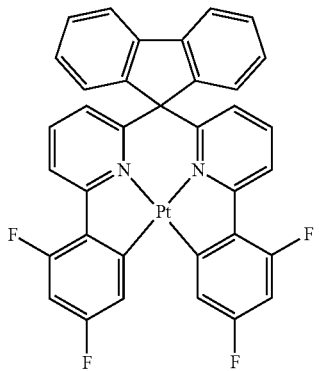

97
-continued
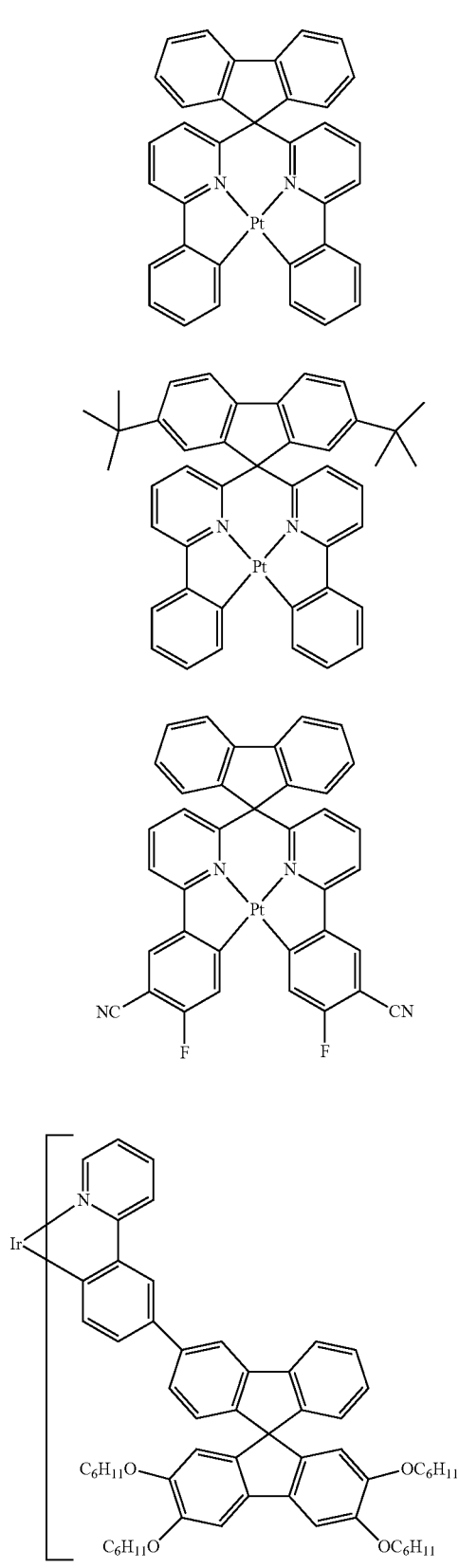
98
-continued
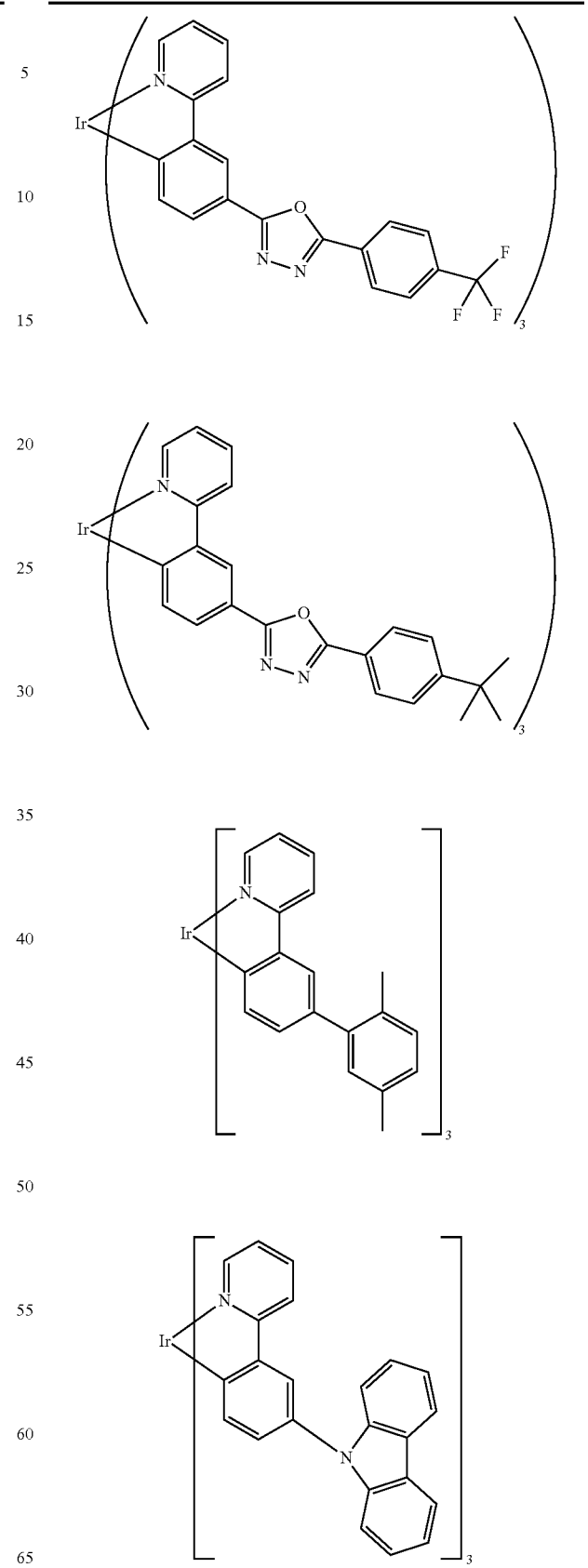

99
-continued
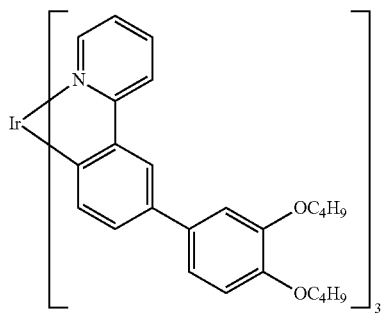
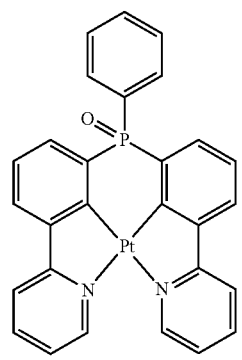
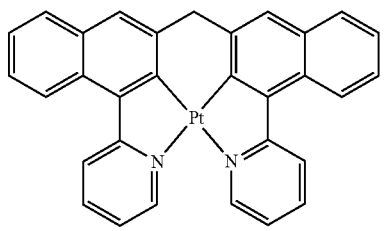
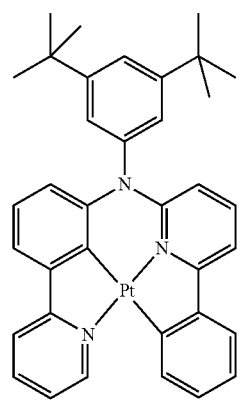
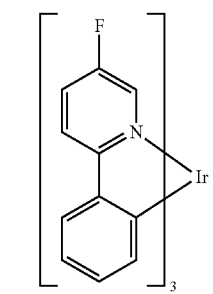
100
-continued
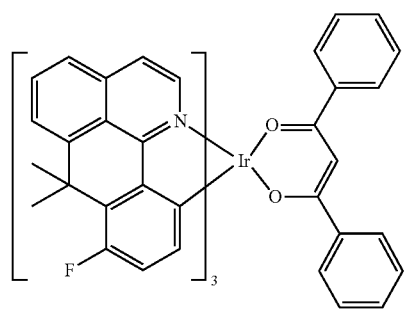
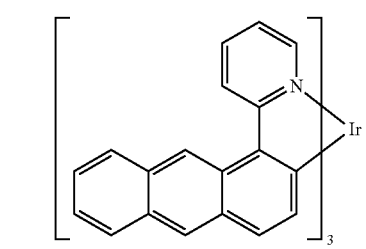
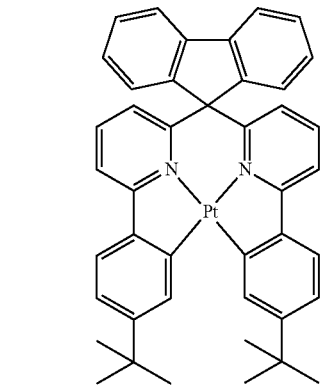
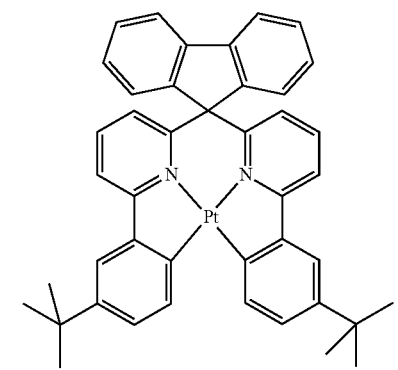

| 101 -continued | 102 -continued |
|---|---|
| 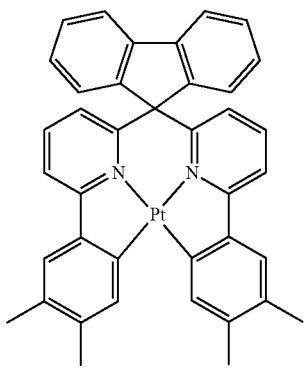<br><br>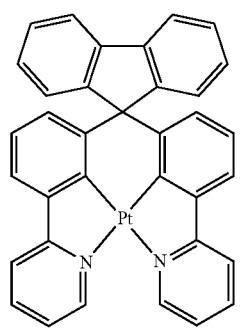<br><br>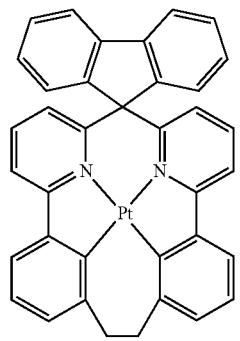<br><br>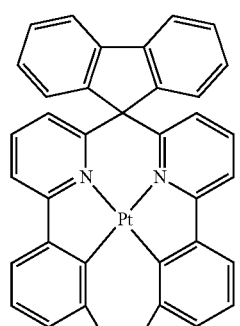 | 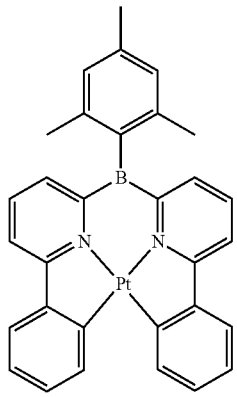<br><br>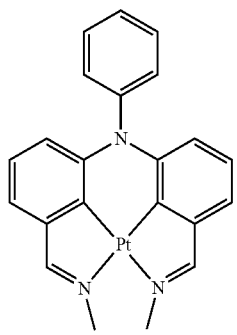<br><br>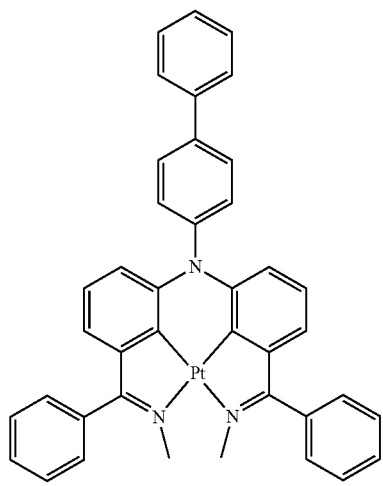<br><br>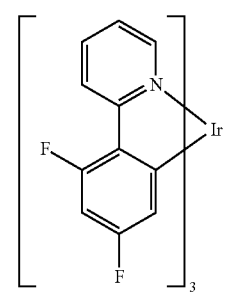 |

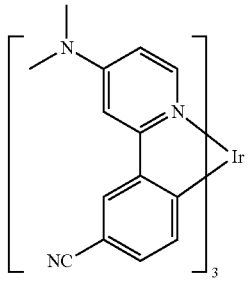
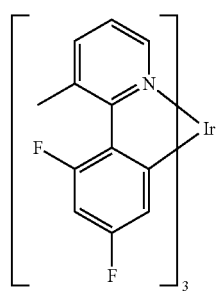
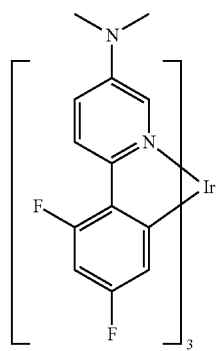
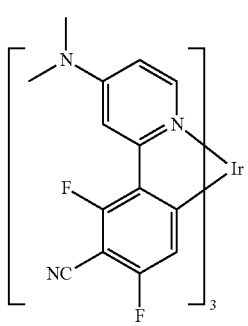
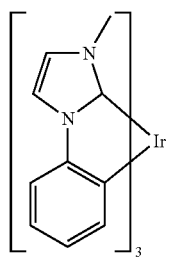
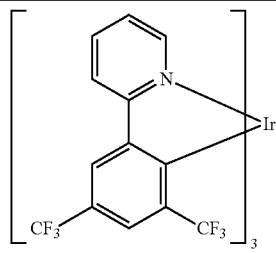
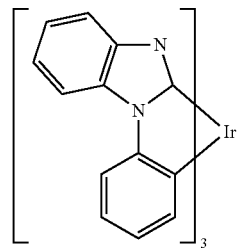
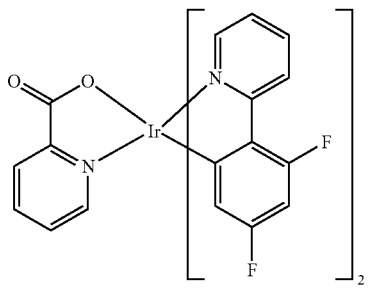
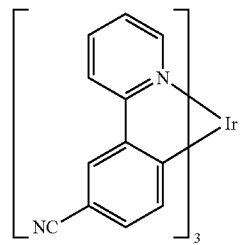
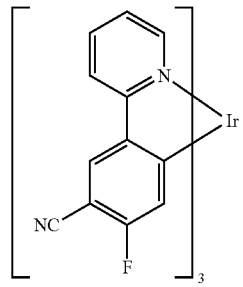

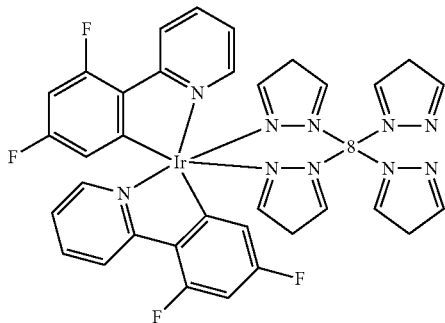

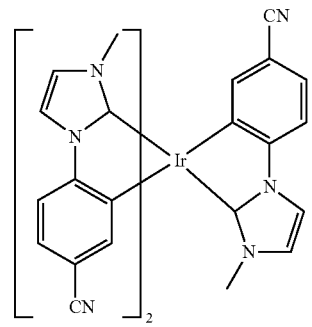

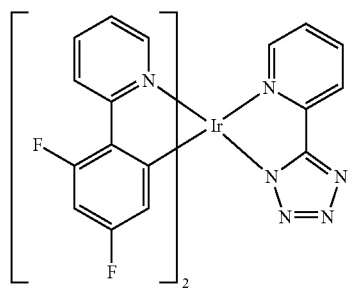

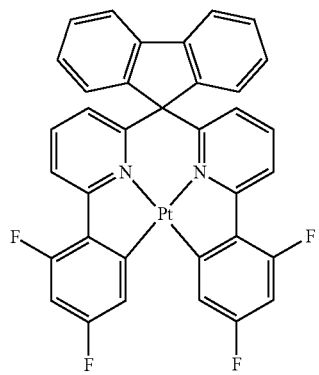

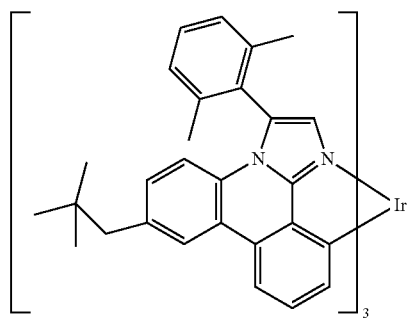

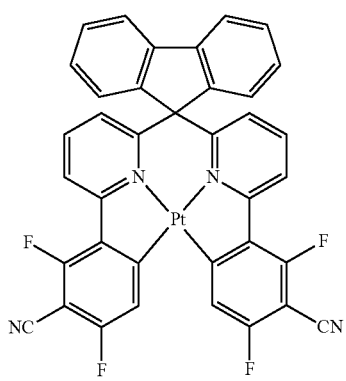

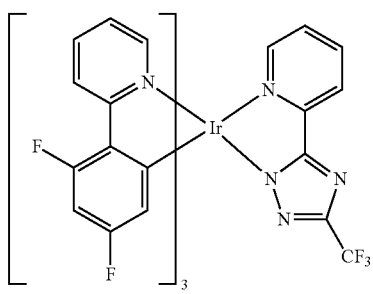

Preferred fluorescent dopants are selected from the class of the mono-styrylamines, the distyrylamines, the tristyrylamines, the tetrastyrylamines, the styrylphosphines, the styryl ethers and the arylamines. A monostyryl-amine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding styrylphosphines and styryl ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent dopants are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorene-diamines, for example in accordance with WO 2007/140847. Examples of fluorescent dopants from the class of the styrylamines are substituted or unsubstituted tristilbenamines or the fluorescent dopants described in WO 2006/000388, WO 2006/058737, WO 2006/000389, WO 2007/065549 and WO 2007/115610. Preference is furthermore given to the condensed hydrocarbons disclosed in WO 2010/012328. Furthermore, the compounds of the formula (I) can also be used as fluorescent dopants.

Suitable fluorescent dopants are furthermore the structures disclosed in JP 2006/001973, WO 2004/047499, WO 2006/098080, WO 2007/065678, US 2005/0260442 and WO 2004/092111.

Suitable matrix materials, preferably for fluorescent dopants, are materials from various classes of substance. Preferred matrix materials are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, the oligoarylenevinylenes (for example DPVBi or Spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the structures disclosed in WO 2004/018587, WO 2008/006449, U.S. Pat. No. 5,935,721, US 2005/0181232, JP 2000/273056, EP 681019, US 2004/0247937 and US 2005/0211958.

Preferred matrix materials for phosphorescent dopants, besides the compounds according to the invention, are carbazole derivatives (for example CBP, N,N-biscarbazolylbiphenyl) or compounds in accordance with WO 2005/039246, US 2005/0069729, JP 2004/288381, EP 1205527 or WO 2008/086851), triarylamines, azacarbazoles (for example in accordance with EP 1617710, EP 1617711, EP 1731584, JP 2005/347160), indolocarbazole derivatives (for example in accordance with WO 2007/063754 or WO 2008/056746), ketones (for example in accordance with WO 2004/093207 or WO 2010/006680), phosphine oxides, sulfoxides and sulfones (for example in accordance with WO 2005/003253), oligophenyl-enes, aromatic amines (for example in accordance with US 2005/0069729), bipolar matrix materials (for example in accordance with WO 2007/137725), silanes (for example in accordance with WO 2005/111172), azaboroles or boronic esters (for example in accordance with WO 2006/117052), triazine derivatives (for example in accordance with WO 2010/015306, WO 2007/063754 or WO 2008/056746), zinc complexes (for example in accordance with WO 2009/062578), aluminium complexes (for example BAlq), diazasilole and tetraazasilole derivatives, for example in accordance with WO 2010/054730, indenocarbazole derivatives, for example in accordance with WO 2010/136109 and WO 2011/000455 or diazaphospholes, for example in accordance with WO 2010/054730.

Suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LIE, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The organic electroluminescent devices comprising one or more compounds according to the invention can be employed in displays, as light sources in lighting applications and as light sources in medical and/or cosmetic applications (for example light therapy).

The compounds according to the invention are distinguished, in particular, by the fact that they effect good power efficiencies, low operating voltages and long lifetimes of the devices on use in organic electroluminescent devices.

The compounds are furthermore oxidation-stable, temperature-stable and have a high glass-transition temperature, which is advantageous both for the processability, for example from solution or from the gas phase, and also for use in electronic devices.

Finally, the compounds have a high excited triplet level, which is highly desired, in particular on use in an emitting layer in combination with a phosphorescent emitter compound.

The invention is explained in greater detail by the following use examples, where the invention is not restricted to the scope of the examples.

WORKING EXAMPLES

A) Synthesis Examples

The following syntheses are carried out, unless indicated otherwise, in dried solvents under a protective-gas atmosphere. The solvents and reagents can be purchased from ALDRICH or ABCR.

Example 1

2,4,6-Trimethyl-N,N,N',N',N'',N''-hexaphenylbenzene-1,3,5-triamine

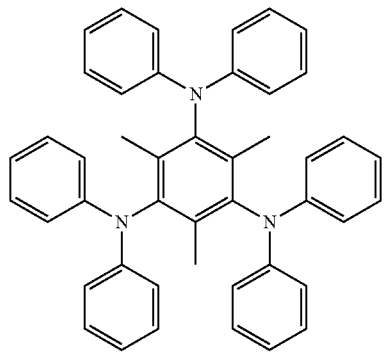 [SMILES: Cc1c(N(c2ccccc2)c2ccccc2)c(C)c(N(c2ccccc2)c2ccccc2)c(C)c1N(c1ccccc1)c1ccccc1]

14.0 ml (14 mmol) of tris-tert-butylphosphine, 1M in toluene, 1.6 g (7 mmol) of palladium(II) acetate and then 103.0 g (1.1 mol) of sodium tert-butoxide are added successively to a solution of 85.0 g (238 mmol) of 1,3,5-tribromo-2,4,6-trimethylbenzene [608-72-0] and 161.2 g (953 mmol) of diphenylamine in 2000 ml of toluene. The reaction mixture is heated under reflux for 16 h, allowed to cool to 60° C., 20 ml of acetic acid and 250 ml of water are added, the mixture is allowed to cool to room temperature, the aqueous phase is separated off, the org. phase is washed once with 500 ml of water and once with 500 ml of sat. sodium chloride solution, and the toluene is then removed in vacuo. The residue is washed by boiling once with 1000 ml of ethanol, dried in vacuo and then recrystallised six times from DMF (about 5 ml/g). A double fractional sublimation in a high vacuum (p about $10^{-6}$ mbar, T about 290° C.) is subsequently carried out. Yield: 69.6 g (112 mmol), 47% purity according to HPLC>99.9%.

The following compounds were obtained analogously, using the amines shown in the following table instead of diphenylamine:

| Ex. | Amine | Product | Yield |
|---|---|---|---|
| 2 | 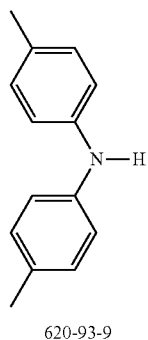 620-93-9 | 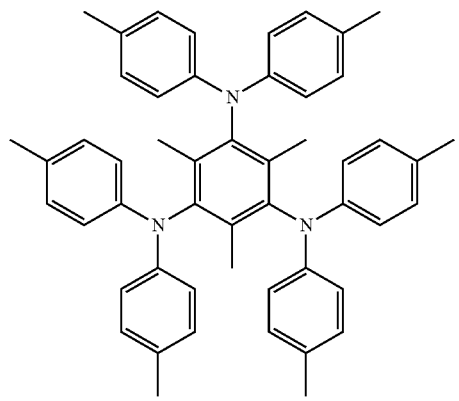 | 56% |
| 3 | 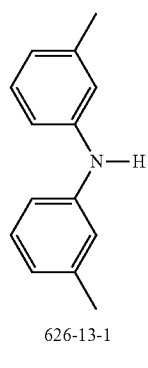 626-13-1 | 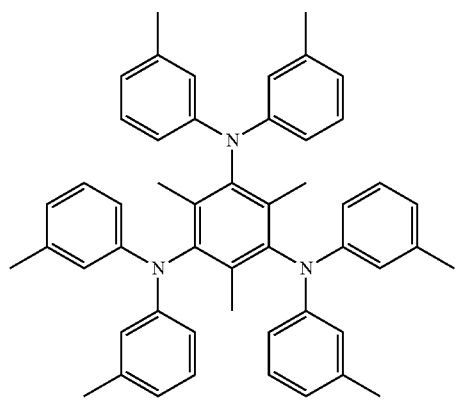 | 38% |
| 4 | 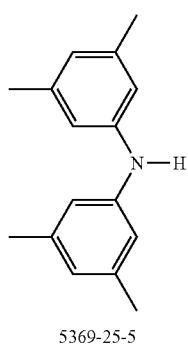 [SMILES: Cc1cc(C)cc(Nc2cc(C)cc(C)c2)c1] 5369-25-5 | 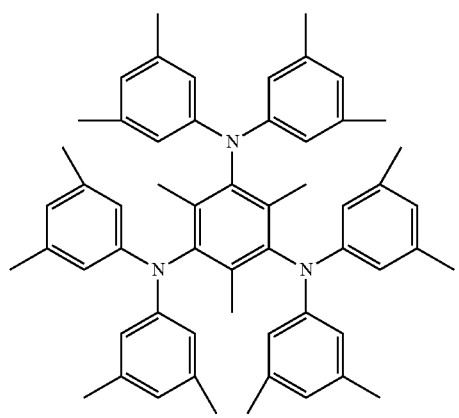 | 46% |

| Ex. | Amine | Product | Yield |
|---|---|---|---|
| 5 | 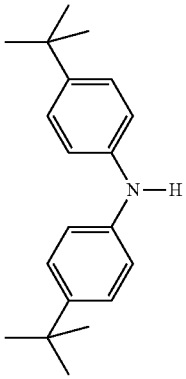<br>4627-22-9 | 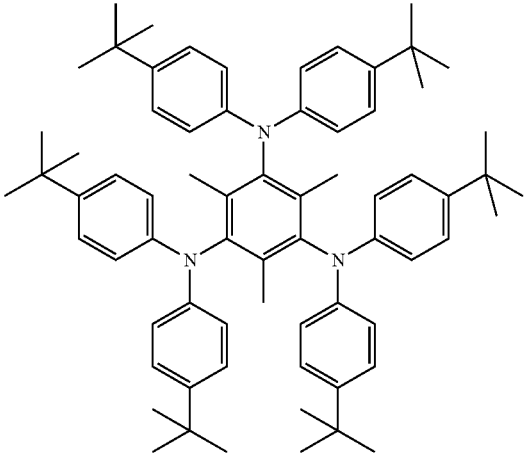 [SMILES: Cc1c(N(c2ccc(C(C)(C)C)cc2)c2ccc(C(C)(C)C)cc2)c(C)c(N(c2ccc(C(C)(C)C)cc2)c2ccc(C(C)(C)C)cc2)c(C)c1N(c1ccc(C(C)(C)C)cc1)c1ccc(C(C)(C)C)cc1] | 52% |
| 6 | 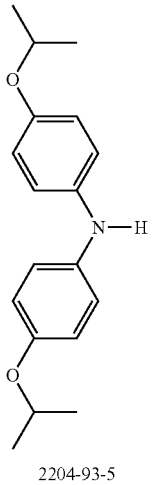 [SMILES: CC(C)Oc1ccc(Nc2ccc(OC(C)C)cc2)cc1]<br>2204-93-5 | 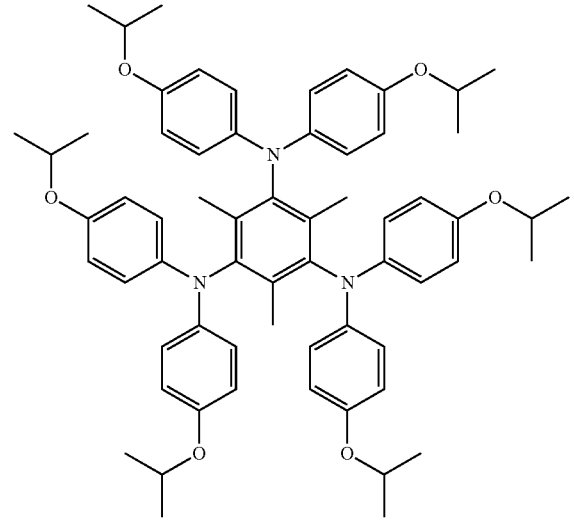 [SMILES: Cc1c(N(c2ccc(OC(C)C)cc2)c2ccc(OC(C)C)cc2)c(C)c(N(c2ccc(OC(C)C)cc2)c2ccc(OC(C)C)cc2)c(C)c1N(c1ccc(OC(C)C)cc1)c1ccc(OC(C)C)cc1] | 27% |
| 7 | 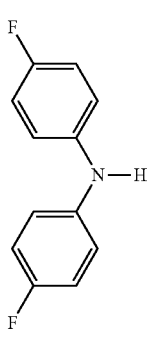<br>330-91-6 | 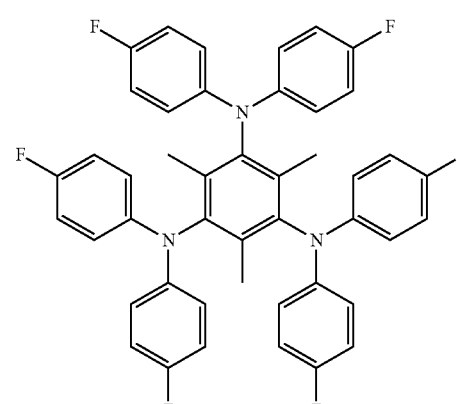 | 58% |

| Ex. | Amine | Product | Yield |
|---|---|---|---|
| 8 | 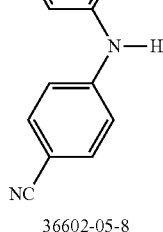 36602-05-8 | 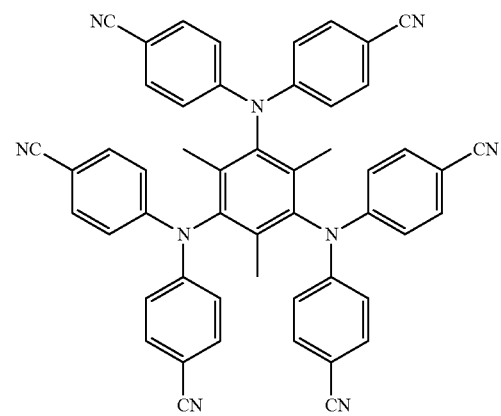 [SMILES: Cc1c(N(c2ccc(C#N)cc2)c2ccc(C#N)cc2)c(C)c(N(c2ccc(C#N)cc2)c2ccc(C#N)cc2)c(C)c1N(c1ccc(C#N)cc1)c1ccc(C#N)cc1] | 55% |
| 9 | 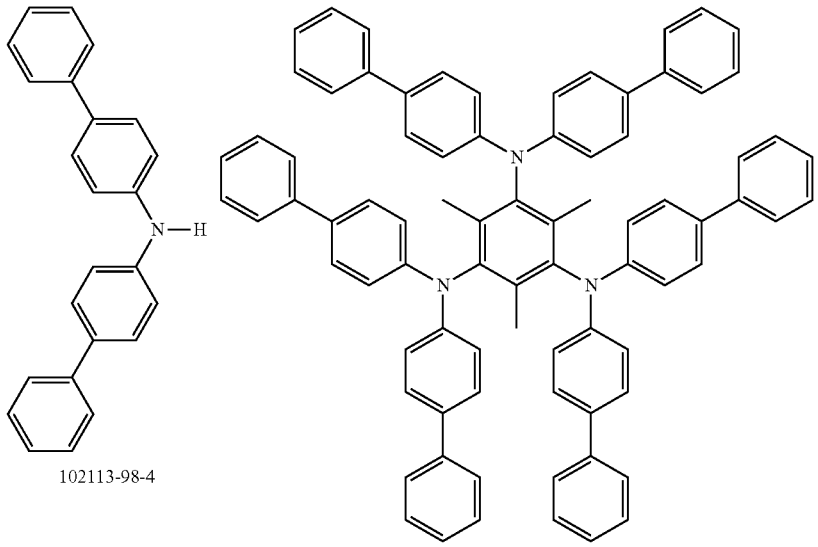 102113-98-4 | | 58% |
Product was not sublimed, but instead heated at 280° C. in vacuo
| | | | |
|---|---|---|---|
| 10 | 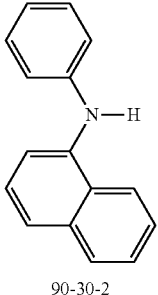 [SMILES: c1ccc(Nc2cccc3ccccc23)cc1] 90-30-2 | 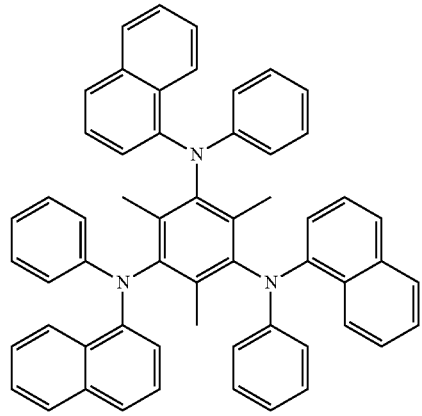 [SMILES: Cc1c(N(c2ccccc2)c2cccc3ccccc23)c(C)c(N(c2ccccc2)c2cccc3ccccc23)c(C)c1N(c1ccccc1)c1cccc2ccccc12] | 47% |

-continued
| Ex. | Amine | Product | Yield |
|---|---|---|---|
| 11 | 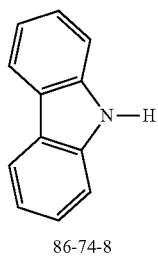 [SMILES: c1ccc2c(c1)[nH]c1ccccc12] 86-74-8 | 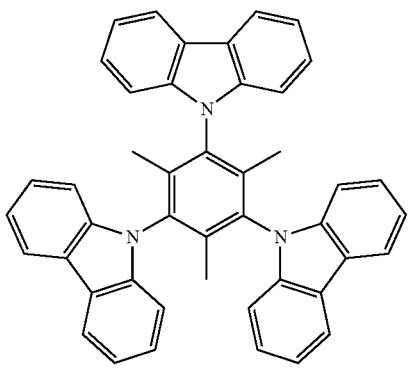 [SMILES: Cc1c(-n2c3ccccc3c3ccccc32)c(C)c(-n2c3ccccc3c3ccccc32)c(C)c1-n1c2ccccc2c2ccccc21] | 50% |
| 12 | 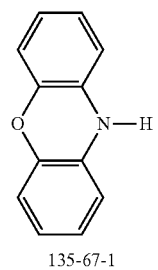 [SMILES: c1ccc2c(c1)Nc1ccccc1O2] 135-67-1 | 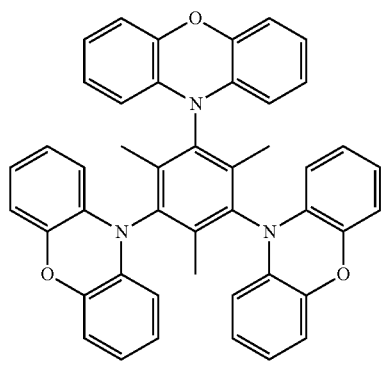 [SMILES: Cc1c(N2c3ccccc3Oc3ccccc32)c(C)c(N2c3ccccc3Oc3ccccc32)c(C)c1N1c2ccccc2Oc2ccccc21] | 50% |
| 13 | 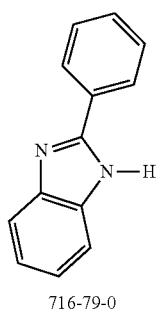 [SMILES: c1ccc(-c2nc3ccccc3[nH]2)cc1] 716-79-0 | 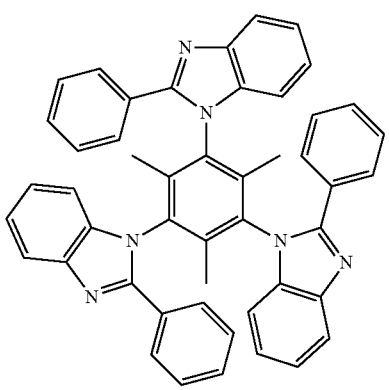 [SMILES: Cc1c(-n2c(-c3ccccc3)nc3ccccc32)c(C)c(-n2c(-c3ccccc3)nc3ccccc32)c(C)c1-n1c(-c2ccccc2)nc2ccccc21] | 65% |

-continued

| Ex. | Amine | Product | Yield |
|---|---|---|---|
| 19 | 2562-77-8 | | 57% |
| 20 | 36677-31-3 | | 11% |
| 21 | 95-15-7 | | 28% |

The following compounds were obtained analogously, using the tribromobenzene derivatives shown in the following table instead of 1,3,5-tribromo-2,4,6-trimethylbenzene:

| Ex. | Tribromide | Product | Yield |
|---|---|---|---|
| 14 | 80717-52-8 | | 46% |
| 15 | 2368-49-2 | | 52% |
| 16 | 60510-14-7 | | 41% |
| 17 | 859785-26-5 | | 34% |

-continued

| Ex. | Tribromide | Product | Yield |
|-----|------------|---------|-------|
| 18 | 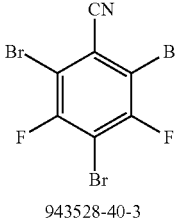943528-40-3 | 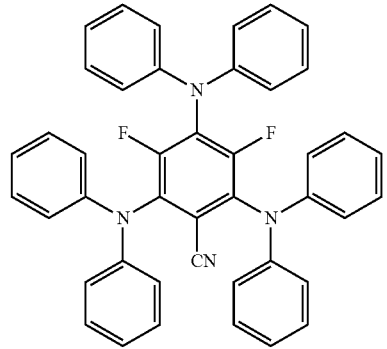 [SMILES: N#Cc1c(N(c2ccccc2)c2ccccc2)c(F)c(N(c2ccccc2)c2ccccc2)c(F)c1N(c1ccccc1)c1ccccc1] | 37% |

B) Device Examples: Production and Characterisation of Organic Electroluminescent Devices Electroluminescent devices according to the invention can be produced as described in general terms, for example, in WO 2005/003253. The results for OLEDs according to the invention having different structures are compared below. The basic structure, the materials used, the degree of doping and the layer thicknesses thereof are identical for better comparability.

OLEDs comprising the compounds according to the invention in accordance with Example 1, 2, 3, 4, 5, 10, 11, 13, 14, 19, 20 and 21 as hole-transport material (HTL2), or as matrix material in a mixed-matrix system, or as electron-transport material are produced in the following layer structure (device Examples D1-D15):

| | |
|---|---|
| Hole-injection layer (HIL) | 70 nm of 2,2',7,7'-tetrakis(di-para-tolyl-amino)spiro-9,9'-bifluorene |
| Hole-transport layer (HTL1) | 5 nm of 1,4,5,8,9,11-hexaazatriphenylene-hexacarbonitrile |
| Hole-transport layer (HTL2) | 15 nm, see table compound according to the invention, |
| Emission layer (EML): host and dopant | 40 nm see Table 1, proportions in % by vol. |
| Electron conductor (ETL) | 40 nm of ETM1 (50% by vol.) or see table compound according to the invention and ETM2 (50% by vol.) |
| Cathode | 1 nm of ETM2, 100 nm of Al on top. |

Furthermore, OLEDs comprising hole-transport material HTL3 in accordance with the prior art are produced for comparison (device Examples V1-V2).

The structures of the compounds used with the exception of the compounds according to the invention (see table Synthesis Examples) are depicted below for clarity.

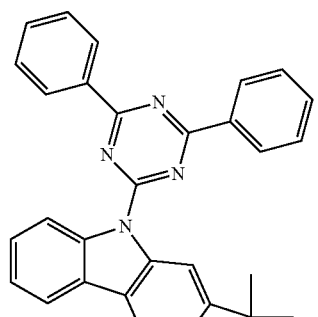

Host1

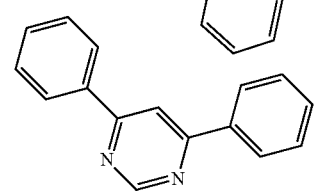

Host2

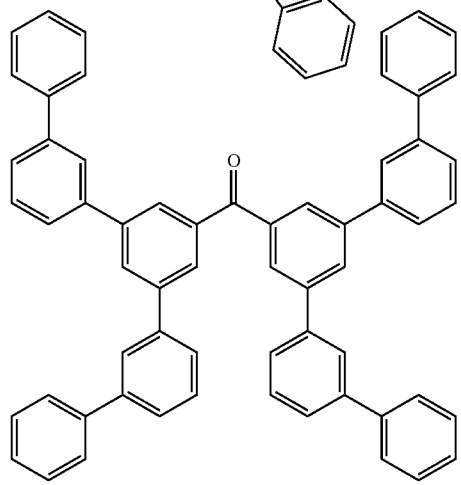

Host3

-continued

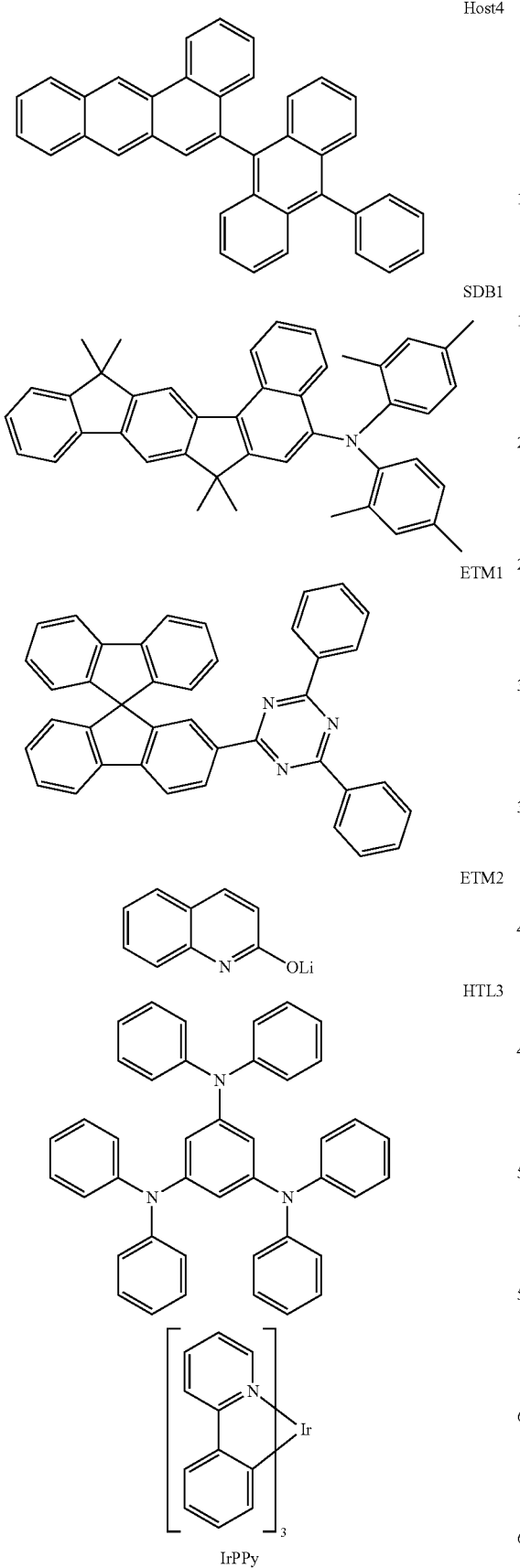

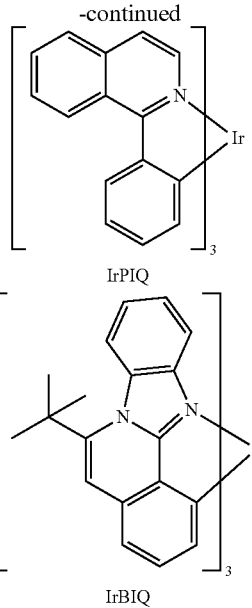

For characterisation of the OLEDs produced, the electroluminescence spectra and the external quantum efficiency (EQE, measured in %) as a function of the luminance, calculated from current/voltage/luminance characteristic lines (IUL characteristic lines), are determined.

TABLE 1

Device results

| Ex. | HTL2 | Host/dopant | ETL | EQE at 1000 cd/m² [%] | Voltage at 1000 cd/m² [V] | CIE x/y |
|---|---|---|---|---|---|---|
| D1 | Ex. 1 | Host 1, 90% IrPPy, 10% | ETM1, 50% ETM2, 50% | 15.8 | 8.8 | 0.35/0.62 |
| D2 | Ex. 2 | Host 1, 90% IrPPy, 10% | ETM1, 50% ETM2, 50% | 16.0 | 4.3 | 0.35/0.62 |
| D3 | Ex. 4 | Host 1, 90% IrPPy, 10% | ETM1, 50% ETM2, 50% | 16.3 | 4.0 | 0.35/0.62 |
| D4 | Ex. 10 | Host 1, 90% IrPPy, 10% | ETM1, 50% ETM2, 50% | 14.2 | 3.8 | 0.35/0.62 |
| D5 | Ex. 14 | Host 1, 90% IrPPy, 10% | ETM1, 50% ETM2, 50% | 13.5 | 8.5 | 0.36/0.63 |
| D6 | Ex. 10 | Host 1, 85% IrPIQ, 15% | ETM1, 50% ETM2, 50% | 12.1 | 3.4 | 0.68/0.31 |
| D7 | Ex. 4 | Host 2, 85% IrBIQ, 15% | ETM1, 50% ETM2, 50% | 12.3 | 6.2 | 0.16/0.29 |
| D8 | Ex. 4 | Host 3, 65% Ex. 1, 25% IrBIQ, 10% | ETM1, 50% ETM2, 50% | 13.6 | 5.7 | 0.16/0.29 |
| D9 | Ex. 2 | Host 1, 70% Ex. 2, 20% IrPPy, 10% | ETM1, 50% ETM2, 50% | 17.3 | 3.6 | 0.35/0.62 |
| D10 | Ex. 2 | Host 1, 70% Ex. 11, 20% IrPPy, 10% | ETM1, 50% ETM2, 50% | 15.2 | 4.6 | 0.35/0.62 |
| D11 | Ex. 4 | Host 4, 90% SDB1, 10% | ETM1, 50% ETM2, 50% | 8.1 | 5.2 | 0.14/0.14 |
| D12 | Ex. 3 | Host 4, 90% SDB1, 10% | Ex. 13, 50% ETM2, 50% | 7.9 | 5.2 | 0.14/0.14 |
| D13 | Ex. 5 | Host 4, 90% SDB1, 10% | Ex. 19, 50% ETM2, 50% | 8.0 | 5.5 | 0.14/0.13 |
| D14 | Ex. 1 | Host 1, 65% Ex. 11, 20% IrPPy, 15% | Ex. 20, 50% ETM2, 50% | 16.8 | 4.4 | 0.35/0.63 |
| D15 | Ex. 1 | Host 2, 70% Ex. 11, 20% IrPPy, 10% | Ex. 21, 50% ETM2, 50% | 17.0 | 4.5 | 0.35/0.62 |

TABLE 1-continued

Device results

| Ex. | HTL2 | Host/<br>dopant | ETL | EQE at<br>1000<br>cd/m² <br>[%] | Voltage at<br>1000<br>cd/m²<br>[V] | CIE<br>x/y |
|---|---|---|---|---|---|---|
| V1<br>Comp.<br>Ex. | HTL3 | Host 2, 85%<br>IrBIQ, 15% | ETM1, 50%<br>ETM2, 50% | 5.7 | 6.3 | 0.16/<br>0.31 |
| V2<br>Comp.<br>Ex. | HTL3 | Host 1, 90%<br>IrPPy, 10% | ETM1, 50%<br>ETM2, 50% | 11.0 | 4.5 | 0.36/<br>0.62 |

It becomes clear from the performance data measured for device Examples D1-D15 that very good results with respect to operating voltage and power efficiency can be obtained with the compounds in accordance with the present invention, both on use as hole-transport materials (D1-D11) and also on use as matrix materials for phosphorescent emitters (D8-D10) and also on use as electron-transport material (D12-15). Examples D1-D10, D14, D15 here relate to OLEDs having a phosphorescent emitter layer, and Examples D11-D13 relate to OLEDs having a fluorescent emitter layer.

The comparison with hole-transport material HTL3 in accordance with the prior art (device Examples V30 and V31) shows that, for an identical structure, better performance data are achieved with the compounds according to the invention (cf. V1 with Example D7 according to the invention and V2 with Examples D1-05 according to the invention).

The invention claimed is:
1. A compound of a formula (I)

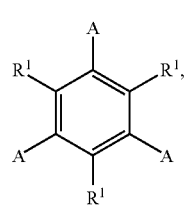

formula (I)

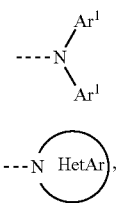

formula (II)

formula (III)

wherein A is, identically or differently on each occurrence, a group of the following formula (II) or (III)

wherein the dashed line emanating from the nitrogen atom represents the bond from the group A to the central benzene ring;
wherein the group HetAr including the nitrogen atom shown is, identically or differently on each occurrence, a heteroaryl group having 5 to 30 aromatic ring atoms, optionally substituted by one or more radicals $R^2$;

wherein the group $Ar^1$ is, identically or differently on each occurrence, an aromatic or heteroaromatic ring system having 5 to 30 aromatic ring atoms, optionally substituted by one or more radicals $R^2$, and wherein the two groups $Ar^1$ may be connected via a group Y so that a ring is formed with the nitrogen atom of the group A, wherein
Y is selected from a single bond, $BR^2$, $C(R^2)_2$, $Si(R^2)_2$, $NR^2$, $PR^2$, $P(=O)R^2$, $P(=S)R^2$, O, S, S=O, and $S(=O)_2$; and
$R^1$ is, identically or differently on each occurrence, CN, $C(=O)R^3$, $C(=O)OR^3$, $C(=O)N(R^3)_2$, $P(=O)(R^3)_2$, $OSO_2R^3$, $S(=O)R^3$, $S(=O)_2R^3$, or a heteroaryl group selected from pyridyl, pyrazinyl, pyridazinyl, pyrimidyl and triazinyl, each of which optionally substituted by one or more radicals $R^3$;
$R^2$ is, identically or differently on each occurrence, H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkyl group having 1 to 20 C atoms, a branched or cyclic alkyl, alkoxy or thioalkyl group having 3 to 20 C atoms, or an alkenyl or alkynyl group having 2 to 20 C atoms, wherein the above-mentioned groups are optionally substituted by one or more radicals $R^3$ and wherein one or more $CH_2$ groups in the above-mentioned groups are optionally replaced by $-R^3C=CR^3-$, $Si(R^3)_2$, C=O, C=S, $C=NR^3$, $-C(=O)O-$, $-C(=O)NR^3-$, $NR^3$, $P(=O)(R^3)$, $-O-$, $-S-$, SO, or $SO_2$, and wherein one or more H atoms in the above-mentioned groups are optionally replaced by D, F, Cl, Br, I, CN, or $NO_2$, or an aromatic or heteroaromatic ring system having 5 to 60 aromatic ring atoms, optionally substituted by one or more radicals $R^3$, or an aryloxy or heteroaryloxy group having 5 to 60 aromatic ring atoms, optionally substituted by one or more radicals $R^3$, or an aralkyl or heteroaralkyl group having 5 to 60 aromatic ring atoms, optionally substituted by one or more radicals $R^3$, wherein two or more radicals $R^2$ are optionally linked to one another and optionally form a ring;
$R^3$ is, identically or differently on each occurrence, H, D, F, Cl, Br, I, $B(OR^4)_2$, CHO, $C(=O)R^4$, $CR^4=C(R^4)_2$, CN, $C(=O)OR^4$, $C(=O)N(R^4)_2$, $Si(R^4)_3$, $N(R^4)_2$, $NO_2$, $P(=O)(R^4)_2$, $OSO_2R^4$, $OR^4$, $S(=O)R^4$, $S(=O)_2R^4$, a straight-chain alkyl, alkoxy or thioalkyl group having 1 to 20 C atoms, or a branched or cyclic alkyl, alkoxy or
thioalkyl group having 3 to 20 C atoms, or an alkenyl or alkynyl group having 2 to 20 C atoms, wherein the above-mentioned groups are optionally substituted by one or more radicals $R^4$ and wherein one or more $CH_2$ groups in the above-mentioned groups are optionally replaced by $-R^4C=CR^4-$, $-C\equiv C-$, $Si(R^4)_2$, C=O, C=S, $C=NR^4$, $-C(=O)O-$, $-C(=O)NR^4-$, $NR^4$, $P(=O)(R^4)$, $-O-$, $-S-$, SO, or $SO_2$, and wherein one or more H atoms in the above-mentioned groups are optionally replaced by D, F, Cl, Br, I, CN, or $NO_2$, or an aromatic or heteroaromatic ring system having 5 to 60 aromatic ring atoms, optionally substituted by one or more radicals $R^4$, or an aryloxy or heteroaryloxy group having 5 to 60 aromatic ring atoms, optionally substituted by one or more radicals $R^4$, or an aralkyl or heteroaralkyl group having 5 to 60 aromatic ring atoms, optionally substituted by one or more radicals R⁴, wherein two or more radicals R³ are optionally linked to one another and optionally form a ring; and R⁴ is, identically or differently on each occurrence, H, D, F, or an aliphatic, aromatic or heteroaromatic organic radical having 1 to 20 C atoms, in which, in addition, one or more H atoms are optionally replaced by D or F; two or more substituents R⁴ are optionally linked to one another and optionally form a ring.

2. The compound of claim 1, wherein the groups Ar¹ of group A of formula (II) are identically or differently on each occurrence, an aryl group having 6 to 10 aromatic ring atoms.

3. The compound of claim 1, wherein the group A is identically or differently on each occurrence, of the formula (II), and each of the groups Ar¹ are connected via the group Y.

4. The compound of claim 1, wherein the group of the formula (II) is a group of the following formulae (II-1) to (II-11):

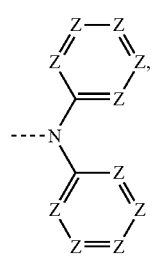

formula (II-1)

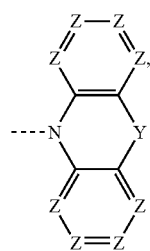

formula (II-2)

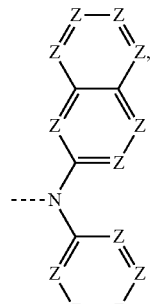

formula (II-3)

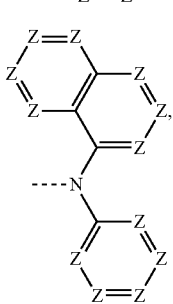

formula (II-4)

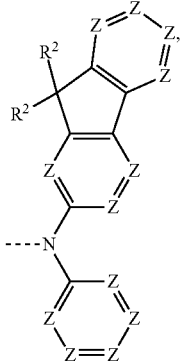

formula (II-5)

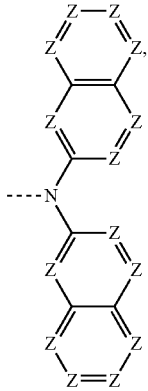

formula (II-6)

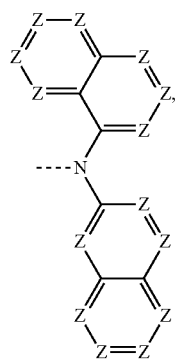

formula (II-7)

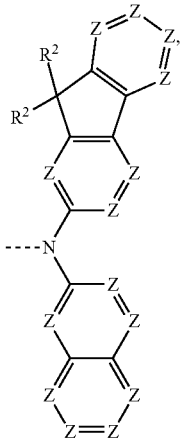

formula (II-8)

formula (II-9)

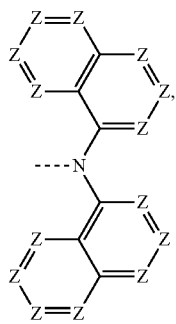

formula (II-10)

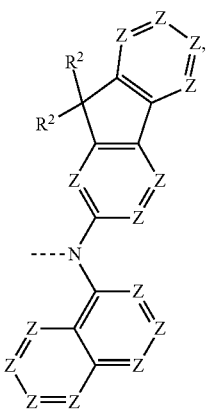

formula (II-11)

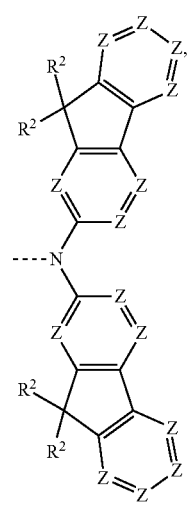

wherein

Z is, identically or differently on each occurrence, $CR^2$ or N; and

Y is selected from a single bond, $BR^2$, $C(R^2)_2$, $Si(R^2)_2$, $NR^2$, $PR^2$, $P(=O)R^2$, O, S, S=O, or $S(=O)_2$.

5. The compound of claim 1, wherein the group of the formula (III) is selected from the formulae (III-1) to (III-3):

formula (III-1)

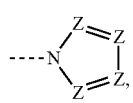

formula (III-2)

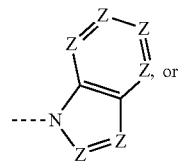

formula (III-3)

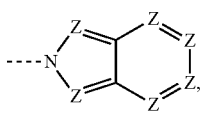

wherein

Z is, identically or differently on each occurrence, $CR^2$ or N.

6. The compound of claim 1, wherein Y is selected from a single bond, $C(R^2)_2$, $NR^2$, O, or S.

7. The compound of claim 3, wherein Y is selected from a single bond, $C(R^2)_2$, $NR^2$, O, or S.

8. The compound of claim 1, wherein the group $R^1$ is CN.

9. The compound of claim 1, wherein the radicals $R^1$ in formula (I) are selected identically.

10. The compound of claim 8, wherein the radicals $R^1$ in formula (I) are selected identically.

11. A process for the preparation of the compound of claim 1, wherein at least one intermediate of a formula (Z)

formula (Z)

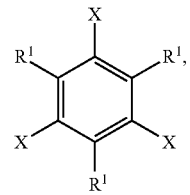

is reacted with at least one arylamino compound, or at least one heterocyclic compound containing at least one NH function, and X is, identically or differently on each occurrence, any reactive group.

12. An oligomer, polymer, or dendrimer, comprising one or more compounds of claim 1, wherein bonds to the oligomer, polymer, or dendrimer, are connected at any position of the formula (I) by $R^1$, $R^2$, or $R^3$.

13. A formulation comprising at least one compound of claim 1 and at least one solvent.

14. A formulation comprising at least one oligomer, polymer, or dendrimer, of claim 10 and at least one solvent.

15. An electronic device comprising at least one compound of claim 1, wherein the the electronic device is selected from an organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC), organic laser diode (O-laser), or organic electroluminescent device (OLED).

16. An electronic device comprising at least one oligomer, polymer or dendrimer, of claim 12, wherein the electronic device is selected from an organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC), organic laser diode (O-laser), or organic electroluminescent device (OLED).

17. An organic electroluminescent device, wherein the compound according to claim 1 is present as hole-transport material in a hole-transporting layer, as matrix material in an emitting layer, as electron-blocking material, or as exciton-blocking material.

18. An organic electroluminescent device, wherein the oligomer, polymer or dendrimer, of claim 12 is present as hole-transport material in a hole-transporting layer, as matrix material in an emitting layer, as electron-blocking material, or as exciton-blocking material.

19. An organic electroluminescent device, wherein the compound of claim 1 is present as matrix material in a phosphorescent emitting layer, wherein, in addition to the compound according to claim 1, at least one further matrix material is present in the phosphorescent emitting layer.

20. An organic electroluminescent device, wherein the oligomer, polymer or dendrimer, of claim 12, is present as matrix material in a phosphorescent emitting layer, wherein, in addition to the compound according to claim 1, at least one further matrix material is present in the phosphorescent emitting layer.

* * * * *